(12) United States Patent
March et al.

(10) Patent No.: US 9,265,842 B2
(45) Date of Patent: Feb. 23, 2016

(54) COMPOSITIONS AND METHODS FOR TREATING ENDOCRINE, GASTROINTESTINAL OR AUTOIMMUNE DISORDERS

(75) Inventors: John C. March, Ithaca, NY (US); Franklin Faping Duan, Syracuse, NY (US)

(73) Assignee: Cornell University, Ithaca, NY (US)

( * ) Notice: Subject to any disclaimer, the term of this patent is extended or adjusted under 35 U.S.C. 154(b) by 0 days.

(21) Appl. No.: 13/879,501

(22) PCT Filed: Oct. 13, 2011

(86) PCT No.: PCT/US2011/056174
§ 371 (c)(1),
(2), (4) Date: Oct. 21, 2013

(87) PCT Pub. No.: WO2012/051431
PCT Pub. Date: Apr. 19, 2012

(65) Prior Publication Data
US 2014/0105861 A1    Apr. 17, 2014

Related U.S. Application Data

(60) Provisional application No. 61/393,618, filed on Oct. 15, 2010, provisional application No. 61/539,121, filed on Sep. 26, 2011.

(51) Int. Cl.
| | |
|---|---|
| A01N 63/00 | (2006.01) |
| C12N 1/20 | (2006.01) |
| A61K 48/00 | (2006.01) |
| C12N 15/74 | (2006.01) |
| C07K 14/605 | (2006.01) |
| C07K 14/47 | (2006.01) |
| A61K 35/74 | (2015.01) |

(52) U.S. Cl.
CPC .............. *A61K 48/00* (2013.01); *A61K 35/74* (2013.01); *C07K 14/4702* (2013.01); *C07K 14/605* (2013.01); *C12N 15/746* (2013.01); *A61K 48/0008* (2013.01); *A61K 48/0075* (2013.01); *C07K 2319/02* (2013.01); *C07K 2319/10* (2013.01); *C12N 2830/002* (2013.01)

(58) Field of Classification Search
CPC .. C07K 14/4792; C07K 14/605; A61K 48/00; A61K 35/74
USPC ....................................................... 424/93.2
See application file for complete search history.

(56) References Cited

U.S. PATENT DOCUMENTS

| | | | |
|---|---|---|---|
| 4,234,570 | A | 11/1980 | Kanbayashi et al. |
| 7,374,930 | B2 | 5/2008 | Oh et al. |
| 8,007,777 | B2 | 8/2011 | Borek et al. |
| 2004/0106547 | A1 | 6/2004 | Larsen et al. |
| 2005/0090465 | A1 | 4/2005 | Ferber |
| 2006/0057607 | A1 | 3/2006 | Lenz et al. |
| 2006/0073525 | A1 | 4/2006 | Rivero et al. |
| 2009/0036364 | A1 | 2/2009 | Levy et al. |
| 2009/0074734 | A1 | 3/2009 | Rottiers |
| 2010/0166675 | A1 | 7/2010 | Wang et al. |
| 2010/0256332 | A1 | 10/2010 | Wallrapp et al. |

FOREIGN PATENT DOCUMENTS

| | | |
|---|---|---|
| WO | 9729180 | 2/1997 |
| WO | 03/046158 | 5/2003 |
| WO | 2009/126719 | 10/2009 |

OTHER PUBLICATIONS

Hou et al 2007, Biotechnol let. 29:1439-1446.*
Mota et al., 2006, BMC Biotechnol.. 6 (2):1-11.*
Mathiesen et al., 2008, J. Applied Microbiol. 105:215-226.*
Chen et al Wei Sheng Wu Xue Bao 47:987-991 (Abstract p. 1 of 1.*
Kajikawa et al 2010, Clinical and Vaccine Immunology 17:43-48.*
Wyborski et al 1999, Protein Expression and Purification 16:1-10.*
Nauck et al 1998, Acta Diabetol. 35:117-129.*
Bock, T., Svenstrup, K., Pakkenberg, B. & Buschard, K., "Unbiased estimation of total beta-cell number and mean beta-cell volume in rodent pancreas", Apmis 107,791-799 (1999).
Buhl et al. "Naturally occurring products of proglucagon 111-160 in the porcine and human small intestine", J. Biol. Chem., 1988, 263(18), 8621-8624.
Casteleyn, C. et al. "Surface area assessment of the murine intestinal tract as a prerequisite for oral dose translation from mouse to man", Laboratory Animals, 2010, 44, 176-183.
Chattopadhyay et al. "Effect of single amino acid mutations in the conserved GDNQ motif of L protein of Rinderpest virus on RNA synthesis in vitro and in vivo", Virus Research, 2004, 99(2),139-145.
Cheng, H. & Bjerkn

(56) References Cited

OTHER PUBLICATIONS

Cunningham, B.C. and Wells, J.A., "High-resolution epitope mapping of hGH-receptor interactions by alanine-scanning mutagenesis", Science, 1989, 244:1081.

Datsenko, K. A. & Wanner, B. L., "One-step inactivation of chromosomal genes in *Escherichia coli* K-12 using PCR products", Proc Natl Acad Sci USA 97(12), 6640-6645 (2000).

Duan, F. & March, J., "Interrupting Vibrio cholerae infection of human epithelial cells with engineered commensal bacterial signaling", Biotechnology and Bioengineering, vol. 101(1), 2008,128-134.

Duan, F. et al. "Secretion of Insulinotropic Proteins by Commensal Bacteria: Rewiring the Gut to Treat Diabetes" Applied and Environmental Microbiology, vol. 74, No. 23, 2008, 7437-7438.

Farrar, M.D. et al., "Engineering of the gut commensal bacterium Bacteroides ovatus to produce and secrete biologically active murine interleukin-2 in response to xylan", J. Applied Microbiology, 2005, vol. 98, 1191-1197.

Gorecki, D., "Prospects and problems of gene therapy: an update", Expert Opin Emerging Drugs, 2001, 6(2), 187-198.

International Bureau of WIPO, International Preliminary Report on Patentability, PCT/US09/039923 dated Oct. 12, 2010 (6 pgs.).

International Searching Authority, Korean Intellectual Property Office, International Search Report and Written Opinion issued in corresponding family PCT Application No. PCT/US2009/039923 dated Dec. 31, 2009 (5 pgs).

Irwin, D.M. and Wong, J., "Trout and chicken proglucagon: alternative splicing generates mRNA transcripts encoding glucagon-like peptide 2", Mol. Endocrinol., 1995, 9(3):267-277.

Kodama et al., "The features and shortcomings for gene delivery of current non-viral carriers", Current Medicinal Chemistry, 2006, vol. 13, 2155-2161.

Loessner, H. et al. "Drug-inducible remote control of gene expression by probiotic *Escherichia coli* Nissle 1917 in intestine, tumor and gall bladder of mice", Microbes and Infection, 2009, vol. 11(14-15), 1097-1105.

March, J. et al. "Engineering signal transduction for treating type 1 diabetes", 2007 Abstract, Amer. Chem. Society, Div. of Biochemical Technology, BIOT 144 (1 page).

Masayuki, K. et al. "Pancreatic epithelial cells can be converted into insulin-producing cells by GLP-1 in conjunction with virus-mediated gene transfer of pdx-1", Surgery, vol. 138(2), 2005, 125-133.

Meier JJ, et al. "Glucagon-like peptide 2 stimulates glucagon secretion, enhances lipid absorption, and inhibits gastric acid secretion in humans", Gastroenterology. 2006 I30(1):44-54.

Nishi and Steiner, "Cloning of complementary DNAs encoding islet amyloid polypeptide, insulin, and glucagon precursors from a New World rodent, the degu, Octodon degus" Mol. Endocrinol., 1990, 4:1192-1198.

Rao, S. et al. "Toward a live microbial microbicide for HIV: Commensal bacteria secreting an HIV fusion inhibitor peptide", Proc Natl Acad Sci USA 102(34), 11993-11998 (2005).

Ryu, S. & Garges, S. "Promoter Switch in the *Escherichia coli* Pts Operon.", Journal of Biological Chemistry, 269, 4767-4772 (1994).

Skolnick et al. "From genes to protein structure and function: novel applications of computational approaches in the genomic era", Trends in Biotechnology, 2000, vol. 18, 34-39.

Smallwood et al. "Different substitutions at conserved amino acids in domains II and III in the Sendai L RNA polymerase protein inactivate viral RNA synthesis", Virology, 2002, vol. 304, 135-145.

Steidler, L. et al. "Treatment of Murine Colitis by Lactococcus lactis Secreting Interleukin-10", Science, 2000, vol. 289, 1352-1355.

Supplementary European Search Report for EP 09730686.4 dated May 16, 2011 (8 pages).

Suzuki, A., Nakauchi, H. & Taniguchi, H., "Glucagon-like peptide 1 (1-37) converts intestinal epithelial cells into insulin-producing cells", Proc Natl Acad Sci USA 100(9), 5034-5039 (2003).

Taha, Masoumeh F., "Cell based-gene delivery approaches for the treatment of spinal cord injury and neurodegenerative disorders", Current Stem Cell Research & Therapy, 2010, 5(1), 23-36.

Tomasinsig et al. "The cathelicidins—structure, function and evolution", Current Proteins and Peptide Science, 2005, vol. 6, 23-34.

Velázquez E. et al. "Glucagon-like peptide-2 stimulates the proliferation of cultured rat astrocytes", Eur. J. Biochem. 2003, 270(14), 3001-3009.

Ylä-Herttuala S & Martin JF, "Cardiovascular gene therapy", Lancet, 2000, vol. 355, 213-222.

Yoshida, s. et al. "PDX-1 induces differentiation of intestinal epithelioid IEC-6 into insulin-producing cells", Diabetes, 2002, vol. 51, 2505-2513.

* cited by examiner

FIGS 8A–B
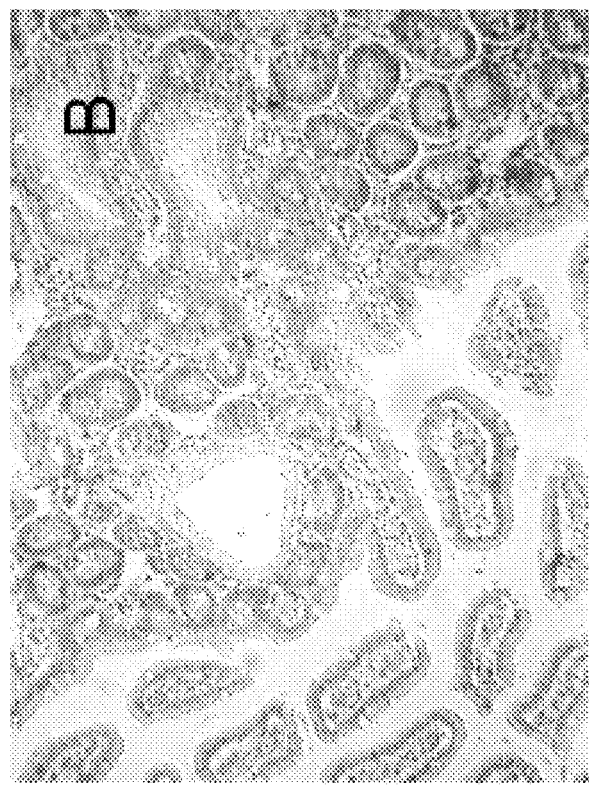
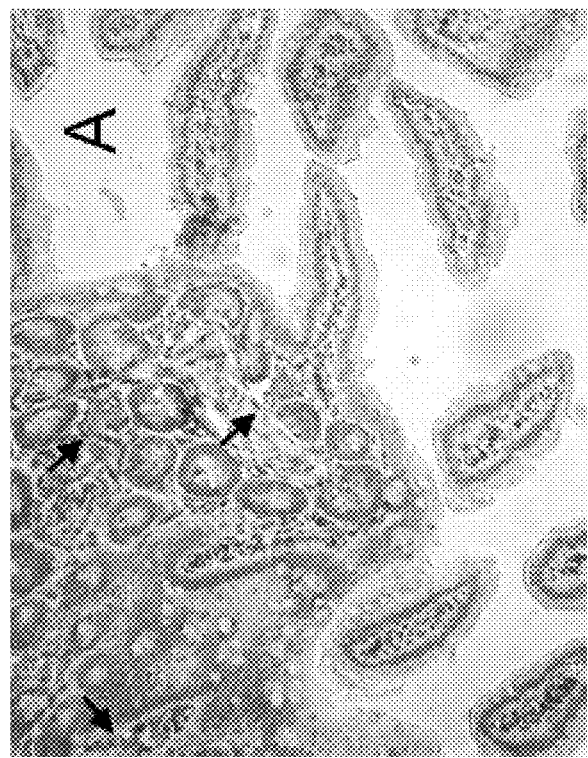

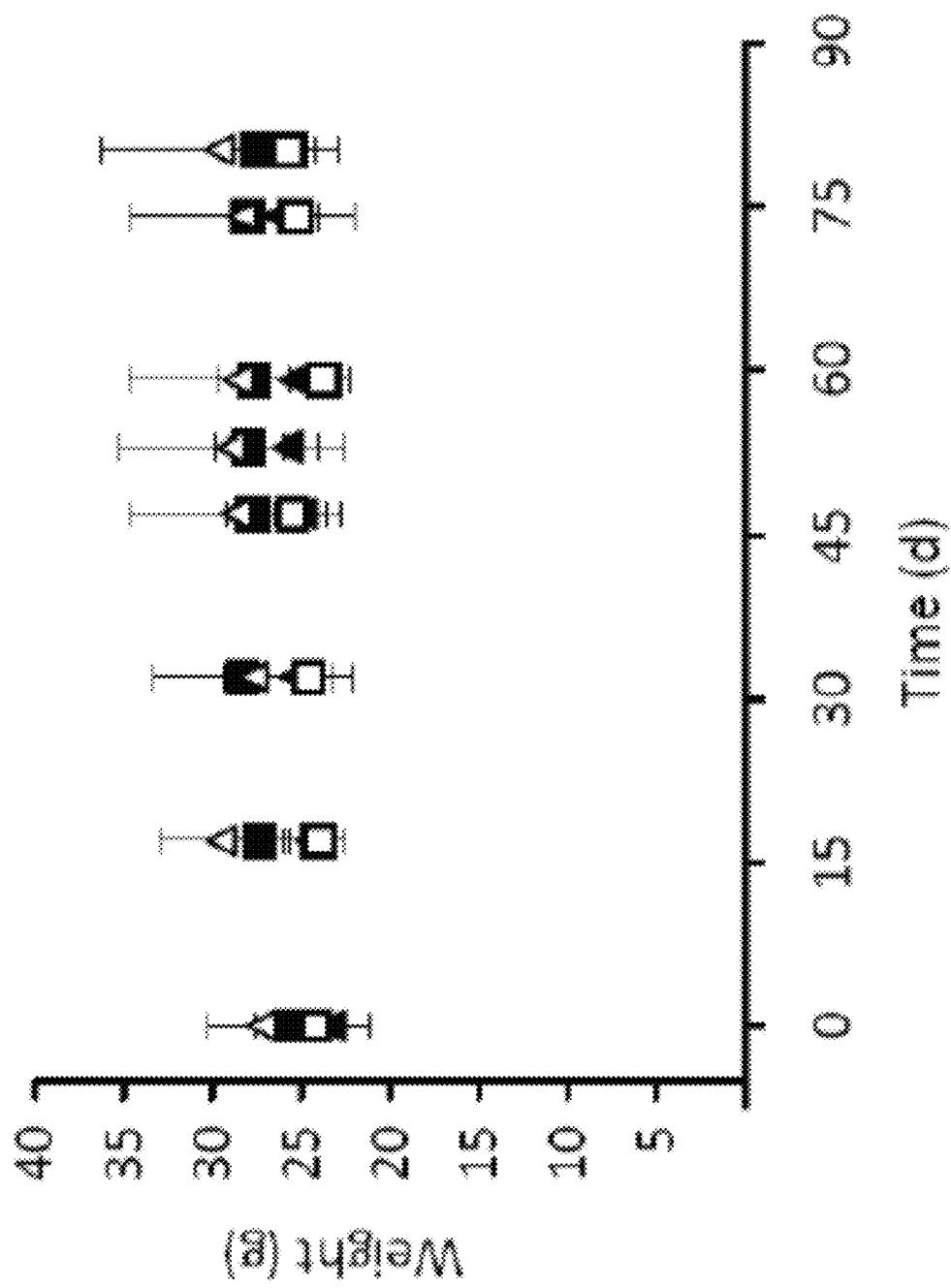

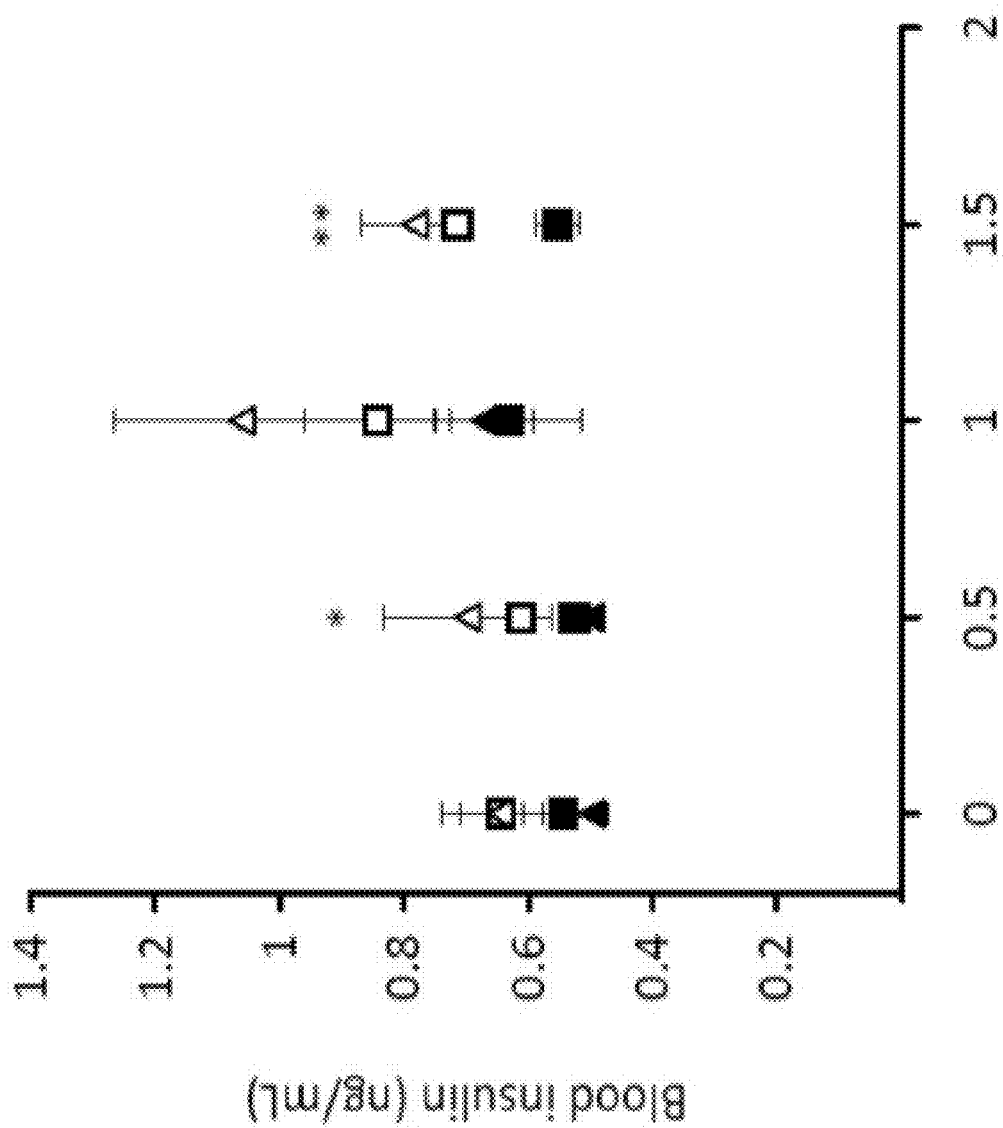

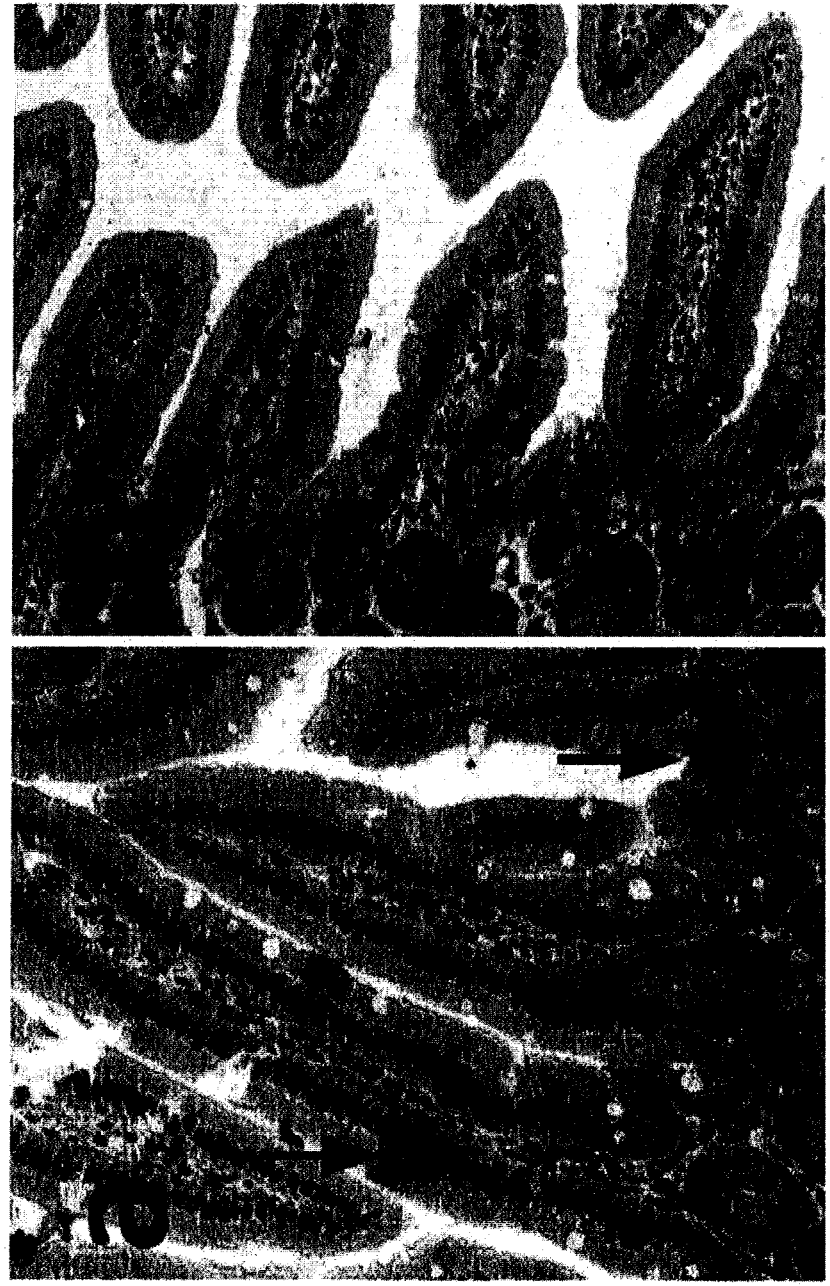
FIGS. 10A-B

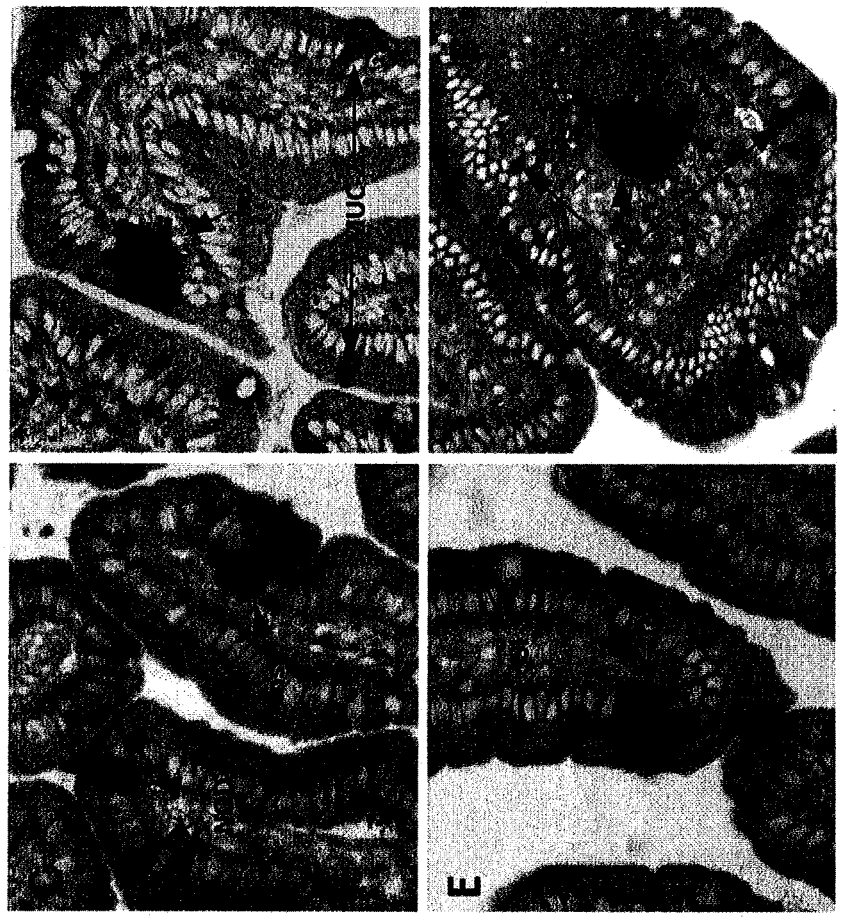
FIGS. 10C-F

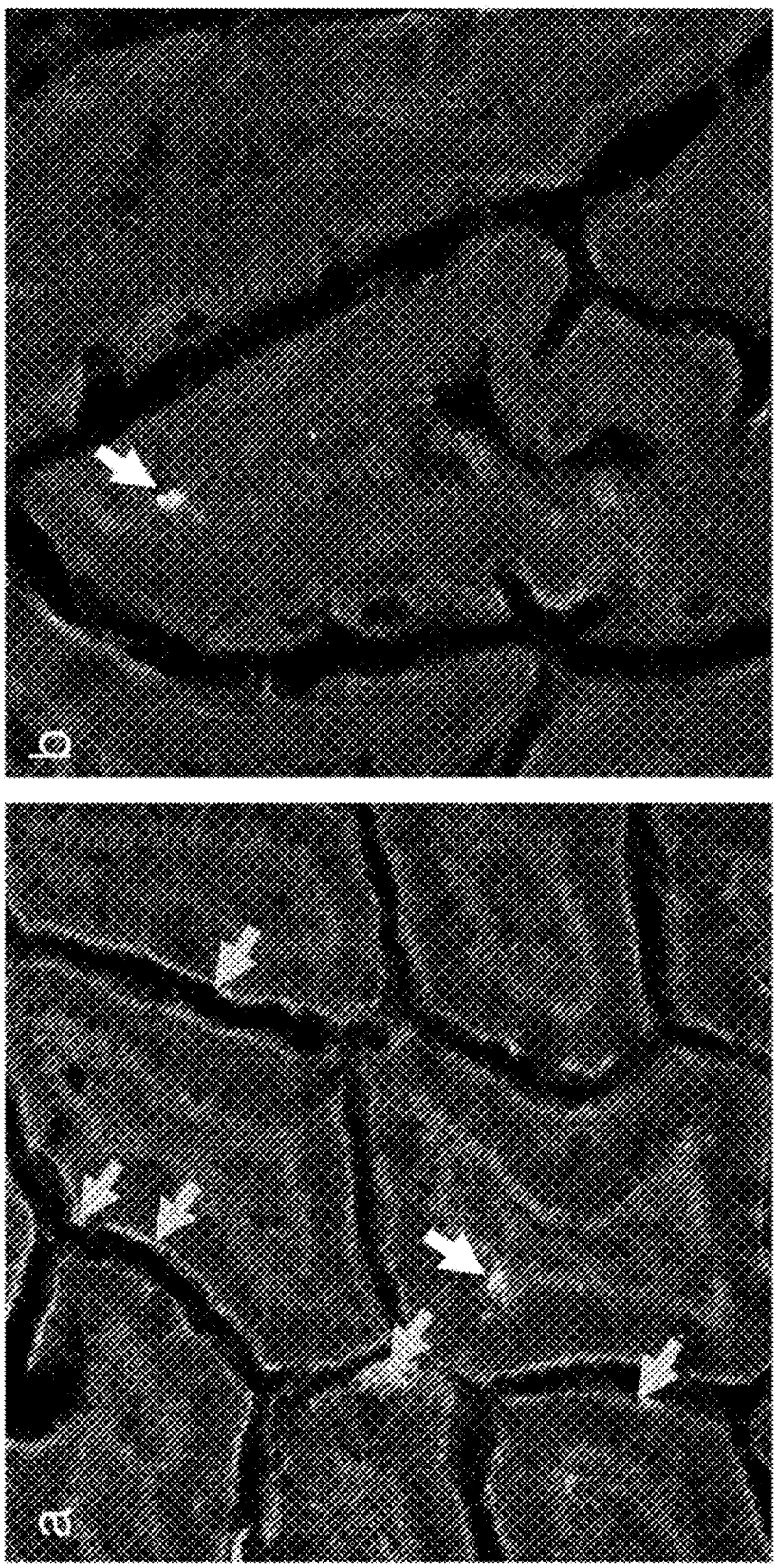
FIGS. 16A-B

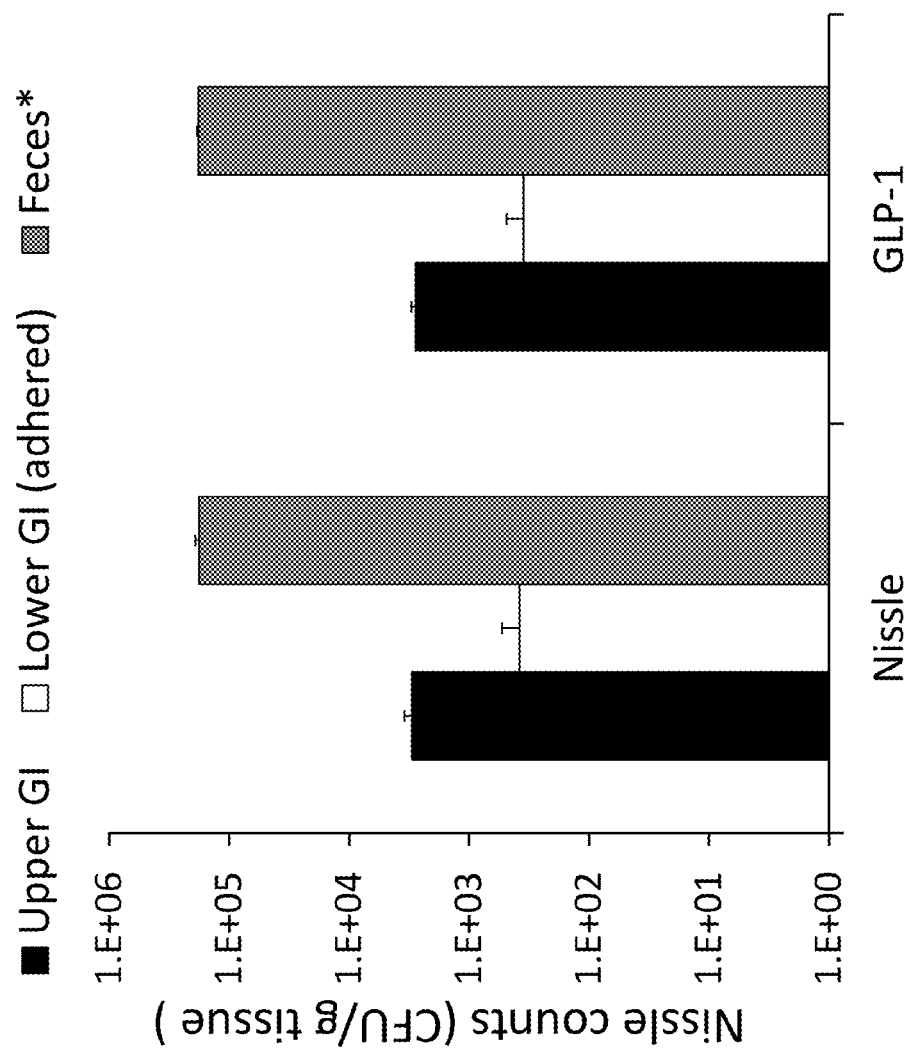

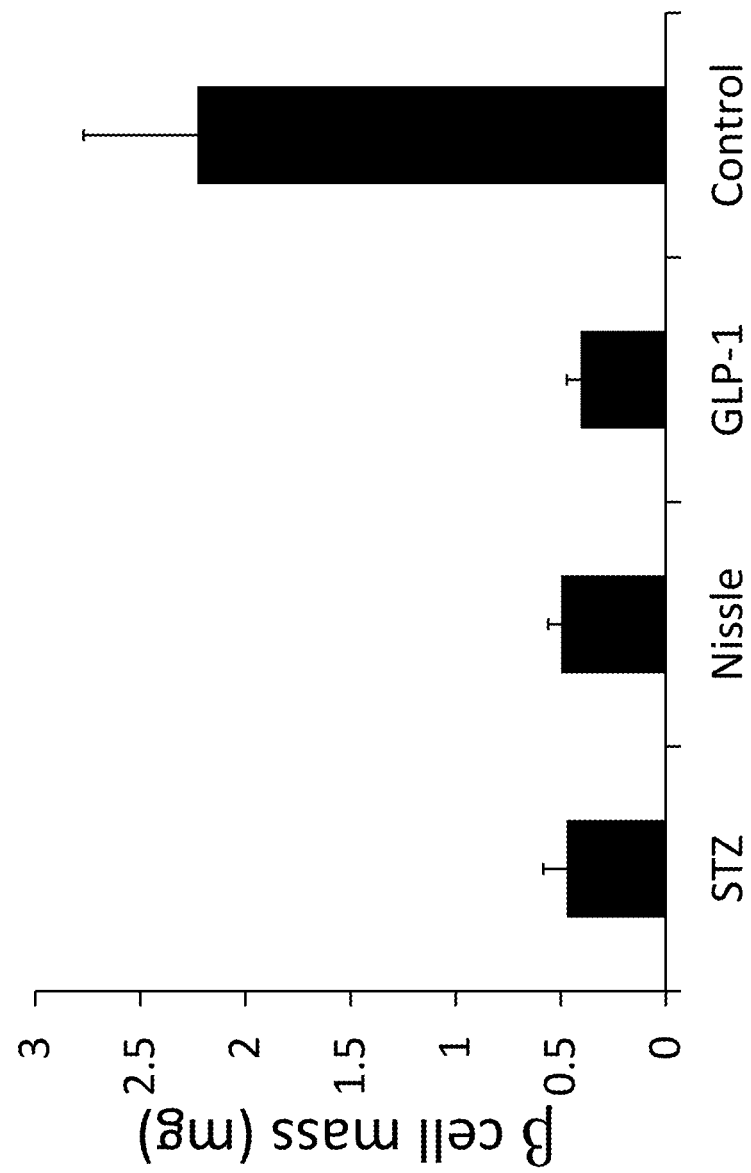

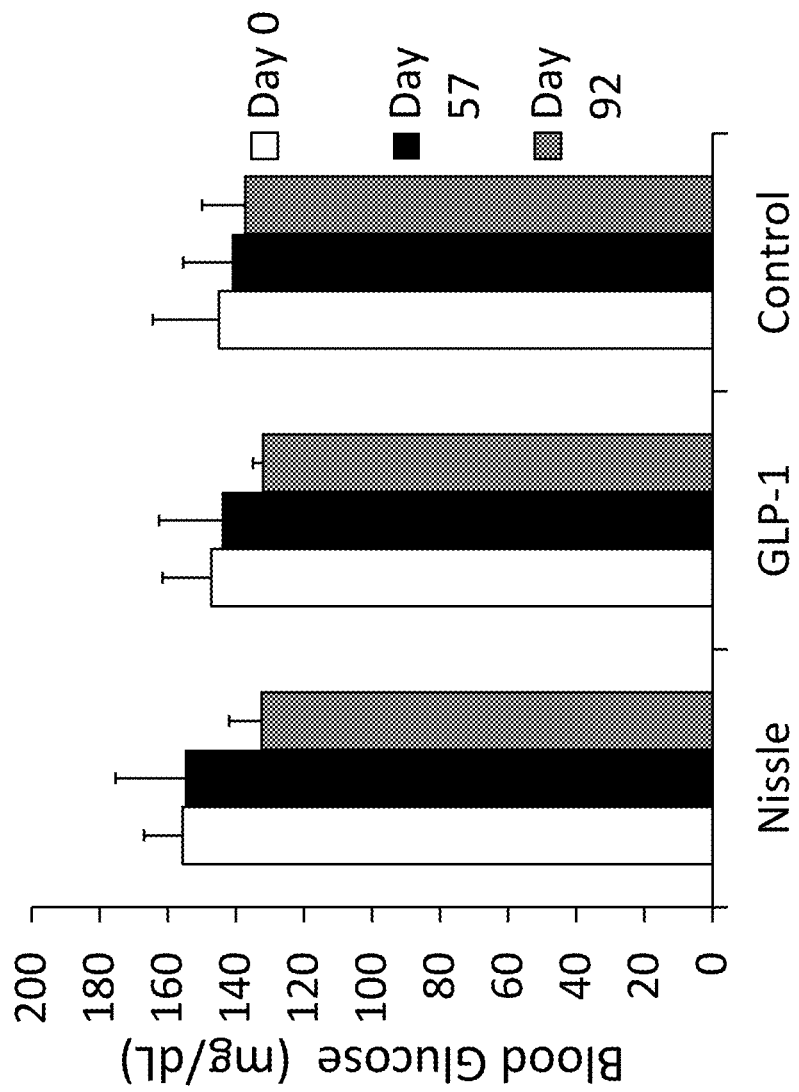

FIGURE 17D
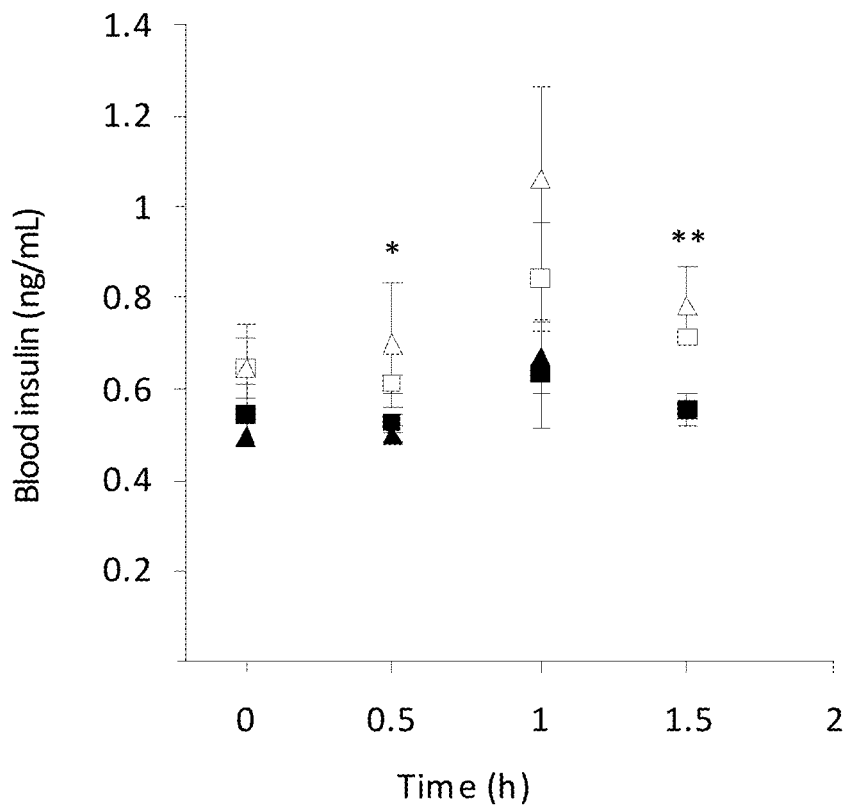
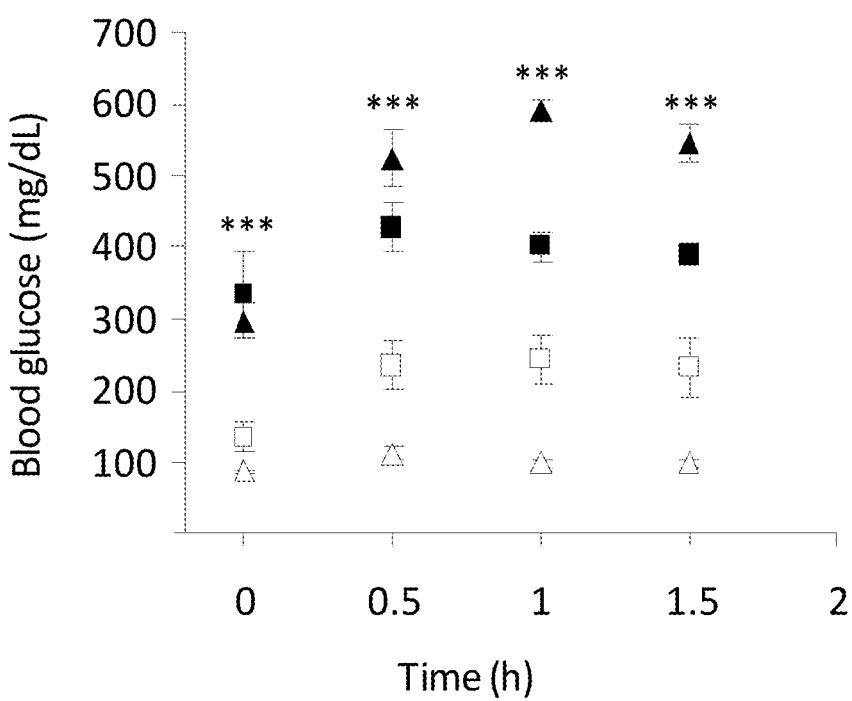

FIGS. 18A-D
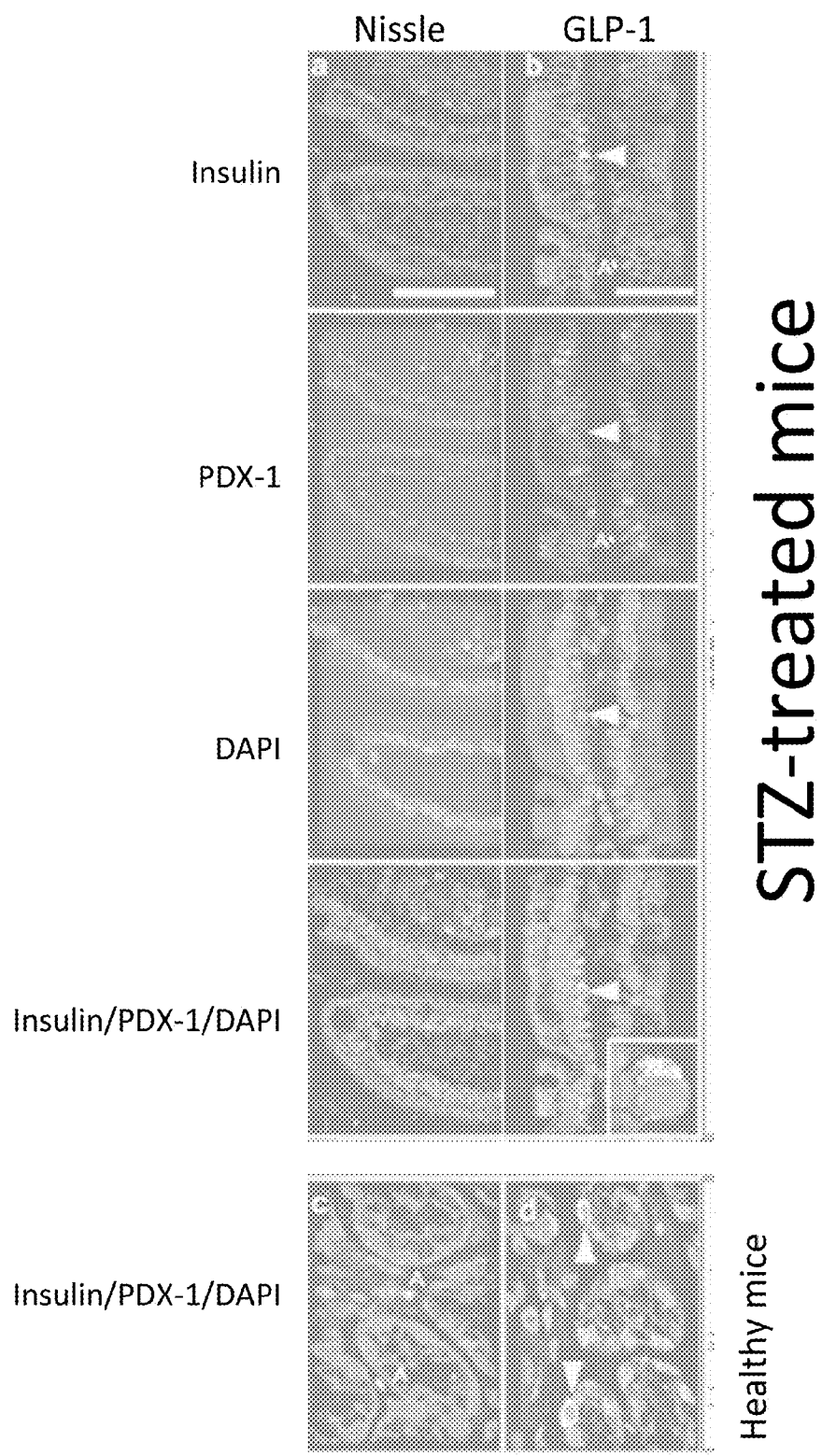

FIGS. 18E-F
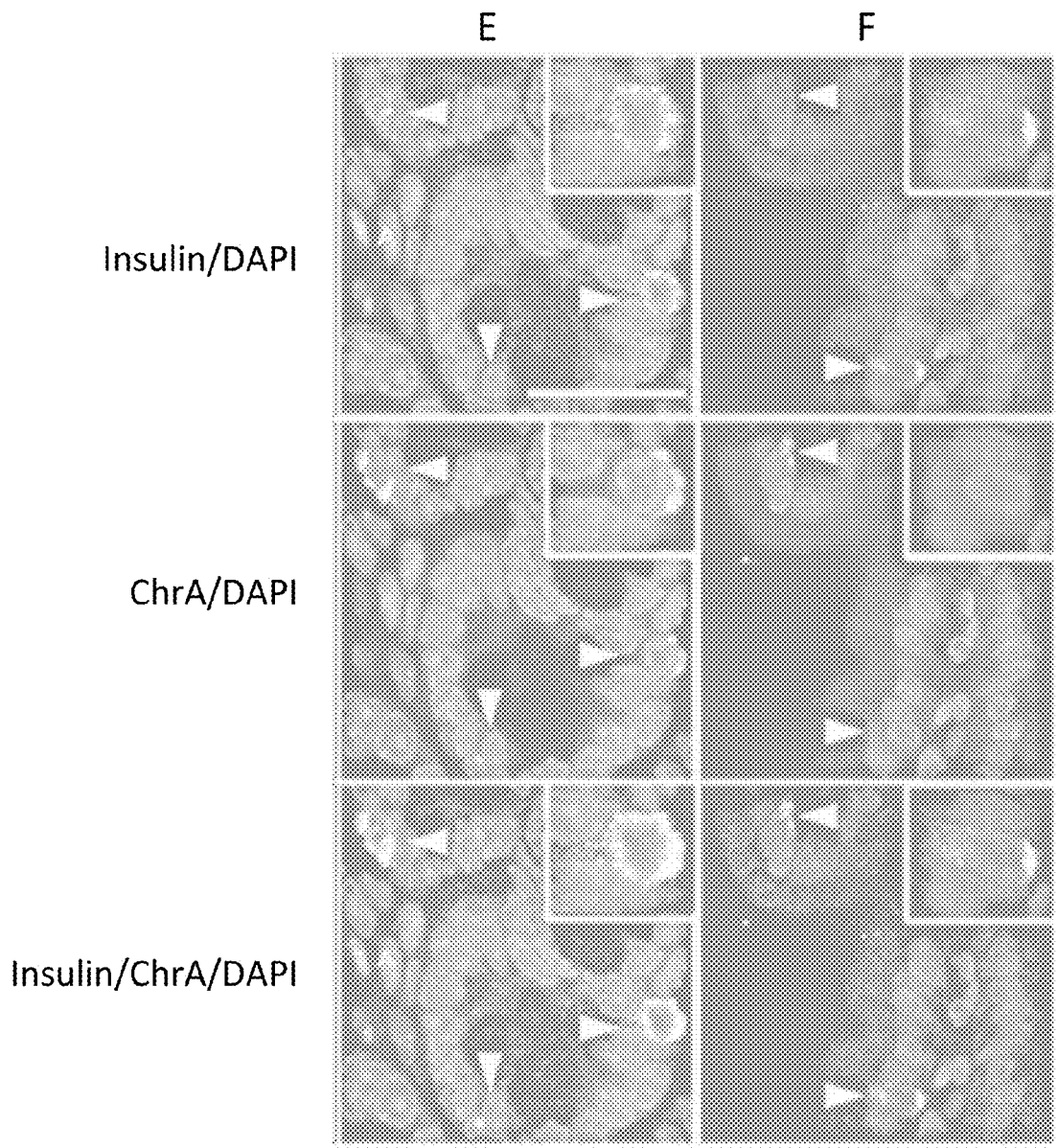

Insulin/SI/DAPI

Insulin/Lys/DAPI

FIGS. 20A-B

COMPOSITIONS AND METHODS FOR TREATING ENDOCRINE, GASTROINTESTINAL OR AUTOIMMUNE DISORDERS

CROSS-REFERENCE TO RELATED APPLICATIONS

This application is a United States National Stage filing under 35 USC §371 of and claims priority to International PCT Application Serial No. PCT/US2011/056174, filed Oct. 13, 2011, which claims priority to U.S. Provisional Application No. 61/393,618, filed Oct. 15, 2010, and U.S. Provisional Application No. 61/539,121, filed Sep. 26, 2011, each of which is incorporated herein by reference in their respective entireties.

STATEMENT REGARDING FEDERALLY SPONSORED RESEARCH OR DEVELOPMENT

Not applicable

1. TECHNICAL FIELD

The invention relates generally to compositions and methods for treating endocrine, gastrointestinal or autoimmune disorders.

2. BACKGROUND OF THE INVENTION

Diabetes mellitus is a disease characterized by hyperglycemia; altered metabolism of lipids, carbohydrates and proteins; and an increased risk of complications from vascular disease. Diabetes is an increasing public health problem, as it is associated with both increasing age and obesity.

There are two major types of diabetes mellitus: 1) Type I, also known as insulin dependent diabetes (IDDM) and 2) Type II, also known as insulin independent or non-insulin dependent diabetes (NIDDM). Both types of diabetes mellitus are due to insufficient amounts of circulating insulin and a decrease in the response of peripheral tissue to insulin.

Type I diabetes results from the body's failure to produce insulin, the hormone that "unlocks" the cells of the body, allowing glucose to enter and fuel them. The complications of Type I diabetes include heart disease and stroke; retinopathy (eye disease); kidney disease (nephropathy); neuropathy (nerve damage); as well as maintenance of good skin, foot and oral health.

Type II diabetes results from the body's inability to either produce enough insulin or the cells inability to use the insulin that is naturally produced by the body. The condition where the body is not able to optimally use insulin is called insulin resistance. Type II diabetes is often accompanied by high blood pressure and this may contribute to heart disease. In patients with type II diabetes mellitus, stress, infection, and medications such as corticosteroids) can also lead to severely elevated blood sugar levels. Accompanied by dehydration, severe blood sugar elevation in patients with type II diabetes can lead to an increase in blood osmolality (hyperosmolar state). This condition can lead to coma.

Insulin lowers the concentration of glucose in the blood by stimulating the uptake and metabolism of glucose by muscle and adipose tissue. Insulin stimulates the storage of glucose in the liver as glycogen, and in adipose tissue as triglycerides. Insulin also promotes the utilization of glucose in muscle for energy. Thus, insufficient insulin levels in the blood, or decreased sensitivity to insulin, gives rise to excessively high levels of glucose and triglycerides in the blood.

The early symptoms of untreated diabetes mellitus are related to elevated blood sugar levels, and loss of glucose in the urine. High amounts of glucose in the urine can cause increased urine output and lead to dehydration. Dehydration causes increased thirst and water consumption. The inability to utilize glucose energy eventually leads to weight loss despite an increase in appetite. Some untreated diabetes patients also complain of fatigue, nausea, and vomiting. Patients with diabetes are prone to developing infections of the bladder, skin, and vaginal areas. Fluctuations in blood glucose levels can lead to blurred vision. Extremely elevated glucose levels can lead to lethargy and coma (diabetic coma).

People with glucose levels between normal and diabetic have impaired glucose tolerance (IGT). This condition is also called pre-diabetes or insulin resistance syndrome. People with IGT do not have diabetes, but rather have blood glucose levels that are higher than normal but not yet high enough to be diagnosed as diabetes. Their bodies make more and more insulin, but because the tissues don't respond to it, their bodies can't use sugar properly. Recent studies have shown that IGT itself may be a risk factor for the development of heart disease. It is estimated that people with pre-diabetes have a 1.5-fold risk of cardiovascular disease compared to people with normal blood glucose. People with diabetes have a 2- to 4-fold increased risk of cardiovascular disease.

High blood levels of glucose and triglycerides cause the thickening of capillary basement membrane, which results in the progressive narrowing of vessel lumina. The vasculopathologies give rise to conditions such as diabetic retinopathy, which may result in blindness, coronary heart disease, intercapillary glomerulosclerosis, neuropathy, and ulceration and gangrene of the extremities.

The toxic effects of excess plasma levels of glucose include the glycosylation of cells and tissues. Glycosylated products accumulate in tissues and may eventually form cross-linked proteins, which cross-linked proteins are termed advanced glycosylation end products. It is possible that non-enzymatic glycosylation is directly responsible for expansion of the vascular matrix and vascular complications of diabetes. For example, glycosylation of collagen results in excessive cross-linking, resulting in atherosclerotic vessels. Also, the uptake of glycosylated proteins by macrophages stimulates the secretion of pro-inflammatory cytokines by these cells. The cytokines activate or induce degradative and proliferative cascades in mesenchymal and endothelial cells respectively.

The glycosylation of hemoglobin provides a convenient method to determine an integrated index of the glycemic state. The level of glycosylated proteins reflects the level of glucose over a period of time and is the basis of an assay referred to as the hemoglobin A1 (HbA1c) assay.

HbA1c reflects a weighted average of blood glucose levels during the previous 120 days; plasma glucose in the previous 30 days contributes about 50% to the final result in an HbA1c assay. The test for A1c (also known as HbA1c, glycohemoglobin, or glycated hemoglobin) indicates how well diabetes has been controlled over the last few months. The closer A1c is to 6%, the better the control of diabetes. For every 30 mg/dl increase in A1c blood glucose, there is a 1% increase in A1c, and the risk of complications increases.

Another explanation for the toxic effects of hyperglycemia includes sorbitol formation. Intracellular glucose is reduced to its corresponding sugar alcohol, sorbitol, by the enzyme aldose reductase; the rate of production of sorbitol is determined by the ambient glucose concentration. Thus, tissues such as lens, retina, arterial wall and Schwann cells of peripheral nerves have high concentrations of sorbitol.

Hyperglycemia also impairs the function of neural tissues because glucose competes with myoinositol resulting in reduction of cellular concentrations and, consequently, altered nerve function and neuropathy.

Increased triglyceride levels are also a consequence of insulin deficiency. High triglyceride levels are also associated with vascular disease.

Thus, controlling blood glucose and triglyceride levels is a desirable therapeutic goal. A number of oral antihyperglycemic agents are known. Medications that increase the insulin output by the pancreas include sulfonylureas (including chlorpropamide [Orinase®], tolbutamide [Tolinase®], glyburide [Micronase®], glipizide [Glucotrol®], and glimepiride [Amaryl®]) and meglitinides (including reparglinide [Prandin®] and nateglinide [Starlix®]). Medications that decrease the amount of glucose produced by the liver include biguanides (including metformin [Glucophage®]). Medications that increase the sensitivity of cells to insulin include thazolidinediones (including troglitazone [Resulin®], pioglitazone [Actos®] and rosiglitazone [Avandia®]). Medications that decrease the absorption of carbohydrates from the intestine include alpha glucosidase inhibitors (including acarbose [Precose®] and miglitol [Glyset®]). Pioglitazone and rosiglitazone can change the cholesterol patterns in diabetics. HDL (or good cholesterol) increases on these medications. Acarbose works on the intestine; its effects are additive to diabetic medications that work at other sites, such as sulfonylureas. ACE inhibitors can be used to control high blood pressure, treat heart failure, and prevent kidney damage in people with hypertension or diabetes. ACE inhibitors or combination products of an ACE inhibitor and a diuretic, such as hydrochlorothazide, are marketed. However, none of these treatments is ideal because they pose short term treatments with many side-effects.

Blood pressure control can reduce cardiovascular disease (for example, myocardial infarction and stroke) by approximately 33% to 50% and can reduce microvascular disease (eye, kidney, and nerve disease) by approximately 33%. The Center for Disease Control has found that for every 10 millimeters of mercury (mm Hg) reduction in systolic blood pressure, the risk for any complication related to diabetes is reduced by 12%. Improved control of cholesterol and lipids (for example HDL, LDL, and triglycerides) can reduce cardiovascular complications by 20% to 50%.

In a healthy human, total cholesterol should be less than 200 mg/dl. Target levels for high density lipoprotein (HDL or "good" cholesterol) are above 45 mg/dl for men and above 55 mg/dl for women, while low density lipoprotein (LDL or "bad" cholesterol) should be kept below 100 mg/dl. Target triglyceride levels for women and men are less than 150 mg/dl.

Approximately 50% of patients with diabetes develop some degree of diabetic retinopathy after 10 years of diabetes, and 80% of diabetics have retinopathy after 15 years.

In a study (the DCCT study) conducted by the National Institute of Diabetes and Digestive and Kidney Diseases (NIDDK) it was shown that keeping blood glucose levels as close to normal as possible slows the onset and progression of eye, kidney, and nerve diseases caused by diabetes.

In the Diabetes Prevention Program (DPP) clinical trial type 2 diabetics were studied. The DPP study found that over the 3 years of the study, diet and exercise sharply reduced the chances that a person with IGT would develop diabetes. Administration of metformin (Glucophage®) also reduced risk, although less dramatically.

The DCCT study showed a correlation between HbA1c and the mean blood glucose. The DPP study showed that HbA1c is strongly correlated with adverse outcome risk.

In a series of reports from the American Heart Association's Prevention Conference VI: Diabetes and Cardiovascular Disease it was reported that about two-thirds of people with diabetes eventually die of heart or blood vessel disease. Studies also showed that the increase in cardiovascular disease risk associated with diabetes can be lessened by controlling individual risk factors such as obesity, high cholesterol, and high blood pressure.

It is important for a person suffering from diabetes to reduce the risk of complications such as cardiovascular disease, retinopathy, nephropathy, and neuropathy. It is also important for diabetics to reduce total cholesterol and triglyceride levels to reduce cardiovascular complications. Reduction of these possible complication risks is also important for a person suffering from IGT (a pre-diabetic).

Thus, if blood glucose levels can be controlled, the risk of complications such as cardiovascular disease, retinopathy, nephropathy, and neuropathy can be reduced or their onset delayed. If total cholesterol and triglyceride levels can be reduced, then cardiovascular complications can be reduced.

Citation or identification of any reference in Section 2, or in any other section of this application, shall not be considered an admission that such reference is available as prior art to the present invention.

3. SUMMARY OF THE INVENTION

A recombinant cell is provided. In one embodiment, the recombinant cell comprises a signal sequence and a promoter, wherein:

a. the signal sequence regulates signal-dependent expression of a target nucleic acid in a host;

b. the recombinant cell is derived from an enteric bacterium or a commensal bacterium, and c. the signal sequence is GLP-2, fragments thereof, or analogs thereof or combinations thereof.

In another embodiment, the recombinant cell comprises a signal sequence and a promoter, wherein:

a. the signal sequence regulates signal-dependent expression of a target nucleic acid in a host, b. the recombinant cell is derived from an enteric bacterium or a commensal bacterium, and c. the target nucleic acid encodes a mammalian factor that is capable of reprogramming a first cell of the host into a second cell.

In another embodiment, the host is a mammal.

In another embodiment, the second cell is a β-like cell, a thyroid cell, a hepatocyte or an immunoresponsive cell.

In another embodiment, the first cell of the host is an intestinal epithelial cell.

In another embodiment, the second cell is a glucose responsive insulin secreting cell.

In another embodiment, the signal sequence regulates signal-dependent expression of a target nucleic acid in response to an environmental stimulus.

In another embodiment, the promoter is a glucose-responsive promoter.

In another embodiment, the promoter can be any inducible or constitutive promoter known in the art.

In another embodiment, the signal sequence is selected from the group consisting of GLP-1, GIP, PDX-1, one or more fragments thereof, analogs thereof, and combinations thereof.

In another embodiment, the signal sequence is selected from the group consisting of GLP-1, PDX-1, GIP, GLP-2, insulin, growth hormone, prolactin, calcitonin, luteinising hormone, parathyroid hormone, somatostatin, thyroid stimulating hormone, vasoactive intestinal polypeptide, trefoil factors, cell and tissue repair factors, transforming growth factor β, keratinocyte growth factor, a structural group 1 cytokine adopting an antiparallel 4α helical bundle structure, IL-2, IL-3, IL-4, IL-5, IL-6, IL-7, IL-9, IL-10, IL-11, IL-12, IL-13, GM-CSF, M-CSF, SCF, IFN-γ, EPO, G-CSF, LIF, OSM, CNTF, GH, PRL, IFNα/β, a structural group 2 cytokine, a TNF-family cytokine, TNFα, TNFβ, CD40, CD27, FAS ligands, an IL-1-family cytokine, a fibroblast growth factor, a platelet derived growth factor, transforming growth factor p, a nerve growth factor, a structural group 3 cytokine comprising a short chain α/β molecule, an epidermal growth factor-family cytokine, a C—C or C—X—C chemokine, an insulin-related cytokine, a structural group 4 cytokine, a heregulins, a neuregulins, EGF, immunoglobulin-like domain, kringle domain, one or more fragments thereof, analogs thereof, and combinations thereof In another embodiment, the signal sequence and the promoter are encoded on a plasmid in the recombinant cell.

In another embodiment, the cell is derived from a probiotic bacterium.

In another embodiment, the cell is a bacterium selected from the group consisting of *Escherichia, Pseudomonas, Bacteroides, Lactobacillus, Lactococcus, Bacillus, Proteus, Bifidobacterium, Streptococcus, Staphylococcus*, and *Corynebacterium*.

In another embodiment, the target nucleic acid encodes a mammalian factor that is capable of promoting desired functioning of a physiological process in the host, or is capable of treating a non-infectious disease in the host.

In another embodiment, the non-infectious disease is selected from the group consisting of an autoimmune disease, cancer, endocrine disease, gastrointestinal, cancer and a combination thereof.

In another embodiment, the non-infectious disease is diabetes

In another embodiment, the diabetes is type 1 diabetes, type 2 diabetes or Metabolic Syndrome.

In another embodiment, the non-infectious disease is selected from the group consisting of Crohn's disease, obesity, phenylketonuria, maple syrup urine disease, histidinemia, hyperglycemia, diabetic retinopathy, coronary heart disease, intercapillary glomerulosclerosis, nephropathy, neuropathy, ulceration or gangrene of the extremities, atherosclerosis, hypercholesterolemia, high blood pressure, hyperproteinemia, proteinuria, osteoporosis, anemia, hyperlipoproteinemia, ketoacidosis, hypertriglyceridemia, lactic acidosis, cardiomyopathy, Wilson's disease, leukodystrophy, fucosidosis, cancer, chemotherapy-induced diarrhea, inflammatory bowel disease, ventricular and atrial fibrillation, post-surgical organ failure, irritable bowel syndrome, interstitial cystitis/bladder pain syndrome, short bowel syndrome, ulcerative colitis, and a combination thereof.

In another embodiment, the cancer is gastrointestinal cancer, stomach cancer, gallbladder cancer, gastrointestinal stromal tumors, liver cancer, pancreatic cancer, or colon cancer.

In another embodiment, the mammalian factor promotes the desired functioning of the physiological process after intestinal injury or surgery.

In another embodiment, the recombinant cell is capable of reaching intestinal villi without being absorbed into a systemic circulation of the host.

In another embodiment, the promoter is an inducible or constitutive promoter.

In another embodiment, the promoter is a fliC promoter.

In another embodiment, the recombinant cell further comprises a secretion tag

In another embodiment, the secretion tag is a fliC secretion tag.

In another embodiment, the secretion tag is an alpha-hemolysin (HlyA) secretion tag In another embodiment, the recombinant cell further comprises a cell-penetrating peptide (CPP) sequence.

In another embodiment, the recombinant cell expresses the signal sequence as a fusion protein, wherein the fusion protein comprises a signal encoded by the signal sequence and a cell-penetrating peptide encoded by the cell penetrating peptide sequence.

A method for treating diabetes in a host is also provided, the method comprising the step of administering to the host a recombinant cell, wherein the recombinant cell comprises a signal sequence and a promoter, and wherein:

a. the signal sequence regulates signal-dependent expression of a target nucleic acid in a host, b. the recombinant cell is derived from an enteric bacterium or a commensal bacterium, and c. the target nucleic acid encodes a mammalian factor that is capable of reprogramming a first cell of the host into a second cell.

In one embodiment, the target signal sequence stimulates expression of a disease-preventing factor or inhibits expression of a causal factor of diabetes.

In another embodiment, the diabetes is type 1 diabetes, type 2 diabetes or Metabolic Syndrome.

In another embodiment, the signal sequence regulates signal-dependent expression of a target nucleic acid in response to an environmental stimulus.

In another embodiment, the environmental stimulus is glucose.

In another embodiment, the disease-preventing factor comprises insulin.

In another embodiment, the target nucleic acid encodes a mammalian factor that promotes decreasing blood glucose levels in the host.

In another embodiment, the target nucleic acid encodes a mammalian factor that promotes increasing blood insulin levels in the host.

A method for differentiating an intestinal cell into another cell type in a mammalian host, the method comprising the step of administering to the host a recombinant cell, wherein the recombinant cell comprises a signal sequence and a promoter, and wherein:

a. the signal sequence regulates signal-dependent expression of a target nucleic acid in a host, b. the recombinant cell is derived from an enteric bacterium or a commensal bacterium, and c. the target nucleic acid encodes a mammalian factor that is capable of reprogramming a first cell of the host into a second cell.

In another embodiment, the another cell type is a β-like cell, a thyroid cell, a hepatocyte or an immunoresponsive cell.

In another embodiment, the β-like cell is a glucose-responsive cell.

In another embodiment, an effective amount of the recombinant cell is administered.

In another embodiment, the effective amount of the recombinant cell is at least about $10^4$ CFU/kg.

In another embodiment, the recombinant cell is administered in combination with a compound having a synergistic effect.

In another embodiment, the compound having the synergistic effect is selected from the group consisting of DPP-4 inhibitors, GLP-2, GLP-1 agonists, dimethyl sulfoxide, insulin, alpha-glucosidase inhibitors, pramlintide, meglitinides, repaglinide, nateglinide, chlorpropamide, metformin, sulfonylurea, glipizide, glyburide, glimepiride, thiazolidinediones, analogs thereof, fragments thereof, and combinations thereof.

In another embodiment, the signal sequence is selected from the group consisting of GLP-1, PDX-1, GIP, GLP-2, insulin, growth hormone, prolactin, calcitonin, luteinising hormone, parathyroid hormone, somatostatin, thyroid stimulating hormone, vasoactive intestinal polypeptide, trefoil factors, cell and tissue repair factors, transforming growth factor β, keratinocyte growth factor, a structural group 1 cytokine adopting an antiparallel 4α helical bundle structure, IL-2, IL-3, IL-4, IL-5, IL-6, IL-7, IL-9, IL-10, IL-11, IL-12, IL-13, GM-CSF, M-CSF, SCF, IFN-γ, EPO, G-CSF, LIF, OSM, CNTF, GH, PRL, IFNα/β, a structural group 2 cytokine, a TNF-family cytokine, TNFα, TNFβ, CD40, CD27, FAS ligands, an IL-1-family cytokine, a fibroblast growth factor, a platelet derived growth factor, transforming growth factor p, a nerve growth factor, a structural group 3 cytokine comprising a short chain α/β molecule, an epidermal growth factor-family cytokine, a C—C or C—X—C chemokine, an insulin-related cytokine, a structural group 4 cytokine, a heregulins, a neuregulins, EGF, immunoglobulin-like domain, kringle domain, one or more fragments thereof, analogs thereof, and combinations thereof.

In another embodiment, the signal sequence is GIP, GLP-1, GLP-2, PDX-1, fragments thereof, analogs thereof, and combinations thereof.

A method for reprogramming an intestinal cell in a host into a glucose-responsive insulin secreting cell is also provided, the method comprising the step of administering a recombinant cell comprising a signal sequence and a promoter, wherein the signal sequence is selected from the group consisting of GLP-1, GIP, PDX-1, fragments thereof, analogs thereof and combinations thereof.

In one embodiment, the host is hyperglycemic and administering the recombinant cell to the hyperglycemic host reduces or eliminates a need for therapeutic administration of exogenous insulin into the host.

4. BRIEF DESCRIPTION OF THE DRAWINGS

The present invention is described herein with reference to the accompanying drawings, in which similar reference characters denote similar elements throughout the several views. It is to be understood that in some instances, various aspects of the invention may be shown exaggerated or enlarged to facilitate an understanding of the invention.

FIG. 1 illustrates plasmids made for study. To study the P0/P1 promoters from *E. coli* DH5α, two plasmids were made (pFD1 and pFD2). pFD1 encoded the entire P0/P1 region to drive the expression of enhanced green fluorescent protein (EGFP). pFD2 encoded only the P0 region of the promoter upstream from EGFP. To test the efficacy of insulinotropic protein secretion from recombinant bacteria for stimulating insulin secretion in Caco-2 cells, plasmids pFD-PDX, pFD-GLP, and pFD-20 were constructed.

FIG. 2 illustrates P0 and P0/P1 response to glucose. EGFP expression was used to measure the response of the P0 and/or P1 promoter to different media conditions. P0=P0 only; P0+P1=P0 plus P1 flanking region; DH5α=lac operon control.

Figure 4A:
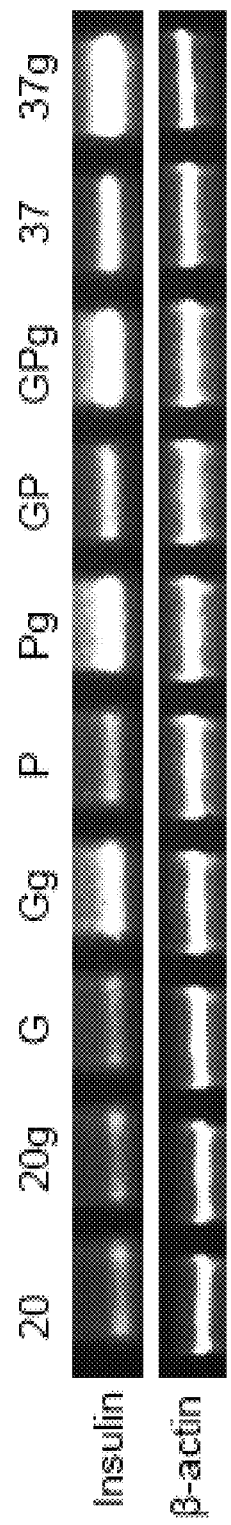
FIG. 4A illustrates the reverse transcription-PCR of Caco-2 cells incubated with cell-free media (CFM) from overnight cultures of *E. coli* Nissle expressing GLP-1 (G), PDX-1-CPP (P), both GLP-1 and PDX-1-CPP (GP), or a control plasmid (samples denoted "20") or with synthesized GLP-1 (amino acids 1 to 37; samples denoted "37") and subsequent stimulation with either glucose ("g") or glycerol.
Figure 4B:
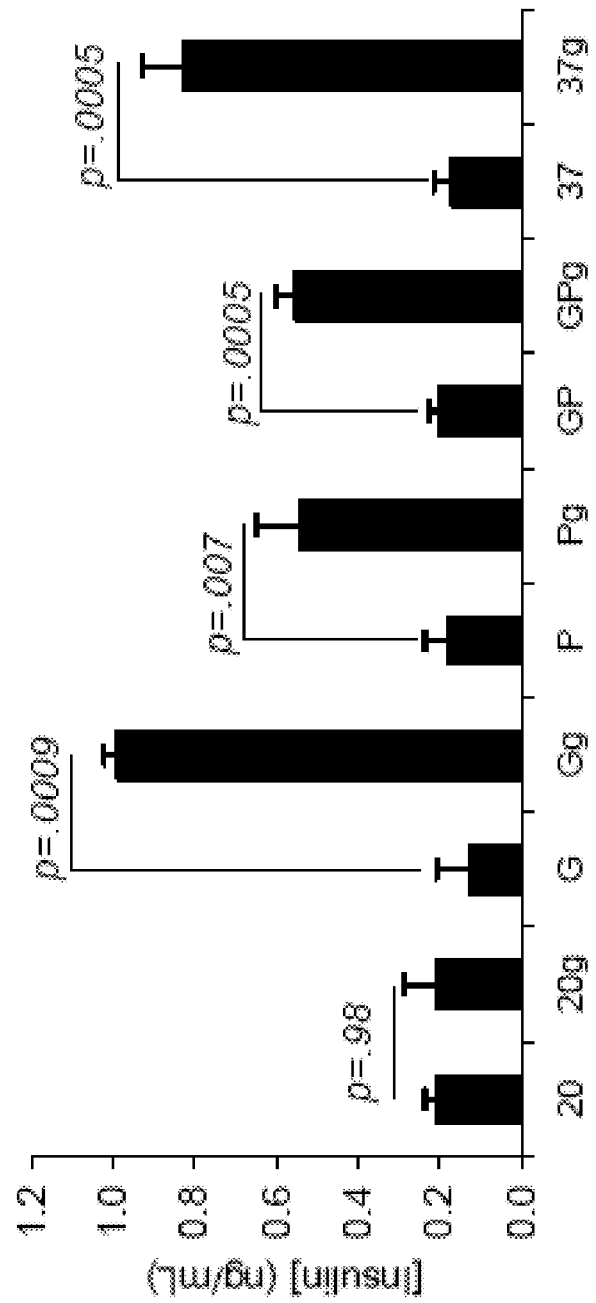

FIG. 4B illustrates the enzyme-linked immunosorbent assay of insulin secretion by stimulated Caco-2 cells. Error bars represent 1 standard deviation for at least three experiments. P values are from a Student t test (n=3).

Figure 5:
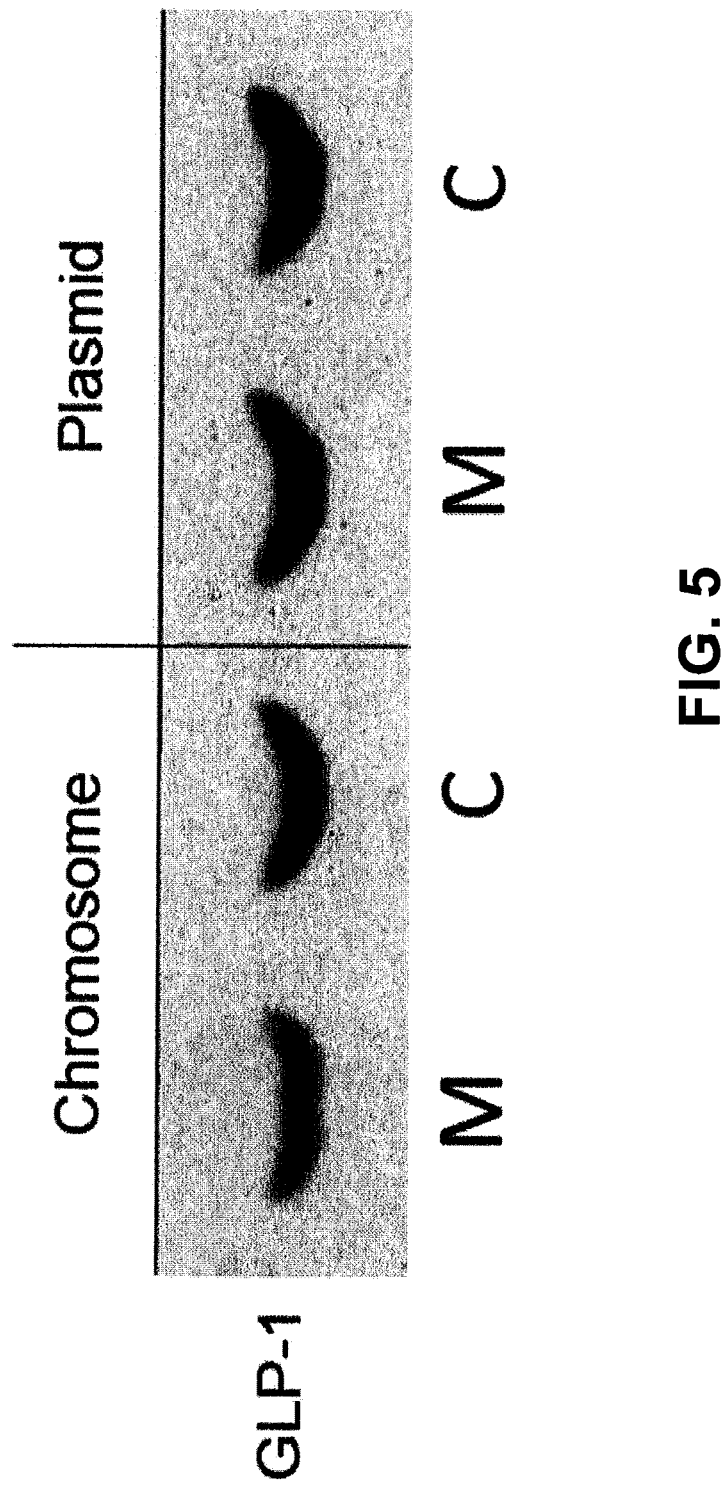

FIG. 5 illustrates a comparison of the secretion of GLP-1 from Nissle engineered to secrete GLP-1 with a fliC promoter and secretion tag to secretion of GLP-1 from a plasmid-bearing strain containing the same sequence without the pKD3 chromosomal insertion cassette.

Figure 6:
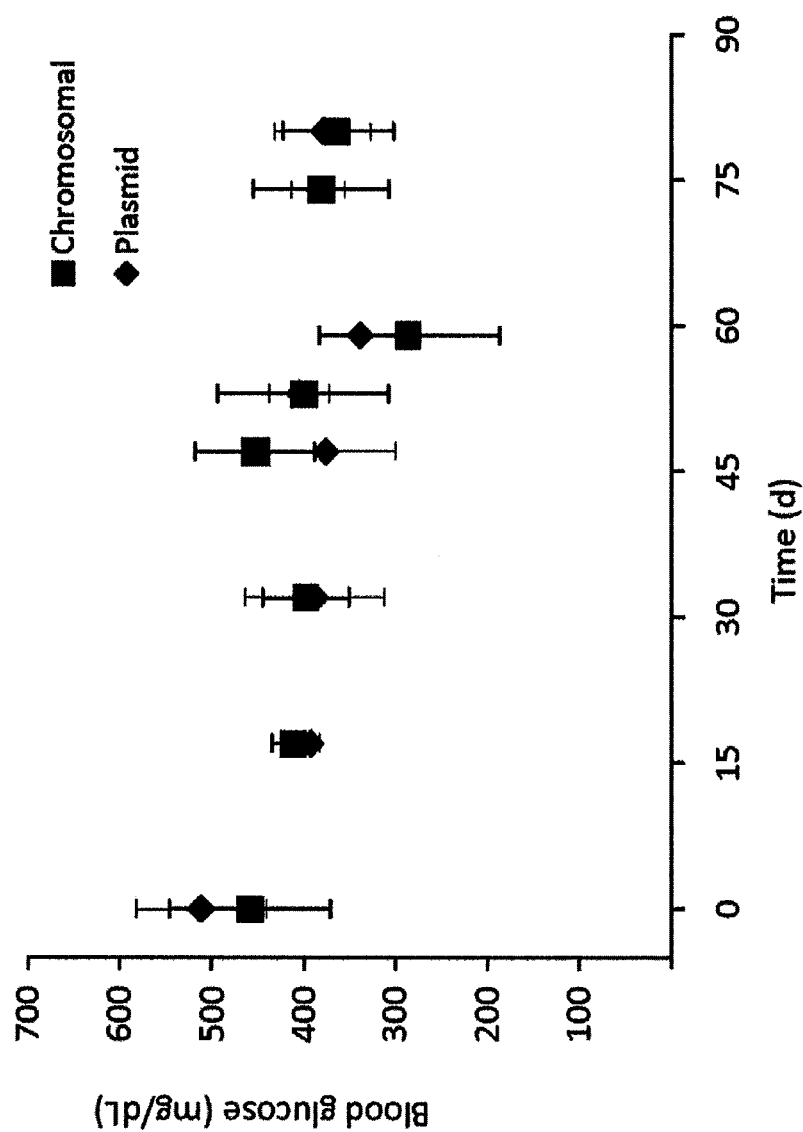

FIG. 6 illustrates in vivo testing of glucose levels between mice treated with Nissle engineered to secrete GLP-1 with a fliC promoter and secretion tag to secretion of GLP-1 from a plasmid-bearing strain containing the same sequence without the pKD3 chromosomal insertion cassette.

Figure 7:
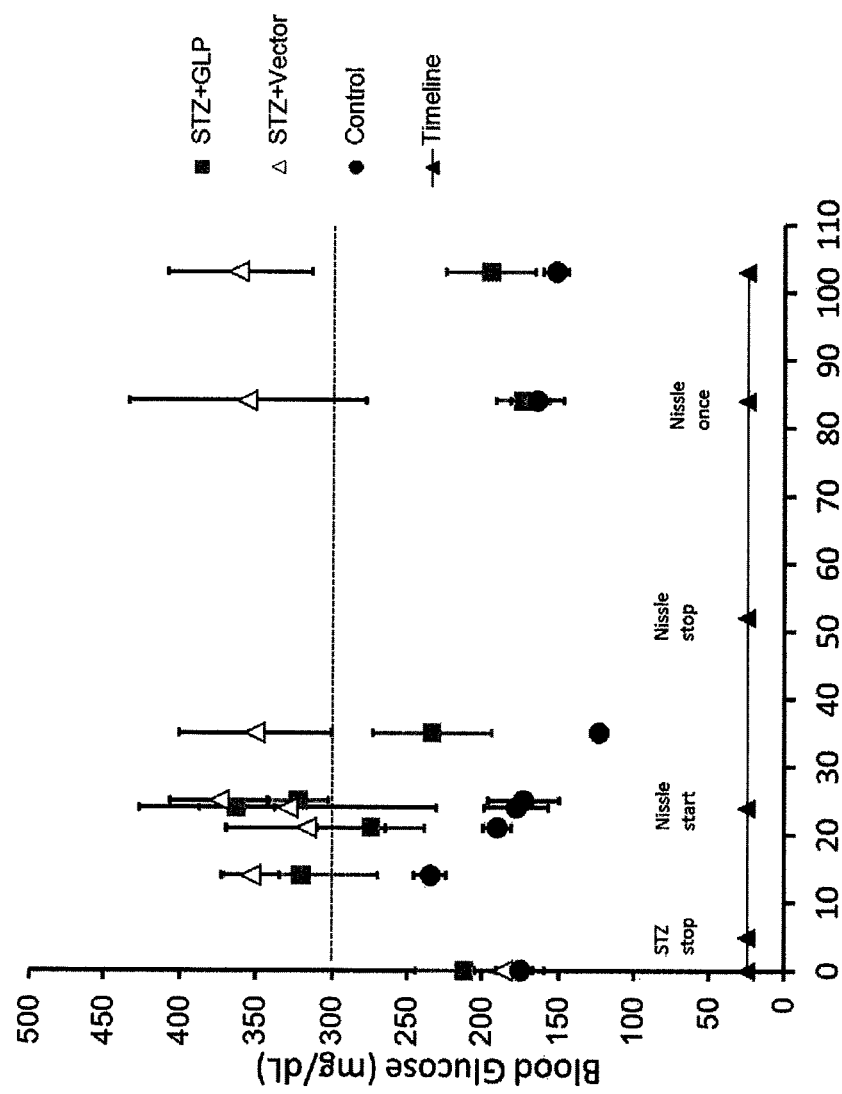

FIG. 7 illustrates the reduction of blood glucose levels in a murine model of type-1 diabetes.

FIGS. 8A-B illustrates the immunohistochemistry of mouse intestinal sections showing insulin. Diabetic mice fed with *E. coli* Nissle 1917 expressing GLP-1 (A) and with *E. coli* Nissle 1917 expressing a random peptide (B) were sacrificed at the end of the experiments described in Section 6.5, Example 5. Intestinal sections were stained (red) for the presence of insulin. High concentrations of insulin are noted by arrows in A.

FIGS. 9A-E illustrate measurements of the mouse after treatment with either Nissle-GLP-1, Nissle or given no treatment. β cell mass was measured (A). Mouse random glucose levels (B) and weights (C) were monitored over 80 days. Blood insulin were measured every 30 minutes for 1.5 hours post-glucose injection (D) and blood glucose were measured every 30 minutes for 1.5 hours post-glucose injection (E).

FIGS. 10A-F illustrates the relative frequency of pockets of insulin containing cell in mouse intestines. Immuno-staining of mouse intestines revealed insulin-containing cells in mice fed Nissle-GLP-1 (A) and not in Nissle-fed or control mice (B). Cells were co-stained blue with antibodies against representative proteins from each of the 4 cell types: NOD-2 for paneth cells (C), mucin-2 (MUC-2) for goblet cells (D), sucrose isomaltase (SI) for absorptive cells (E), and chromogranin A (Chr-A) for enteroendocrine cells (F). Co-staining with antibodies to representative proteins from each of the four types of enteric cell suggested that the lineage of these cells is related to enteroendocrine cells.

Figure 11A:
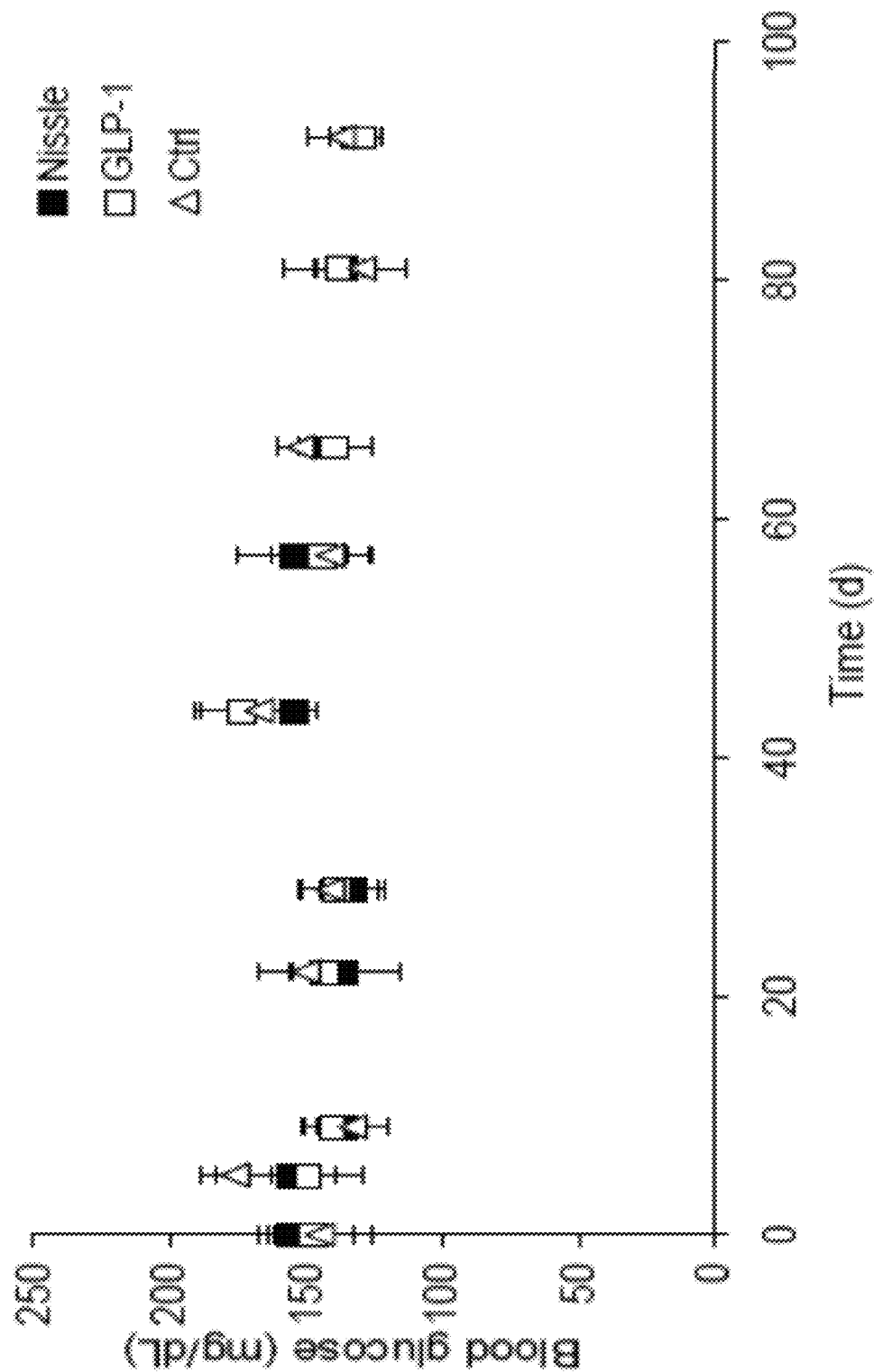

FIG. 11A illustrates blood glucose levels over time of healthy mice (non-STZ treated) which were also fed Nissle and Nissle GLP-1.

Figure 11B:
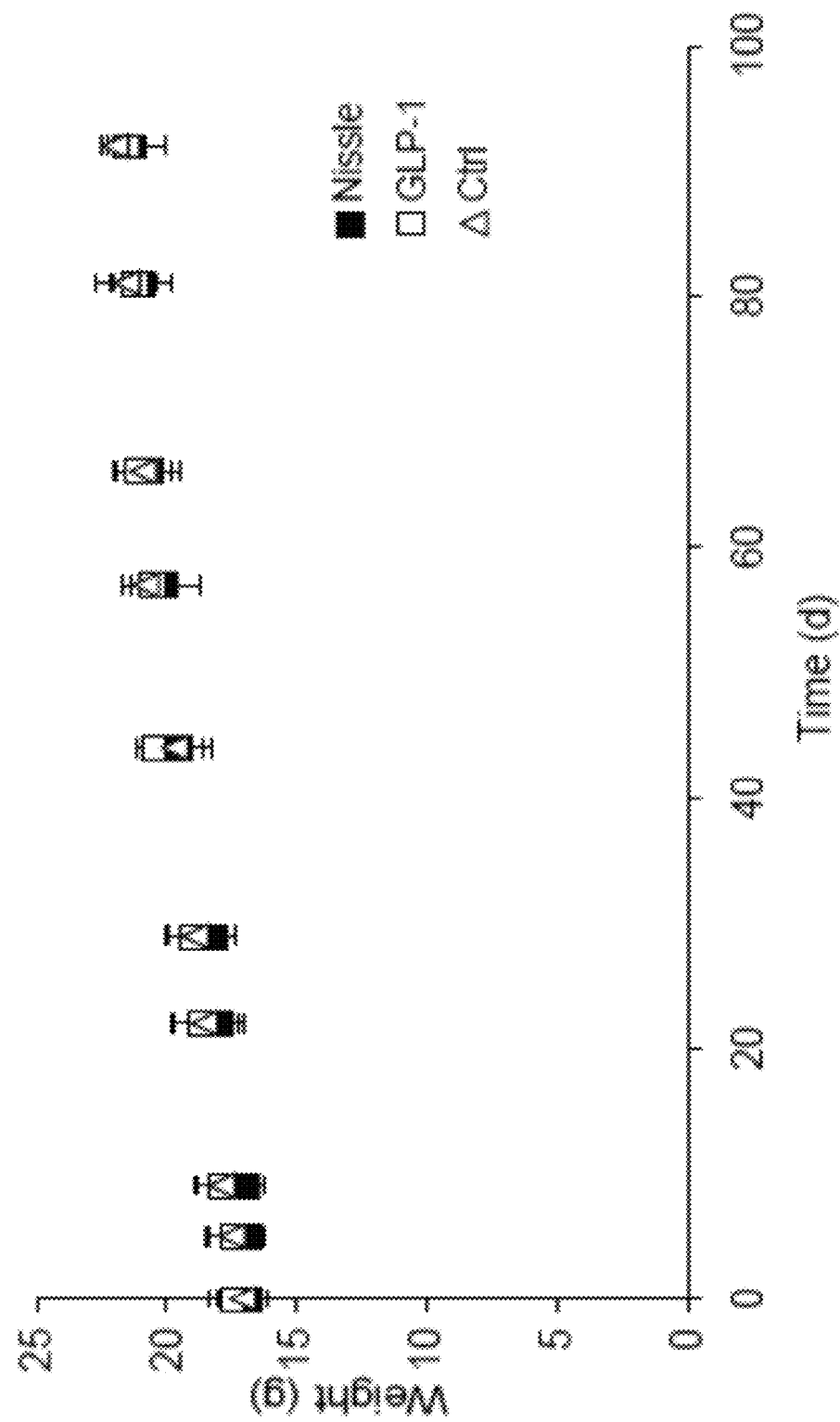

FIG. 11B illustrates weight changes of healthy mice (non-STZ treated) which were also fed Nissle and Nissle GLP-1 over time.

Figure 12:
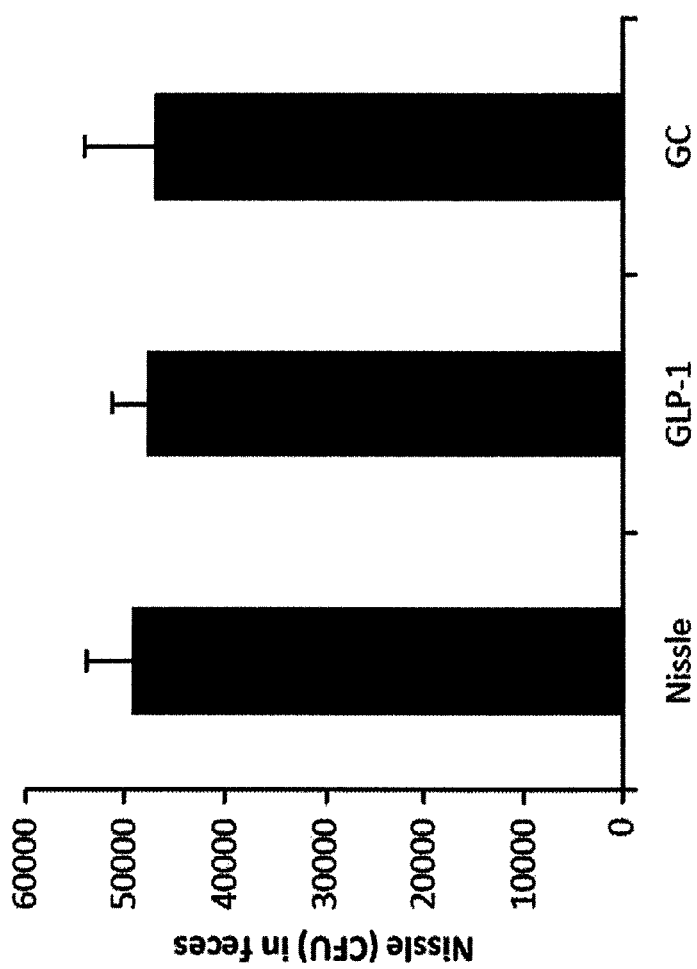

FIG. 12 illustrates measurement of Nissle survivability in the mouse feces of strains fed Nissle, Nissle expressing GLP-1 from a plasmid or Nissle-GLP-1.

Figure 13:
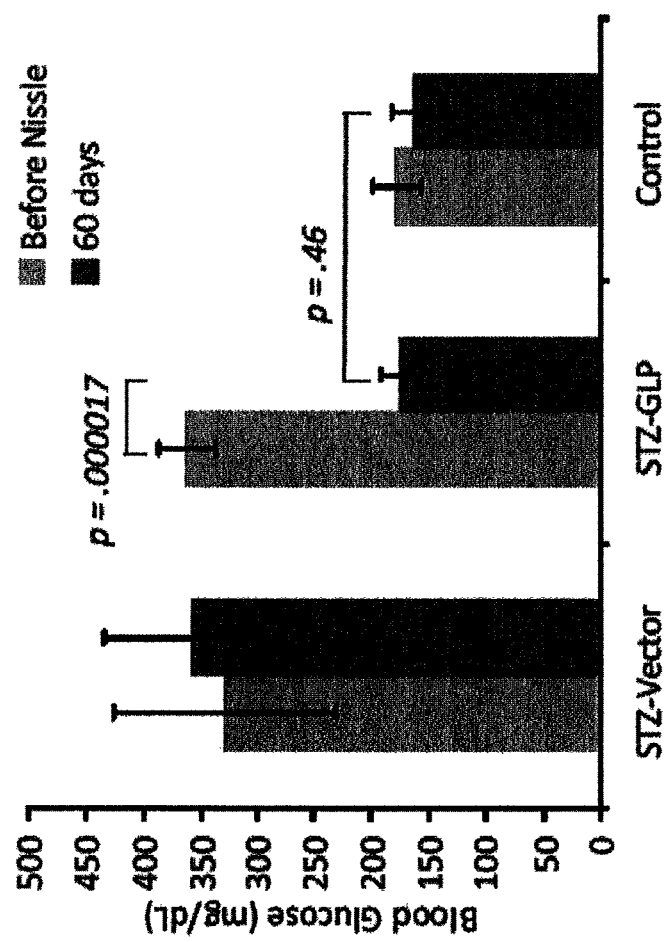

FIG. 13 illustrates random blood glucose levels after Nissle treatments with either Nissle with a dummy plasmid, Nissle with GLP-1(1-37) from the same plasmid or no treatment or no STZ (control).

Figure 14:
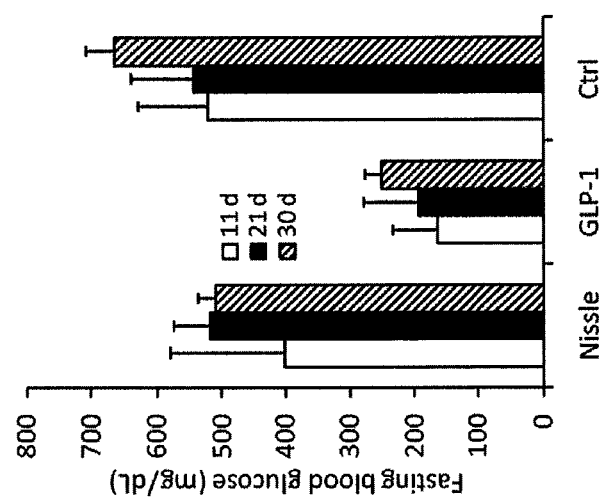

FIG. 14 illustrates non-obese diabetic (NOD) mouse fasting blood glucose levels after NOD mice were fed twice daily with Nissle, Nissle expressing GLP-1(1-37) chromosomally or given no treatment. Mice were fasted 4 hours just before blood glucose was measured. Times indicate days after treatment was started.

Figure 15:
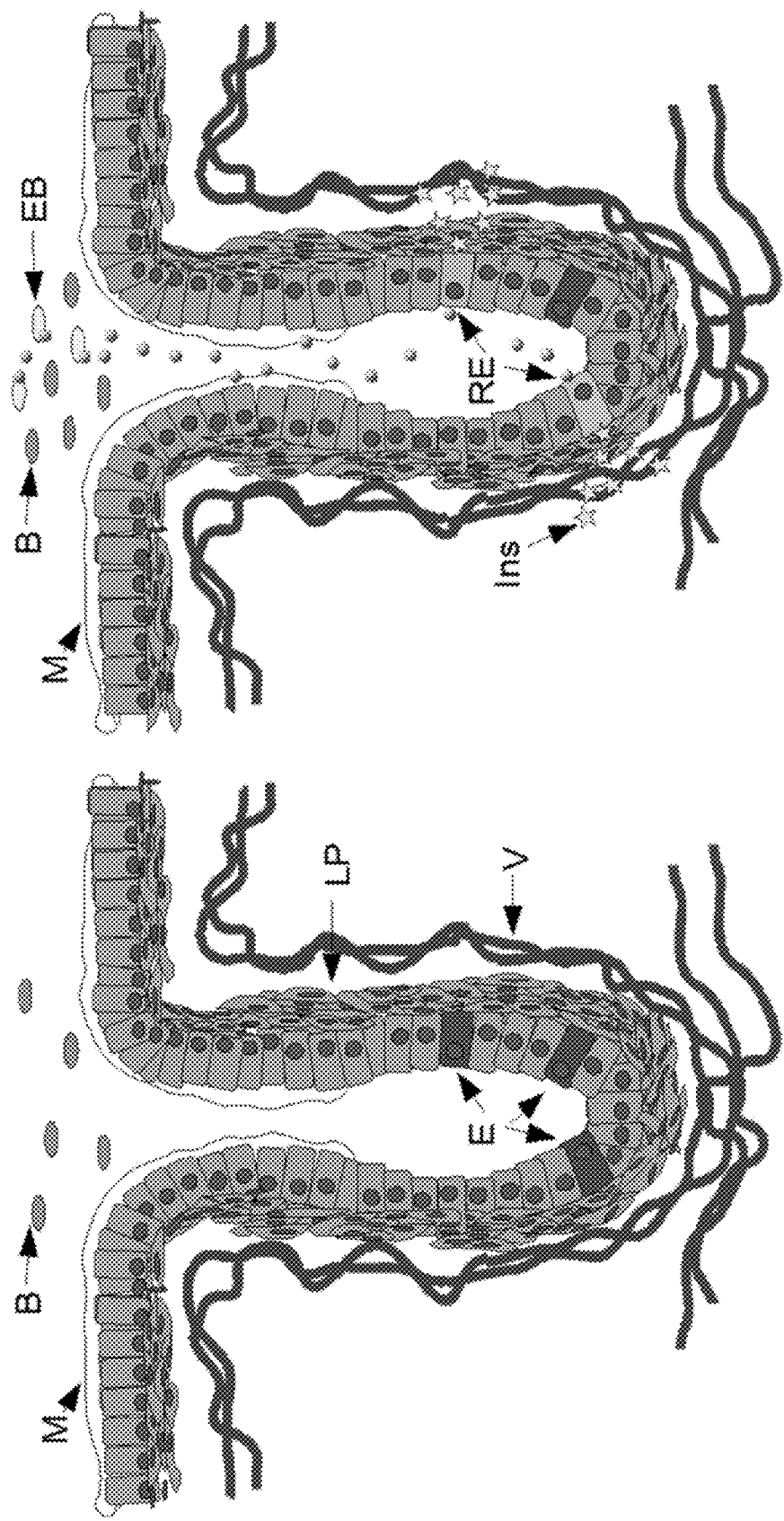

FIG. 15 illustrates the likely method of operation of the recombinant cell. Left: normal intestinal crypt with bacteria in lumen B in and on top of the mucosa M. Enteroendocrine cells (E) secrete hormones into the lamina propria (LP) and vasculature V. Right: recombinant cells of embodiments herein (EB) secrete GLP-1 (dots emerging from EB) into the crypts to reprogram early enteroendocrine cells into insulin-secreting cells (RE). Insulin (Ins, stars) is then secreted into the bloodstream in response to glucose.

FIGS. 16A-D illustrate bacterially-secreted GLP-1 in the mouse upper intestine. GLP-1(1-37) was secreted from *E. coli* Nissle 1917 (Nissle-GLP-1) that were fed twice daily to mice over the course of 60 days. a, Immunofluorescence of mouse upper intestinal sections revealed GLP-1 binding to intestinal mucosa. White arrow indicates GLP-1 expression from an enteroendocrine cell. Gray arrows indicate bacterially-secreted GLP-1 attached to epithelia. b, mice fed *E. coli* Nissle 1917 expressing a dummy peptide (Nissle) showed no mucosal GLP-1 staining. White arrow indicates an enteroendocrine cell. c, GLP-1 binding (% coverage) was quantified through image analysis. Values are averages of images taken from at least 3 mice and error bars represent 1 standard deviation. GLP-1=Nissle-GLP-1; Nissle=EcN expressing a dummy peptide. p value is from a student's t-test (n=3). d, Bacterial counts from mouse whole intestines: either upper intestine (unwashed), large intestine (lower GI, after a gentle wash with PBS) or fecal counts. *Fecal counts are per gram of feces. Values are averages for 3 mice and error bars represent 1 standard deviation.

FIGS. 17A-D illustrate reducing type 1 diabetes mellitus (T1DM) in STZ-treated mice. a, Mouse pancreases were harvested at the end of the study and the β-cell mass was determined from IHC sections stained for insulin. Images from 3 mice per group were analyzed and the average β-cell mass for each group is presented. Error bars represent standard deviations and the p values are from a student's t-test (n=3). Mice fed Nissle (Nissle), mice fed Nissle-GLP-1 (GLP-1), mice fed no bacteria (STZ), mice not treated with STZ or fed bacteria (Control) were treated as described in the text. b, Mouse blood glucose levels were measured after 60 days. Average values at the start of treatment (Day 0) and after 60 days are shown. Values presented are the average of at least 4 mice. Error bars represent one standard deviation. p values are from a student's t-test (n=4). c, Healthy mice untreated with STZ were fed Nissle (Nissle) and Nissle-GLP-1 (GLP-1) twice daily over a period of 92 days. Control mice fed no bacteria were used for comparison over the same time period (Control). Three time points are shown (0, 57 and 92 d). p values are from a student's t-test (n=4). d, After 60 days of bacterial treatment following STZ depletion of their β-cell mass, mice were subjected to a glucose tolerance test where they were fasted for 10 h and then injected with glucose (25 mg/kg body weight). Blood insulin (top panel) and glucose (bottom panel) levels were measured every 30 min for 1.5 h. ▲=STZ-treated mice fed no bacteria; ■=STZ-treated mice fed Nissle; □=STZ-treated mice fed Nissle-GLP-1; Δ=Control mice given no STZ and fed no bacteria. Values are averages for each treatment. Error bars represent standard deviations (n=4). Stars indicate significance in a student's t-test (n=4) between STZ-only treated mice (▲) and Nissle-GLP-1-fed mice (□) at the $p<0.05$ (*), $p<0.01$ () and $p<0.001$ (*) levels.

FIGS. 18A-H illustrate β-cell and epithelial markers in Nissle and Nissle-GLP-1-fed mice. Intestinal sections from STZ-treated (a, b, e-f) and healthy (c, d) mice fed Nissle (a, c) or Nissle-GLP-1 (b, d, e-f) were immuno-stained green for the presence of insulin (a-h) and co-stained blue for nucleic acid (DAPI, a-h) and red for either PDX-1 (a-d), ChrA (e, f), lysozyme (Lys, g) or sucrose isomaltase (SI, h). Right arrows in images e-f point to reprogrammed cells expressing insulin. Left arrows in b and all arrows in d point to insulin expressing cells. The left and down arrows in e and f point to cells expressing ChrA and not insulin. Up arrows in g point to Lys-expressing paneth cells. Left and up arrows in h point to SI. Inset panels in b, e and f are higher magnification images of insulin producing cells within the image in which they appear. Scale bars in a, e and h=25 μm; Scale bars in all other panels=100 μm. A=autofluorescence.

Figure 19:
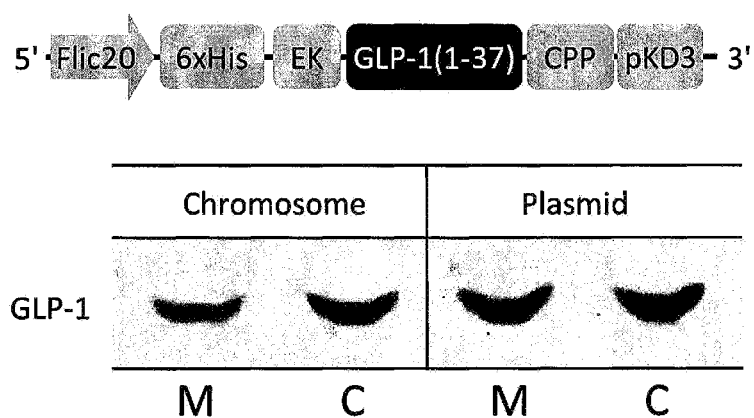

FIG. 19 illustrates secretion of GLP-1 from engineered commensal bacteria. Top. A schematic of the cassette used to transform *E. coli* Nissle 1917 into a GLP-1 secreting cell line via chromosomal insertion is shown. The cassette included a 5' untranslated region for fliC followed by a 6 histidine tag, an enterokinase site (EK), GLP-1(1-37) fused to a cell-penetrating peptide (CPP) and a section of pKD3 used for chromosomal insertion. Bottom. Western blotting shows the amounts of GLP-1 secreted (M) or in the cell pellet (C) from either chromosomally modified Nissle (chromosome) or from Nissle harboring the cassette on a plasmid (plasmid).

Figure 20:
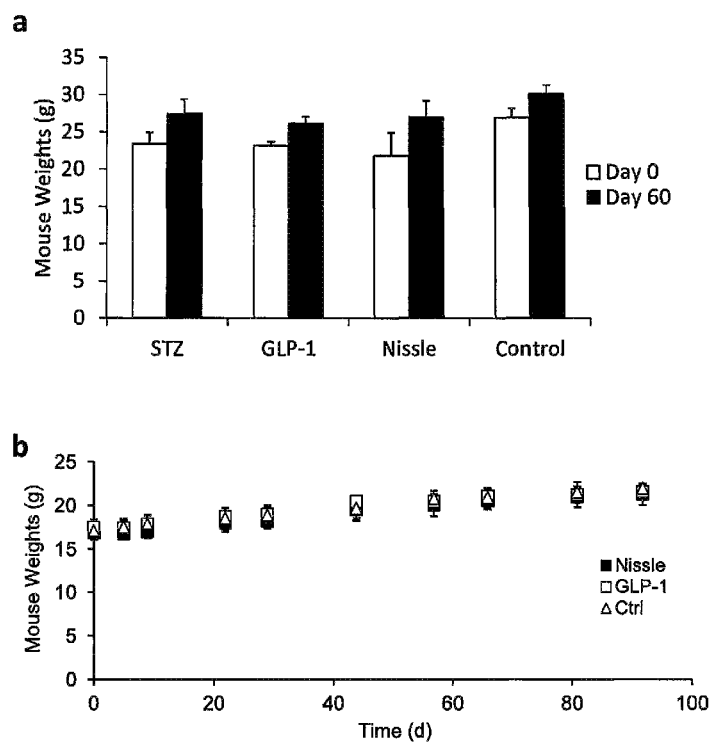

FIGS. 20A-B illustrate mouse weight levels for T1DM experiment. a, STZ-treated mouse weights were measured after 60 d of feeding with either Nissle (Nissle), Nissle-GLP-1 (GLP-1), or no bacteria (STZ). As a control, mice were not treated with STZ and not fed bacteria (Control). Average values at the start of treatment (Day 0) and after 60 days are shown. Values presented are the average of at least 4 mice. Error bars represent one standard deviation. b, C57BL/6 female mice (6-8 wks of age) were fed either Nissle, Nissle-GLP-1 or were not fed bacteria 2× per d. Weights were measured as indicated. Values are averages of 5 mice. Error bars represent standard deviations (n=5).

Figure 21:
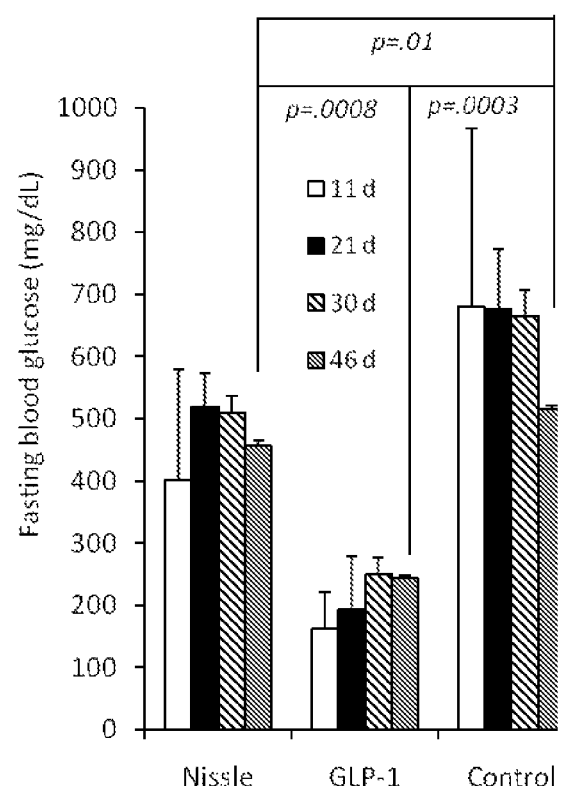

FIG. 21 illustrates NOD mouse blood glucose levels. NOD mice were fed Nissle (Nissle), Nissle-GLP-1 (GLP-1) or no bacteria (Control) 2× daily for 46 days. Fasting blood glucose was measured on days 11, 21, 30 and 46 post onset of daily feeding. Values are averages of mice in each group on the day specified. Error bars represent 1 standard deviation. p values are from a student's t-test on day 46 data (n=2).

Figure 22:
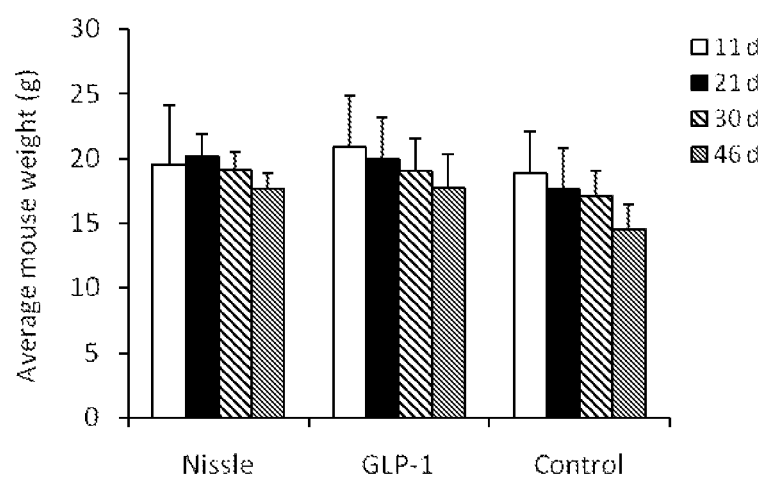

FIG. 22 illustrates NOD mouse weights. NOD mice were fed Nissle (Nissle), Nissle-GLP-1 (GLP-1) or no bacteria (Control) 2× daily for 46 days. Mouse weights were measured on days 11, 21, 30 and 46 post onset of daily feeding. Values are averages of mice in each group on the day specified. Error bars represent 1 standard deviation.

5. DETAILED DESCRIPTION OF THE INVENTION

Genetically engineered microorganisms (e.g., bacteria) are provided that have engineered signaling ability. Methods for using of engineered microorganisms (or recombinant cells derived therefrom) to express biosignaling molecules or biocompounds that ameliorate a disease or disorder. Commensal bacterial strains engineered to secrete glucagon-like peptide 1

(GLP-1)), PDX, GIF or glucagon-like peptide 2 (GLP-2)) or fragments, analogs or combinations thereof are also provided. Methods for ameliorating hyperglycemia and/or diabetes mellitus (DM) and other diseases using such engineered bacterial strains are also provided.

Methods for reprogramming intestinal cells into glucose-responsive insulin-secreting cells using commensal bacterial strains engineered to secrete glucagon-like peptide 1 (GLP-1), PDX, GIF, fragments thereof, analogs thereof or combinations thereof are further provided. Methods for enhancing intestinal functional, regenerating the gut's epithelial surface after an insult, e.g., inflammatory episodes, surgery, etc., and promoting healing of the intestinal lining using commensal bacterial strains engineered to secrete glucagon-like peptide 2 (GLP-2) are also provided.

For clarity of disclosure, and not by way of limitation, the detailed description of the invention is divided into the subsections set forth below.

5.1. Terminology

Before the present compositions and methods are described, it is to be understood that this invention is not limited to the particular processes, compositions, or methodologies described, as these may vary. It is also to be understood that the terminology used in the description is for the purpose of describing the particular versions or embodiments only, and is not intended to limit the scope of the present invention which will be limited only by the appended claims. Unless defined otherwise, all technical and scientific terms used herein have the same meanings as commonly understood by one of ordinary skill in the art. Although any methods and materials similar or equivalent to those described herein can be used in the practice or testing of embodiments of the present invention, the preferred methods, devices, and materials are now described. All publications mentioned herein are incorporated by reference in their entirety. Nothing herein is to be construed as an admission that the invention is not entitled to antedate such disclosure by virtue of prior invention.

It must also be noted that as used herein and in the appended claims, the singular forms "a", "an", and "the" include plural reference unless the context clearly dictates otherwise. Thus, for example, reference to a "recombinant cell" is a reference to one or more recombinant cells and equivalents thereof known to those skilled in the art, and so forth.

As used herein, the term "about" means plus or minus 10% of the numerical value of the number with which it is being used. Therefore, about 50% means in the range of 45%-55%.

"Administering" when used in conjunction with a therapeutic means to administer a therapeutic directly into or onto a target tissue or to administer a therapeutic to a patient whereby the therapeutic positively impacts the tissue to which it is targeted. Thus, as used herein, the term "administering", when used in conjunction with a recombinant cell, can include, but is not limited to, oral administration, providing a recombinant cell into or onto the target tissue; providing a recombinant cell systemically to a patient by, e.g., intravenous injection whereby the therapeutic reaches the target tissue; providing a recombinant cell in the form of the encoding sequence thereof to the target tissue (e.g., by so-called gene-therapy techniques).

"Administering" a composition may be accomplished orally, by injection, topical administration, or by any method in combination with other known techniques.

The term "animal" or "patient" or "host" or "subject," as used herein, includes, but is not limited to, humans and non-human vertebrates such as wild, domestic and farm animals. Preferably, the term "animal" or "patient" or "host" or "subject" refers to a mammal and, more preferably, to a human.

The term "improves" is used to convey that the present invention changes either the appearance, form, characteristics and/or the physical attributes of the tissue to which it is being provided, applied or administered. The change in form may be demonstrated by any of the following alone or in combination: conversion of intestinal epithelial cells into insulin-secreting cells, secretion of a therapeutic signal, expression of a target nucleic acid, or amelioration, prevention or reduction in the symptoms of the targeted disorder, such as a cancer, or an autoimmune, endocrine or cardiovascular disorder.

The term "inhibiting" includes the administration of a recombinant cell of the present invention to prevent the onset of the symptoms, alleviating the symptoms, or eliminating the disease, condition or disorder.

By "pharmaceutically acceptable", it is meant the carrier, diluent or excipient must be compatible with the other ingredients of the formulation and not deleterious to the recipient thereof.

As used herein, the term "therapeutic" means an agent utilized to treat, combat, ameliorate, prevent or improve an unwanted condition or disease of a patient. In part, embodiments of the present invention are directed to the treatment of diabetes or the increase of insulin production, or the treatment of cancer or an autoimmune, endocrine or cardiovascular disorder.

A "therapeutically effective amount" or "effective amount" of a composition is a predetermined amount calculated to achieve the desired effect, i.e., to prevent, ameliorate or reduce symptoms of a cancer or an autoimmune, endocrine, or cardiovascular disorder. The activity contemplated by the present methods includes both medical therapeutic and/or prophylactic treatment, as appropriate. The specific dose of a recombinant cell administered according to this invention to obtain therapeutic and/or prophylactic effects will, of course, be determined by the particular circumstances surrounding the case, including, for example, the encoded protein administered, the route of administration, and the condition being treated. The recombinant cells may be effective over a wide dosage range. However, it will be understood that the effective amount administered will be determined by the physician in the light of the relevant circumstances including the condition to be treated, the choice of encoded protein to be administered, and the chosen route of administration, and therefore the above dosage ranges are not intended to limit the scope of the invention in any way. A therapeutically effective amount of recombinant cell of this invention is typically an amount such that when it is administered in a physiologically tolerable excipient composition, it is sufficient to achieve an effective systemic concentration or local concentration in the tissue.

The terms "treat," "treated," or "treating" as used herein refers to both therapeutic treatment and prophylactic or preventative measures, wherein the object is to prevent or slow down (lessen) an undesired physiological condition, disorder or disease, or to obtain beneficial or desired clinical results. The term "treatment" as used herein also includes preventing the onset, establishment and spread of the undesired physiological condition, disorder or disease. For the purposes of this disclosure, beneficial or desired clinical results include, but are not limited to, alleviation of symptoms; diminishment of the extent of the condition, disorder or disease; stabilization (i.e., not worsening) of the state of the condition, disorder or disease; delay in onset or slowing of the progression of the condition, disorder or disease; amelioration of the condition, disorder or disease state; and remission (whether partial or total), whether detectable or undetectable, or enhancement or improvement of the condition, disorder or disease. Treatment includes eliciting a clinically significant response without excessive levels of side effects. Treatment also includes prolonging survival as compared to expected survival if not receiving treatment.

Generally speaking, the term "tissue" refers to any aggregation of similarly specialized cells which are united in the performance of a particular function.

5.2. GLP-1, PDX-1, GIP and GLP-2

Three proteins, GLP-1 (glucagon-like peptide 1), PDX-1 (pancreatic and duodenal homeobox gene 1), and gastric inhibitory polypeptide (GIP) may stimulate intestinal epithelial cells to synthesize insulin in response to glucose (GIP and GLP-1) and irrespective of glucose levels (PDX-1). A fourth protein, GLP-2, is known in the art to have a number of actions in the gastro-intestinal (GI) tract.

GLP-1

Glucagon-like peptide-1 (GLP-1) is derived from the transcription product of the proglucagon gene. The major source of GLP-1 in the body is the intestinal L cell that secretes GLP-1 as a gut hormone. GLP-1 (1-37), the intracellular precursor of GLP-1, is cleaved from proglucagon, and the first six amino acids are subsequently removed from the N terminus to form bioactive peptides. The principal biologically active forms of GLP-1 are: GLP-1 (7-37) and the predominant circulating active form GLP-1 (7-36) amide. GLP-1 is secreted by intestinal epithelia of the distal small bowel in response to glucose and other nutrients. It has a very short half-life, and its degradation by dipeptidylpeptidase IV (DPP-4) occurs in the blood vessels draining the intestinal mucosa. GLP-1 activates insulin synthesis in pancreatic β cells by binding to the membrane receptor GLP-1R and may be a therapeutic for treating both type 1 and type 2 diabetes. It has been surprisingly found that intestinal epithelial cells injected with GLP-1 may become glucose-responsive, insulin-secreting cells and subsequent surgical implantation of epithelial cells stimulated in vitro with GLP-1 into a host may result in a reversal of diabetes mellitus in the host. As disclosed herein, it is believed that the biologically inactive form, GLP-1 (1-37), may reprogram intestinal cells into glucose responsive insulin secreting cells.

GIP

GIP (also known as glucose-dependent insulinotropic peptide) induces insulin secretion, and may be primarily stimulated by hyperosmolarity of glucose in the duodenum. GIP is also thought to have significant effects on fatty acid metabolism through stimulation of lipoprotein lipase activity in adipocytes. GIP is derived from a 153-amino acid proprotein encoded by the GIP gene and circulates as a biologically active 42-amino acid peptide. It is synthesized by K cells, which are found in the mucosa of the duodenum and the jejunum of the gastrointestinal tract. Like all endocrine hormones, it is transported by blood. Gastric inhibitory polypeptide receptors are seven-transmembrane proteins found on beta-cells in the pancreas.

PDX-1

Additionally, the transcriptional activator PDX-1 stimulates insulin secretion in both β cells and intestinal epithelia. Supplemental gut bacteria are widely available as "probiotics" and are generally regarded as safe by the Food and Drug Administration. Potential advantages of using commensal strains for in vivo recombinant gene expression include their compatibility with the host (particularly the host's immune system), their controllable persistence in the gut, and their ability to be orally dosed. Commensal bacterial expression of various recombinant cytokines and antigens in animal models has been reported.

Reprogramming stem cells into β-cells or cells with insulin secreting potential has been the subject of several studies over the last 10 years. Focus has been on generating stem cells in vitro for transplantation as well as causing either pancreatic or other tissue-specific stem cells to convert to β-cells in vivo. Without wishing to be bound by theory, it is believed that an inactive form of glucagon like peptide 1 (GLP-1(1-37)) could stimulate developing and adult intestinal stem cells to become glucose-responsive insulin-secreting cells through the Notch signaling pathway. Embryonic jejunums (E14.5) incubated with GLP-1 in vitro and surgically implanted into adult diabetic rats could reverse STZ-induced type 1 diabetes mellitus (T1DM); but adult enterocyte differentiation (which occurs from the intestinal crypts) does not give rise to significant numbers of insulin-producing cells and that the proliferating and pseudostratified cells of the developing fetus (pre-E17) appear to be required for significant differentiation into cells with β-like functionality.

GLP-2

Full length glucagon-like peptide-2 (GLP-2) is a 33 amino acid peptide, co-secreted along with GLP-1 from intestinal endocrine cells in the small and large intestine. Similar to GLP-1, active form GLP-2 (1-33) is cleaved to inactive form GLP-2 (3-33) by protease DPPIV. GLP-2 is known in the art to have a number of actions in the gastro-intestinal (GI) tract including stimulation of mucosal growth in the small and large intestine, inhibition of enterocyte and crypt cell apoptosis, stimulation of enterocyte glucose transport and GLUT-2 expression, increased nutrient absorption, inhibition of gastric emptying and gastric acid secretion, reduction of intestinal permeability, stimulation of intestinal blood flow, and relaxation of intestinal smooth muscle (www.glucagon.com, visited Oct. 3, 2011). GLP-2 also has actions outside the GI tract, including stimulation of cell proliferation in rat astrocyte cell cultures (Glucagon-like peptide-2 stimulates the proliferation of cultured rat astrocytes. Eur J. Biochem. 2003 July; 270(14):3001-9; cited at www.glucagon.com, visited Oct. 3, 2011). Although plasma glucose does not change following GLP-2 administration in rodents or humans, pharmacological levels of GLP-2 (~10-fold higher than normal) are associated with increased circulating levels of glucagon in the fasted and postprandial state in normal human hosts (Glucagon-like Peptide 2 stimulates glucagon secretion, enhances lipid absorption, and inhibits gastric acid secretion in humans; Gastroenterology. 2006 January; 130(1):44-54; cited at www.glucagon.com, visited Oct. 3, 2011).). Without wishing to be bound by theory, it is believed that GLP-2 stimulates cell proliferation of enterocytes in the intestine.

5.3. Recombinant Cells

Embodiments described herein relate generally to the use of isolated, engineered recombinant cells to directly or indirectly treat endocrine, cardiovascular or autoimmune disorders.

Embodiments may be directed to a recombinant cell comprising a signal sequence and a promoter. In some embodiments, the signal sequence may be capable of being expressed by the recombinant cell. In some embodiments, the signal sequence may cause secretion of a therapeutic protein out of a cytoplasm of the recombinant cell. In some embodiments, the signal sequence may be capable of regulating signal-dependent expression of a target nucleic acid. In some embodiments, the signal sequence may be capable of regulating signal-dependent expression of a target nucleic acid in response to an environmental stimulus. In some embodiments, the signal sequence and the promoter are encoded on a plasmid in the recombinant cell. In some embodiments, the signal sequence and promoter are encoded on the nucleic acid of the recombinant cell.

In further embodiments, the signal sequence may regulate expression of a target nucleic acid. In some embodiments, the signal sequence may regulate expression of a target nucleic acid in response to an environmental stimulus. In some embodiments, the signal sequence may be GIP, GLP-1, PDX-1, fragments thereof, analogs thereof, or combinations thereof. In some embodiments, the target signal sequence may be capable of stimulating expression of a disease-preventing factor or inhibiting expression of a causal factor of the disease. In embodiments, the environmental stimulus may be glucose. In some embodiments, the disease-preventing factor may comprise insulin. In some embodiments, administration of the recombinant cell will not cause an increase in blood insulin level in healthy subjects.

In some embodiments, the signal sequence may comprise glucagon-like peptide-1 (GLP-1) or fragments or analogs thereof. In some embodiments, GLP-1 may include GLP-1 (1-37), GLP-1(7-37), GLP-1 (7-36) amide or combinations thereof. Analogs of GLP-1 are known in the art and are described hereinbelow. As disclosed hereinabove, GLP-1 is derived from the transcription product of the proglucagon gene. The major source of GLP-1 in the body is the intestinal L cell that secretes GLP-1 as a gut hormone. The biologically active forms of GLP-1 are: GLP-1-(6-37), GLP-1-(7-37) and GLP-1-(7-36) NH2. Those peptides result from selective cleavage of the proglucagon molecule. In certain embodiments, fragments of GLP-1 that are 4-7, 7-10, 10-13, 13-16, 16-19, 19-22, 22-25, 25-28, 28-31, 31-34 or 34-37 amino acids in length can also be used.

In some embodiments, the signal sequence may comprise glucagon-like peptide-2 (GLP-2) or fragments or analogs thereof. In some embodiments, GLP-2 may include GLP-2 (1-33), GLP-2 (3-33). or any other fragment or analog that is capable of stimulating expression of a disease-preventing factor or inhibiting expression of a causal factor of the disease. Analogs of GLP-2 are known in the art and described hereinbelow. In circulation, GLP-2 is present in two molecular forms, GLP-2 (1-33) and GLP-2 (3-33). Similar to GLP-1, active form GLP-2 (1-33) is cleaved to inactive form GLP-2 (3-33) by protease DPPIV. GLP-2 has been shown to play important roles in the regulation of gastrointestinal functions (digestion, absorption, motility, epithelial growth, and blood flow) and bone resorption. Thus, GLP-2 or its analogs may have therapeutic potentials for the treatment of diseases such as Crohn's disease and osteoporosis. In certain embodiments, fragments of GLP-2 that are 4-7, 7-10, 10-13, 13-16, 16-19, 19-22, 22-25, 25-28, 28-31, or 31-33 amino acids in length can also be used.

In some embodiments, the recombinant cell may be any transformable bacterial cell. In some embodiments, the recombinant cell may be derived from an enteric bacterium or a commensal bacterium. In some embodiments, the recombinant cell may be derived from a probiotic bacterium. In some embodiments, the recombinant cell may be a bacterium selected from various gram positive and gram negative families, including, but not limited to, *Escherichia, Pseudomonas, Bacteroides, Lactobacillus, Lactococcus, Bacillus, Proteus, Bifidobacterium, Streptococcus, Staphylococcus,* and *Corynebacterium*. In some embodiments, the recombinant cell may be a strain of *Escherichia coli*. In specific embodiments, the recombinant cell may be *E. coli* Nissle or *Lactobacillus*.

In some embodiments, the target nucleic acid may encode a mammalian factor that promotes normal functioning of a physiological process in a host or is effective in preventing onset, establishment, or spread of a non-infectious disease in the host. In some embodiments, the non-infectious disease in a host may comprise an autoimmune disease, endocrine disease, cancer, cardiovascular disease or a combination thereof. In some embodiments, the non-infectious disease may comprise diabetes. In some embodiments, the non-infectious disease may comprise Type 1 diabetes. In some embodiments, the non-infectious disease may comprise Type 2 diabetes.

A method is provided for delivering bioactive compounds to the luminal (villous) side of the upper intestine. The method can comprise providing commensal bacteria that populate the intestine and secrete the bioactive compound. This approach avoids the potential pitfalls of surgery or degradation in the bloodstream is the secretion of signals from commensal bacteria populating the intestine.

This method allows for expression of signals continuously or in response to a local stimulus with the subsequent transport being through the intestinal mucosa and not the blood.

Embodiments may be directed to a recombinant cell comprising a signal sequence and a promoter. In some embodiments, the signal sequence may be capable of being expressed by the recombinant cell. In some embodiments, the signal sequence may cause secretion of a therapeutic protein out of a cytoplasm of the recombinant cell. In some embodiments, the signal sequence may be capable of regulating signal-dependent expression of a target nucleic acid. In some embodiments, the signal sequence may be capable of regulating signal-dependent expression of a target nucleic acid in response to an environmental stimulus. In some embodiments, the signal sequence and promoter are encoded on a plasmid in the recombinant cell. In some embodiments, the signal sequence and promoter are encoded on the nucleic acid of the recombinant cell.

In some embodiments, the recombinant cell may be any transformable bacterial cell. In some embodiments, the recombinant cell may be an enteric bacterium or a commensal bacterium. In some embodiments, the recombinant cell may be a probiotic bacterium. In some embodiments, the recombinant cell may be a bacterium selected from the group consisting of *Escherichia, Pseudomonas, Bacteroides, Lactobacillus, Lactococcus, Bacillus, Proteus, Bifidobacterium, Streptococcus, Staphylococcus,* and *Corynebacterium*. In some embodiments, the recombinant cell may be a strain of *Escherichia coli*. In some embodiments, the recombinant cell may be *E. coli* Nissle. In some embodiments, the target nucleic acid may encode a mammalian factor that promotes normal functioning of a physiological process in a host or is effective in preventing onset, establishment, or spread of a non-infectious disease in the host. In some embodiments, the non-infectious disease in a host may comprise a cancer or an autoimmune disease, endocrine disease, cardiovascular disease or a combination thereof. In some embodiments, the non-infectious disease may comprise diabetes. In some embodiments, the non-infectious disease may comprise Type 1 diabetes. In some embodiments, the non-infectious disease may comprise Type 2 diabetes.

In some embodiments, recombinant cell comprises a promoter and a signal sequence. Any suitable promoter known in the art can be used. The promoter can be an inducible or constitutive promoter. In a specific embodiment, the promoter is a glucose-responsive promoter.

In one embodiment, the signal sequence may comprise GLP-1 or fragments or analogs thereof. In some embodiments, analogs of GLP-1 may be selected from the group consisting of taspoglutide, exenatide, exendin-4, liraglutide, albiglutide, (Val8)GLP-1, NN9924, CJC-1131, AVE010, LY548806, analogs described in U.S. Pat. No. 5,545,618, and the like.

In other embodiments, the signal sequence may comprise glucagon-like peptide-2 (GLP-2) or analogs thereof. GLP-2 is a 33 amino acid peptide, co-secreted along with GLP-1 from intestinal endocrine cells in the small and large intestine. Although plasma glucose does not change following GLP-2 administration in rodents or humans, pharmacological levels of GLP-2 (~10-fold higher than normal) are associated with increased circulating levels of glucagon in the fasted and postprandial state in normal human subjects. GLP-2 may also play a role as a growth factor for the small intestine and colon. Methods disclosed herein wherein the signal sequence is GLP-2 can be used to treat, for example, diseases such as Type 1 and Type 2 diabetes, diabetes related to obesity, chemotherapy-induced diarrhea; inflammatory bowel disease, ventricular and atrial fibrillation, postsurgical organ failure, irritable bowel syndrome, interstitial cystitis/bladder pain syndrome, short bowel syndrome, ulcerative colitis, Metabolic Syndrome, Crohn's disease, osteoporosis or can be used to treat a host following any type of intestinal surgery.

GLP-2 analogs are well known in the art. In some embodiments, analogs of GLP-2 may be selected from the group consisting of GLP-2 which is naturally occurring in vertebrates, and to analogs of naturally occurring forms of GLP-2, which GLP-2 analogs elicit an intestinotrophic effect and are structurally altered, relative to a given vertebrate GLP-2, by at least one amino acid addition, deletion, substitution, or by incorporation of an amino acid(s) with a blocking group. Other analogs of GLP-2 are described in U.S. Pat. Nos. 5,834,428; 5,994,500; each of which is incorporated herein by reference.

The various vertebrate forms of GLP-2 include, for example, rat GLP-2 and its homologues including ox GLP-2, porcine GLP-2, degu GLP-2, bovine GLP-2, guinea pig GLP-2, hamster GLP-2, human GLP-2, rainbow trout GLP-2, and chicken GLP-2, the sequences of which have been reported by many authors including Buhl et al in J. Biol. Chem., 1988, 263(18):8621, Nishi and Steiner, Mol. Endocrinol., 1990, 4:1192-8, and Irwin and Wong, Mol. Endocrinol., 1995, 9(3): 267-77. Analogs of vertebrate GLP-2 can be generated using standard techniques of peptide chemistry and can be assessed for intestinotrophic activity, all according to the guidance provided herein. Particularly preferred analogs of the invention are those based upon the sequence of human GLP-2, as follows:

```
                                            (SEQ ID NO: 1)
His-Ala-Asp-Gly-Ser-Phe-Ser-Asp-Glu-Met-Asn-Thr-

Ile-Leu-Asp-Asn-Leu-Ala-Ala-Arg-Asp-Phe-Ile-Asn-

Trp-Leu-Ile-Gln-Thr-Lys-Ile-Thr-Asp
``` wherein one or more amino acid residues are conservatively substituted for another amino acid residue, as long as the analog still maintains intestinotrophic activity, such as small bowel growth, pancreatic islet growth, and/or increase in crypt/villus height, in a vertebrate. Conservative substitutions in any naturally occurring GLP-2, preferably the human GLP-2 sequence, are defined as exchanges within any of the following five groups:
I. Ala, Ser, Thr, Pro, Gly
II. Asn, Asp, Glu, Gln
III. His, Arg, Lys
IV. Met, Leu, Ile, Val, Cys
V. Phe, Tyr, Trp.

Non-conservative substitutions of amino acids in any vertebrate GLP-2 sequence are encompassed, provided that the non-conservative substitutions occur at amino acid positions known to vary in GLP-2 isolated from different species. Non-conserved residue positions are readily determined by aligning all known vertebrate GLP-2 sequences (see, e.g., Buhl et al., J. Biol. Chem., 1988, 263(18):8621, Nishi and Steiner, Mol. Endocrinol., 1990, 4:1192-8) Amino acid positions that vary in mammals and that can be substituted with non-conservative residues can be, in some embodiments, positions 13, 16, 19, 20, 27, and 28. The additional amino acid residues which vary in vertebrates and which also may be substituted with non-conserved residues occur at positions 2, 5, 7, 8, 9, 10, 12, 17, 21, 22, 23, 24, 26, 29, 30, 31, 32, and 33.

Alternatively, non-conservative substitutions may be made at any position in which alanine-scanning mutagenesis reveals some tolerance for mutation in that substitution of an amino acid residue with alanine does not destroy all intestinotrophic activity. The technique of alanine scanning mutagenesis is described by Cunningham and Wells, Science, 1989, 244:1081, and incorporated herein by reference in its entirety. Since most GLP-2 sequences consist of only approximately 33 amino acids (and in human GLP-2 alanine already occurs at four positions), one of skill in the art could easily test an alanine analogue at each remaining position for intestinotrophic effect, as taught in the examples below.

By aligning the known sequences of vertebrate GLP-2, a general formula has been constructed which takes into account the significant sequence homology among these GLP-2 species, as well as the residues which are known to vary between species. This formula may be used to guide the choice of particular preferred non-conserved residues for substitution, addition, deletion, or modification by addition of amino acid blocking groups. Thus, particular analogs of vertebrate GLP-2 embraced by the present invention, in accordance with one of its aspects, are those vertebrate GLP-2's and GLP-2 analogs that conform to the general formula represented below as SEQ ID NO:2:

```
                                            (SEQ ID NO: 2)
R1-[Y]m-His-Ala-Asp-Gly-Ser-Phe-Ser-Asp-Glu-Met-

AsnThr-aa1-Leu-Asp-aa2-Leu-Ala-aa3-aa4-Asp-Phe-

Ile-Asn-Trp-Leu-aa5-aa6-Thr-Lys-Ile-Thr-Asp-[X]n-

R2
``` wherein aa refers to any amino acid residue, and aa1 through aa6 are those residue positions known to vary among GLP-2 sequences obtained from different species, and:
X is one or two amino acids selected from group III, such as Arg, Lys or Arg-Arg
Y is one or two amino acids selected from group III, such as Arg, Lys or Arg-Arg
m is 0 or 1;
n is 0 or 1;
R1 is H or an N-terminal blocking group; and
R2 is OH or a C-terminal blocking group.

In several of the embodiments of the invention, aa1 through aa6 are as defined below:

aa1 is selected from group IV;
aa2 is selected from group I or II;
aa3 is selected from group I;
aa4 is selected from group III;
aa5 is selected from group IV;
aa6 is selected from group II or III.

In particularly preferred embodiments of the invention, aa1 through aa6 are chosen from the group of residues which are known to occur at that position in GLP-2's isolated from different species, as follows:

aa1 is Ile or Val;
aa2 is Asn or Ser;
aa3 is Ala or Thr;
aa4 is Lys or Arg;
aa5 is Ile or Leu; and
aa6 is Gln or His.

Human and rat GLP-2 differ from one another at only the amino acid residue at position 19. In the human sequence, this residue is alanine; in rat GLP-2, position 19 is threonine. Thus, particular GLP-2 or GLP-2 analogs embraced by the invention contain a variable residue at position 19. In these embodiments of the invention, the GLP-2 peptide conforms to SEQ ID NO:3 shown below:

(SEQ ID NO: 3)
R1-[Y]m-His-Ala-Asp-Gly-Ser-Phe-Ser-Asp-Glu-Met-

AsnThr-Ile-Leu-Asp-Asn-Leu-Ala-aa3-Arg-Asp-Phe-

Ile-Asn-Trp-Leu-Ile-Gln-Thr-Lys-Ile-Thr-Asp-[X]n-

R2 wherein aa3, Y, m, X, n, R1 and R2 are as defined above.

In other embodiments, the signal sequence may comprise a secreted peptide or an analog, a fragment or a portion thereof, including, but not limited to, GLP-1, PDX-1, GIP, GLP-2, insulin, growth hormone, prolactin, calcitonin, luteinising hormone, parathyroid hormone, somatostatin, thyroid stimulating hormone, vasoactive intestinal polypeptide, trefoil factors, cell and tissue repair factors, transforming growth factor β, keratinocyte growth factor, a structural group 1 cytokine adopting an antiparallel 4α helical bundle structure such as IL-2, IL-3, IL-4, IL-5, IL-6, IL-7, IL-9, IL-10, IL-11, IL-12, IL-13, GM-CSF, M-CSF, SCF, IFN-γ, EPO, G-CSF, LIF, OSM, CNTF, GH, PRL or IFNα/β, a structural group 2 cytokine which are often cell-surface associated, form symmetric homotrimers and the subunits take up the conformation of β jelly roll described for certain viral coat proteins such as the TNF family of cytokines, e.g., TNFα, TNFβ, CD40, CD27 or FAS ligands, the IL-1 family of cytokines, the fibroblast growth factor family, the platelet derived growth factors, transforming growth factor p and nerve growth factors, a structural group 3 cytokine comprising short chain α/β molecules, which are produced as large transmembrane pre-cursor molecules which each contain at least one EGF domain in the extracellular region, e.g., the epidermal growth factor family of cytokines, the chemokines characterized by their possession of amino acid sequences grouped around conserved cysteine residues (the C—C or C—X—C chemokine subgroups) or the insulin related cytokines, a structural group 4 cytokine which exhibits mosaic structures such as the heregulins or neuregulins composed of different domains, e.g., EGF, immunoglobulin-like and kringle domains. Biologically active analogs, fragments and portions of these secreted peptides are known in the art.

In some embodiments, the recombinant cell may comprise an inducible promoter. In some embodiments, the promoter may be a glucose-responsive promoter. In some embodiments, the promoter may be a fliC promoter. In some embodiments, the recombinant cell may further comprise a secretion tag. In some embodiments, the secretion tag may be a fliC secretion tag. In some embodiments, the secretion tag may be an alpha-hemolysin (HlyA) secretion tag. In some embodiments, the recombinant cell may further comprise a cell-penetrating peptide (CPP) sequence. In some embodiments, the recombinant cell may be capable of expressing the signal sequence as a fusion protein comprising a signal encoded by the signal sequence and a cell-penetrating peptide encoded by the cell penetrating peptide sequence.

5.4. Methods of Treatment

A method for treating a disease or disorder is provided. In one embodiment, the method can comprise administering the cell to a host under conditions effective to stimulate expression of a disease-preventing factor or inhibit expression of a causal factor of the disease. In some embodiments, the disease may be an autoimmune disease, cancer, endocrine disease, metabolic disease, cardiovascular disease or a combination thereof.

In some embodiments, the disease or disorder may be (or comprise) diabetes (including but not limited to Type 1 and Type 2 diabetes and diabetes related to obesity), obesity, Metabolic Syndrome, Crohn's disease, phenylketonuria, maple syrup urine disease, histidinemia, hyperglycemia, diabetic retinopathy, coronary heart disease, intercapillary glomerulosclerosis, nephropathy, neuropathy, ulceration or gangrene or the extremities, atherosclerosis, hypercholesterolemia, high blood pressure, hyperproteinemia, proteinuria, osteoporosis, anemia, hyperlipoproteinemia, ketoacidosis, hypertriglyceridemia, lactic acidosis, cardiomyopathy, Wilson's disease, leukodystrophy, fucosidosis, and cancers, such as gastrointestinal cancer, stomach cancer, gallbladder cancer, gastrointestinal stromal tumors, liver cancer, pancreatic cancer, colon cancer, chemotherapy-induced diarrhea; inflammatory bowel disease, ventricular and atrial fibrillation, postsurgical organ failure, irritable bowel syndrome, interstitial cystitis/bladder pain syndrome, short bowel syndrome, ulcerative colitis, or osteoporosis.

The method disclosed herein can also be used to treat a host following any type of intestinal surgery.

The effective (or "therapeutically effective") amount of the cell to be administered according to the methods disclosed herein can be determined using methods known in the art. The effective amount may depend on the stage of the undesired physiological condition or disease, the route of administration and/or other factors known to one of skill in the art. For example, in various embodiments, the effective amount of the cell may be at least about $10^4$ CFU/kg, at least about $10^5$ CFU/kg, at least about $10^6$ CFU/kg, or at least about $10^7$ CFU/kg. In other embodiments, the effective amount of the cell is about $10^4$-$10^{14}$ CFU/kg, $10^9$-$10^{12}$ CFU/kg, or $10^{10}$-$10^{11}$ CFU/kg of host's weight. In another embodiment, the effective amount of the cell is about $1 \times 10^{10}$, $2 \times 10^{10}$, $3 \times 10^{10}$, $4 \times 10^{10}$, $5 \times 10^{10}$, $6 \times 10^{10}$, $7 \times 10^{10}$, $8 \times 10^{10}$, $9 \times 10^{10}$ or $10 \times 10^{10}$ CFU/kg of host's weight.

For example, in one embodiment, the effective amount can be calculated as follows. Suppose that a desired amount of $8 \times 10^{10}$ CFU/kg is to be administered in a probiotic supplement of approximately $4.0 \times 10^{11}$ CFU/g, (as is commercially available), and assuming a human weight range of 25 kg for a child to 75 kg for an adult, this would mean a daily dose of 5-15 g/d. However, if the colonization efficiency was 2 orders of magnitude higher (as has been reported, see Rao, S. et al. Toward a live microbial microbicide for HIV: Commensal bacteria secreting an HIV fusion inhibitor peptide; Proc Natl Acad Sci USA 102, 11993-11998 (2005)) then the dose would be 50-150 mg/d. In other embodiments, the dose is 10-100, 100-200, 200-300, 300-400, 400-500, 500-600, 600-700, 700-800, 800-900, 900-1000 or 1000-2000 mg/d.

A method for reprogramming an intestinal epithelial cell into a glucose-responsive insulin secreting cell is also provided. In one embodiment, the method can comprise the step of administering a recombinant cell comprising a promoter and a signal sequence. Embodiments may be directed to a method of treating diabetes by administration of a recombinant cell comprising a promoter and a signal sequence. In further embodiments, the signal sequence may regulate expression of a target nucleic acid. In some embodiments, the signal sequence may regulate expression of a target nucleic acid in response to an environmental stimulus. In some embodiments, the signal sequence may be GIP, GLP-1, GLP-2, PDX-1, fragments thereof, analogs thereof, or combinations thereof. In some embodiments, the target signal sequence may be capable of stimulating expression of a disease-preventing factor or inhibiting expression of a causal factor of the disease or disorder. In some embodiments, the environmental stimulus may be glucose. In some embodiments, the disease-preventing factor may comprise insulin. In some embodiments, administration of the recombinant cell will not cause an increase in blood insulin level in healthy hosts.

A method for decreasing blood glucose levels is also provided. In one embodiment, the method can comprise administering an effective amount of the recombinant cell to a host in need thereof. In some embodiments, the method reduces blood glucose levels such that the host has normoglycemic levels. In some embodiments, the method reduces blood glucose levels by from about 20% to about 80%, from about 30 to about 70%, or from about 40% to about 60% after 30 days of treatment. In some embodiments, wherein the host is hyperglycemic, the administration of the recombinant cell reduces or eliminates a need for therapeutic administration of exogenous insulin to the host. In some embodiments, the recombinant cell is responsive to the level of glucose in the host. For example, in some embodiments, where the host has only a slightly elevated glucose level, the recombinant cell works to reduce glucose levels only so that it reaches normoglycemic levels and does not cause glucose deficiency.

A method for increasing blood insulin levels is also provided. In one embodiment, the method comprises administering an effective amount of the recombinant cell to a host in need thereof. In some embodiments, the method of increasing blood insulin levels causes the host to have normoglycemic levels. In some embodiments, the method increases blood insulin levels in response to glucose. In some embodiments, the method increases blood insulin levels by from about 20% to about 80%, from about 30 to about 70%, or from about 40% to about 60% after 30 days of treatment.

A method for reprogramming (or differentiating) an intestinal cell is also provided. In one embodiment, the intestinal cell is an intestinal epithelial cell, e.g., an enteroendocrine, paneth, absorptive enterocyte or goblet cell. In one embodiment the method comprises administering or localizing an effective amount of the recombinant cell to intestinal cells. Such methods may be carried out in vitro or in vivo. The method may further comprise administering such reprogrammed, differentiated or pre-treated intestinal cells to a host or patient in need thereof. The method may further comprise transplanting such reprogrammed, differentiated or pre-treated intestinal cells into a host or patient in need thereof.

A method for reprogramming an intestinal epithelial cell is also provided. Such methods may have several advantages over more traditional virally-mediated approaches. Without wishing to be bound by theory, by using commensal bacteria to deliver GLP-1, for example, enzymatic degradation of GLP-1 in the vasculature draining the intestinal mucosa may be avoided. GLP-1 may penetrate directly to the intestinal crypts from the luminal side without being exposed to the blood. In the intestinal crypts, enteric stem cells develop into the 4 types of enterocyte. One type of enterocyte, the enteroendocrine cell, secretes hormones into the vasculature. Without wishing to be bound by theory, it is believed that enteroendocrine cells become insulin-secreting in the presence of bacterially-secreted GLP-1. Such bacterial lines may be developed to differentiate intestinal stem cells into several different types of cells, essentially replacing function perhaps missing in other parts of the body. Examples include other pancreatic functions outside of β cells (e.g. a cells) and even, perhaps, thyroid, hepatocyte or immunoresponsive functions.

In certain embodiments, the methods of reprogramming cells disclosed herein can be used in vitro to reprogram cells and proliferate them. Such reprogrammed cells can subsequently be harvested and administered to (or implanted into) the host, using methods known in the art.

5.5. Diagnostic Methods and Uses

In some embodiments, the recombinant cell may be administered in combination with another therapeutic compound. In particular embodiments, the recombinant cell may be administered in combination with a compound having a synergistic effect. In other embodiments, the recombinant cell may be administered in conjunction with DPP-4 inhibitors, GLP-2, GLP-1 agonists, dimethyl sulfoxide, insulin, alpha-glucosidase inhibitors, pramlintide, meglitinides, repaglinide, nateglinide, chlorpropamide, metformin, sulfonylurea, glipizide, glyburide, glimepiride, thiazolidinediones, fragments thereof, analogs thereof or combinations thereof. Examples of DPP-4 inhibitors include sitagliptin, vildagliptin, saxagliptin, linagliptin, dutogliptin, gemigliptin, alogliptin, berberine or the like.

For example, in some aspects, a pharmaceutical composition is provided that comprises a recombinant cell, as defined above, and a pharmaceutically acceptable carrier or diluent, or an effective amount of a pharmaceutical composition comprising a recombinant cell as defined above. In some embodiments, the pharmaceutical composition may further comprise one or more stabilizers.

In embodiments of the methods disclosed herein in which commensal bacteria are used, an additional advantage is that their safety has been established by almost 100 years of use as probiotics, something that is lacking for virally-mediated approaches. Further, commensal bacteria may be easily destroyed using ordinary antibiotics if needed. Another advantage to using commensal bacteria is that they can be outfitted with feedback loops, allowing them to precisely control GLP-1 secretion to be in accordance with a specific luminal signal (glucose or IL-8, for example). Further, the use of GLP-1 has been shown to make enterocytes glucose-responsive, giving control of the insulin dose to the enterocytes much in the same way insulin control is mediated by β cells in healthy individuals. Finally, the use of commensal bacteria to reprogram enterocytes may eventually lead to a simple, orally-dosed and effective treatment for type-1, type-2 diabetes, and Metabolic Syndrome.

5.6. Routes of Administration and Formulations

The recombinant cells of the present invention can be administered in the conventional manner by any route in which they remain active. Effective routes in which the recombinant cells remain active can be determined using art-known methods. Administration of the recombinant cells can be systemic, topical, or oral. For example, administration can be, but is not limited to, parenteral, subcutaneous, intravenous, intramuscular, intraperitoneal, transdermal, oral, buccal, or ocular routes, or intravaginally, by inhalation, by depot injections, or by implants. Thus, modes of administration for the recombinant cells disclosed herein (either alone or in combination with other pharmaceuticals) can be, but are not limited to, sublingual, injectable (including short-acting, depot, implant, bead, or pellet forms injected subcutaneously or intramuscularly), or by use of vaginal creams, suppositories, pessaries, vaginal rings, rectal suppositories, intrauterine devices, and transdermal forms such as patches and creams.

Specific modes of administration will depend on the indication. The selection of the specific route of administration and the dose regimen is to be adjusted or titrated by the clinician according to methods known to the clinician in order to obtain the optimal clinical response. The amount of recombinant cell to be administered is that amount which is therapeutically effective. The dosage to be administered will depend on the characteristics of the host being treated, e.g., the particular animal treated, age, weight, health, types of concurrent treatment, if any, and frequency of treatments, and can be easily determined by one of skill in the art (e.g., by the clinician).

Pharmaceutical formulations comprising the recombinant cells and a suitable carrier can be solid dosage forms which include, but are not limited to, tablets, capsules, cachets, pellets, pills, powders and granules; topical dosage forms which include, but are not limited to, solutions, powders, fluid emulsions, fluid suspensions, semi-solids, ointments, pastes, creams, gels and jellies, and foams; and parenteral dosage forms which include, but are not limited to, solutions, suspensions, emulsions, and dry powder, comprising an effective amount of the recombinant cells. It is also known in the art that the active ingredients can be contained in such formulations with pharmaceutically acceptable diluents, fillers, disintegrants, binders, lubricants, surfactants, hydrophobic vehicles, water soluble vehicles, emulsifiers, buffers, humectants, moisturizers, solubilizers, preservatives and the like. The means and methods for administration are known in the art and an artisan can refer to various pharmacologic references for guidance. For example, *Modern Pharmaceutics*, Banker & Rhodes, Marcel Dekker, Inc. (1979); and *Goodman & Gilman's The Pharmaceutical Basis of Therapeutics*, 6th Edition, MacMillan Publishing Co., New York (1980), and *Remington's: The Science and Practice of Pharmacy*, 21$^{st}$ Edition, Lippincott Williams & Wilkins, Baltimore, Md. (2006) can be consulted.

The recombinant cells can be formulated for parenteral administration by injection, e.g., by bolus injection or continuous infusion. The recombinant cells can be administered by continuous infusion subcutaneously over a period of about 15 minutes to about 24 hours. Formulations for injection can be presented in unit dosage form, e.g., in ampoules or in multi-dose containers, with an added preservative. The compositions can take such forms as suspensions, solutions or emulsions in oily or aqueous vehicles, and can contain formulatory agents such as suspending, stabilizing and/or dispersing agents.

For oral administration, the recombinant cells can be formulated readily by combining these recombinant cells with pharmaceutically acceptable carriers well known in the art. Such carriers enable the recombinant cells of the invention to be formulated as tablets, pills, dragees, capsules, liquids, gels, syrups, slurries, suspensions and the like, for oral ingestion by a patient to be treated. Pharmaceutical preparations for oral use can be obtained by adding a solid excipient, optionally grinding the resulting mixture, and processing the mixture of granules, after adding suitable auxiliaries, if desired, to obtain tablets or dragee cores. Suitable excipients include, but are not limited to, fillers such as sugars, including, but not limited to, lactose, sucrose, mannitol, and sorbitol; cellulose preparations such as, but not limited to, maize starch, wheat starch, rice starch, potato starch, gelatin, gum tragacanth, methyl cellulose, hydroxypropylmethyl-cellulose, sodium carboxymethylcellulose, and polyvinylpyrrolidone (PVP). If desired, disintegrating agents can be added, such as, but not limited to, the cross-linked polyvinyl pyrrolidone, agar, or alginic acid or a salt thereof such as sodium alginate.

Dragee cores can be provided with suitable coatings. For this purpose, concentrated sugar solutions can be used, which can optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments can be added to the tablets or dragee coatings for identification or to characterize different combinations of active recombinant cell doses.

Pharmaceutical preparations which can be used orally include, but are not limited to, push-fit capsules made of gelatin, as well as soft, sealed capsules made of gelatin and a plasticizer, such as glycerol or sorbitol. The push-fit capsules can contain the active ingredients in admixture with filler such as, e.g., lactose, binders such as, e.g., starches, and/or lubricants such as, e.g., talc or magnesium stearate and, optionally, stabilizers. In soft capsules, the active recombinant cells can be dissolved or suspended in suitable liquids, such as fatty oils, liquid paraffin, or liquid polyethylene glycols. In addition, stabilizers can be added. All formulations for oral administration should be in dosages suitable for such administration.

For buccal administration, the compositions can take the form of, e.g., tablets or lozenges formulated in a conventional manner.

In one embodiment, the formulation is a controlled release formulation. U.S. Pat. No. 8,007,777 (Borek et al., Aug. 30, 2011) discloses an art-known example of a controlled release formulation for a probiotic. The formulation can contain a hydrophilic agent, an electrolytic agent and a polysaccharide, and can be in the form of a monolithic tablet for oral delivery to the intestinal system.

In a specific embodiment, the recombinant cells are spray-dried and the dried cells encapsulated using standard methods known in the art. It is preferred that the cells be completely dried before encapsulation.

Other preferred routes of administration and formulations can be determined by the skilled artisan by consulting standard pharmacological references for guidance. For example, *Remington's: The Science and Practice of Pharmacy*, 21$^{st}$ Edition, Lippincott Williams & Wilkins, Baltimore, Md. (2006), Chapters 45-47, disclose suitable oral solid dosage forms, coating of pharmaceutical dosage forms and extended-release and targeted drug delivery systems that can be used with the recombinant cells and methods disclosed herein.

For administration by inhalation, the recombinant cells for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit can be determined by providing a valve to deliver a metered amount. Capsules and cartridges of, e.g., gelatin for use in an inhaler or insufflator can be formulated containing a powder mix of the recombinant cell and a suitable powder base such as lactose or starch.

The recombinant cells of the present invention can also be formulated in rectal compositions such as suppositories or retention enemas, e.g., containing conventional suppository bases such as cocoa butter or other glycerides.

In addition to the formulations described previously, the recombinant cells can also be formulated as a depot preparation. Such long acting formulations can be administered by implantation (for example subcutaneously or intramuscularly) or by intramuscular injection.

Depot injections can be administered at about 1 to about 6 months or longer intervals. Thus, for example, the recombinant cells can be formulated with suitable polymeric or hydrophobic materials (for example as an emulsion in acceptable oil) or ion exchange resins, or as sparingly soluble derivatives, for example, as a sparingly soluble salt.

In transdermal administration, the recombinant cells of the present invention, for example, can be applied to a plaster, or can be applied by transdermal, therapeutic systems that are consequently supplied to the organism.

Pharmaceutical compositions of the recombinant cells also can comprise suitable solid or gel phase carriers or excipients. Examples of such carriers or excipients include but are not limited to calcium carbonate, calcium phosphate, various sugars, starches, cellulose derivatives, gelatin, and polymers such as, e.g., polyethylene glycols.

The recombinant cells can also be administered in combination with other active ingredients, such as, for example, adjuvants, protease inhibitors, or other compatible drugs or recombinant cells where such combination is seen to be desirable or advantageous in achieving the desired effects of the methods described herein.

In some embodiments, the disintegrant component comprises one or more of croscarmellose sodium, carmellose calcium, crospovidone, alginic acid, sodium alginate, potassium alginate, calcium alginate, an ion exchange resin, an effervescent system based on food acids and an alkaline carbonate component, clay, talc, starch, pregelatinized starch, sodium starch glycolate, cellulose floc, carboxymethylcellulose, hydroxypropylcellulose, calcium silicate, a metal carbonate, sodium bicarbonate, calcium citrate, or calcium phosphate.

In some embodiments, the diluent component comprises one or more of mannitol, lactose, sucrose, maltodextrin, sorbitol, xylitol, powdered cellulose, microcrystalline cellulose, carboxymethylcellulose, carboxyethylcellulose, methylcellulose, ethylcellulose, hydroxyethylcellulose, methylhydroxyethylcellulose, starch, sodium starch glycolate, pregelatinized starch, a calcium phosphate, a metal carbonate, a metal oxide, or a metal aluminosilicate.

In some embodiments, the optional lubricant component, when present, comprises one or more of stearic acid, metallic stearate, sodium stearyl fumarate, fatty acid, fatty alcohol, fatty acid ester, glyceryl behenate, mineral oil, vegetable oil, paraffin, leucine, silica, silicic acid, talc, propylene glycol fatty acid ester, polyethoxylated castor oil, polyethylene glycol, polypropylene glycol, polyalkylene glycol, polyoxyethylene-glycerol fatty ester, polyoxyethylene fatty alcohol ether, polyethoxylated sterol, polyethoxylated castor oil, polyethoxylated vegetable oil, or sodium chloride.

The following examples are offered by way of illustration and not by way of limitation.

6. EXAMPLES

6.1. Example 1

Constitutive Expression of GLP-1 in *Escherichia coli* Nissle

This example demonstrates the constitutive expression of GLP-1 in *Escherichia coli* Nissle.

Figure 1:
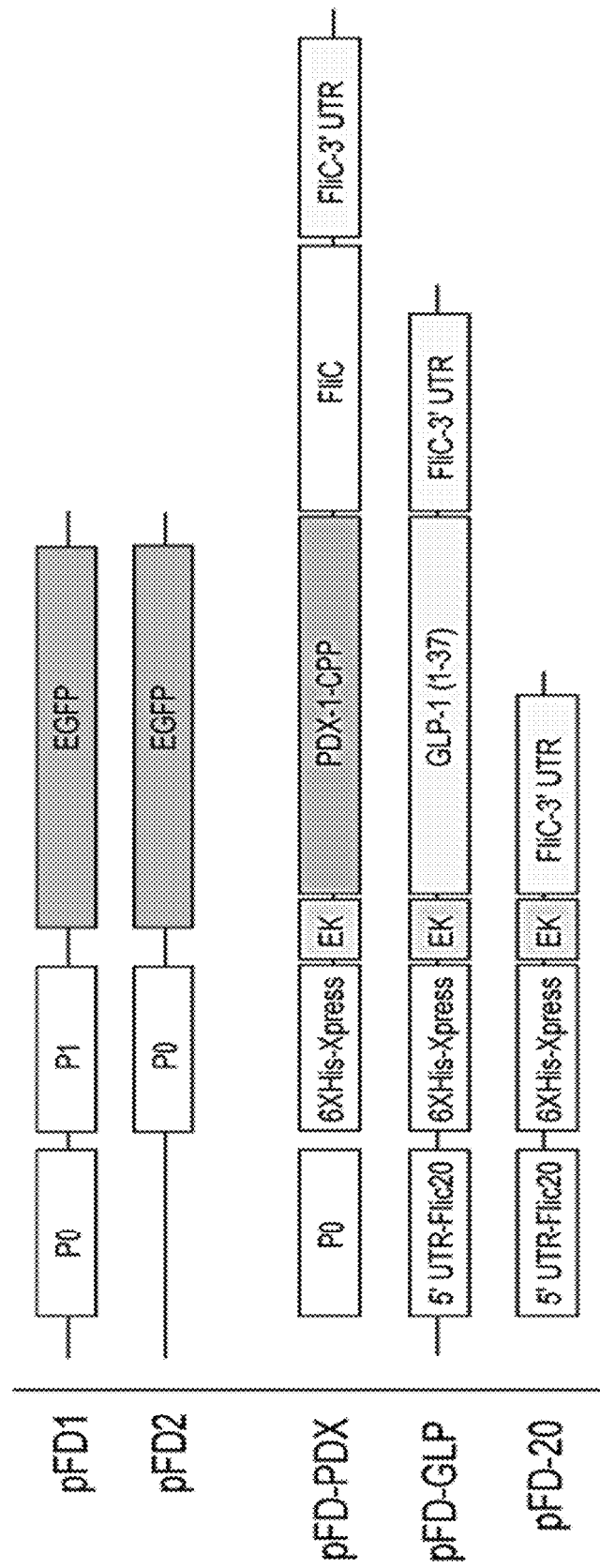
Figure 2:
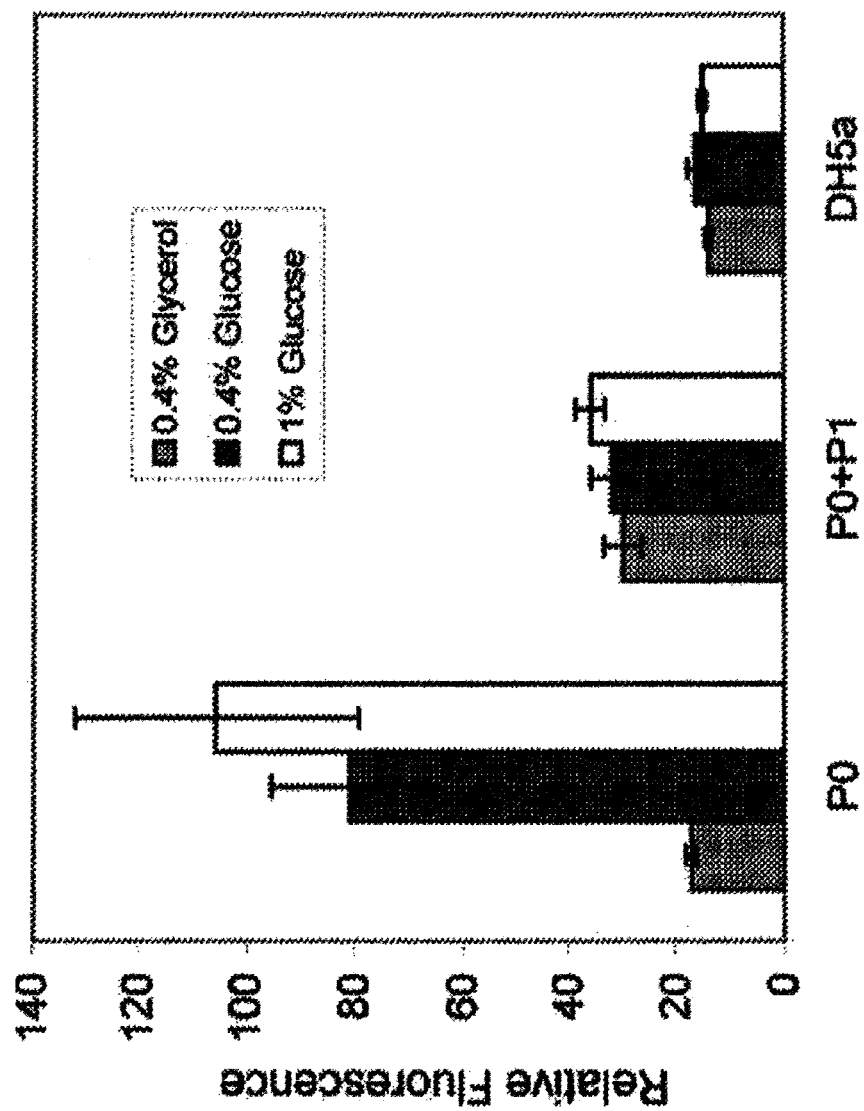

Plasmid construction: All cloning was performed using techniques described previously (Sambrook, J. & Russell. D. W. Molecular cloning: a laboratory manual. Edn. 3rd., Cold Spring Harbor Laboratory Press, Cold Spring Harbor, N.Y.; 2001). FIG. 1 provides a schematic of plasmids used in this study. To study the P0/P1 promoters from *E. coli* DH5α two plasmids were made (pFD1 and pFD2). pFD1 encoded the entire P0/P1 region to drive the expression of enhanced green fluorescent protein (EGFP). pFD2 encoded only the P0 region of the promoter upstream from EGFP. To test the efficacy of insulinotropic protein secretion from recombinant bacteria for stimulating insulin secretion in Caco-2 cells, plasmids pFD-PDX, pFD-GLP. and pFD-20 were constructed as described herein. FIG. 2 shows P0 and P0/P1 response to glucose. EGFP expression was used to measure the response of the P0 and/or P1 promoter to different media conditions. P0=P0 only; P0+P1=P0 plus P1 flanking region; DH5α=lac operon control. To test the efficacy of the glucose-responsive promoter system to produce recombinant proteins in response to glucose, two lengths of the glucose-responsive promoter region from *E. coli* DH5α were TA cloned into pGlow-GFP upstream and in-frame with GFP (results in FIG. 2). The two constructs consisted of the P0 promoter or the region spanning both the P0 and P1 promoters (Ryu, S. & Garges, S. Promoter Switch in the *Escherichia coli* Pts Operon. Journal of Biological Chemistry 269, 4767-4772 (1994)) in frame and upstream from the GFP start. Briefly, the P0 region was cloned from the genomic DNA of *E. coli* DH5α into pGLOW-GFP (Invitrogen, Carlsbad, Calif.) to make (pFD2). The P0/P1 region was cloned into pGLOW-GFP to make pFD1. In order to express the mammalian PDX-I gene in Nissle. The plasmid pFD-PDX was constructed as follows. The expression cassette 6×His-Xpress-EK-PDX-1-CPP was obtained using two rounds of high fidelity PCR (Stratagene, La Jolla, Calif.). The full length FLIC was obtained from DH5α via high fidelity PCR. These two fragments were cloned into pBluescript-KS to create 6×HiS-Xpress-EK-PDX-1-CPP-FLIC. The 6×HiS-Xpress-EK-PDX-1-CPP-FLIC fragment was then cloned into pGLOW-P0-GFP to create a vector (pFD-PDX) that uses the P0 promoter of *E. coli* to drive the expression of 6×HiS-Xpress-EK-PDX-1-CPP-FLIC.

To express the protein GLP-I constitutively in *Escherichia coli* Nissle, the plasmid pFD-GLP was constructed as follows. The sequence 6×HiS-Xpress-EK-GLP-1 (1-37) was made synthetically (IDT, Coralville, Iowa). This fragment was inserted via high fidelity PCR into pBluescript-KS to make pBluescipt-GLP. High fidelity PCR was used to clone the 5'UTR-FLIC20 sequence from pKS104 into pBluescript-GLP to make pBluescipt-20-GLP. The resultant vector contained the sequence: 5'UTR-FLIC20-6×His-Xpress-EK- GLP-1 (1-37). This sequence was cloned into pKS121 (containing the 3'UTR of FLIC to obtain the construct: 5'UTR-FLIC20-6×His-Xpress-EK-GLP-1 (1-37)-3'UTR by high fidelity PCR.

To obtain pFD-20, high fidelity PCR was used to clone the 5'UTR-FLIC20-6×His-Xpress-EK sequence from pFD-GLP. The PCR fragment was cloned into pKS I21 to obtain the construct: 5'UTR-FLIC20-6×His-Xpress-EK. pKS104 and pKS121 were obtained from University of Helsinki, Finland, Laboratory of Benita Westerlund-Wikström. The sequences of pKS104 and pKS121, however, can also be obtained from commercial sources or derived directly from the genome using conventional methods (e.g., sequence downloaded from GenBank, http://www.ncbi.nlm.nih.gov/genbank) and constructed using standard methods known in the art.

6.2. Example 2

Engineering of E. coli Nissle to Secrete GLP-1 or PDX-1-CPP

Figure 3:
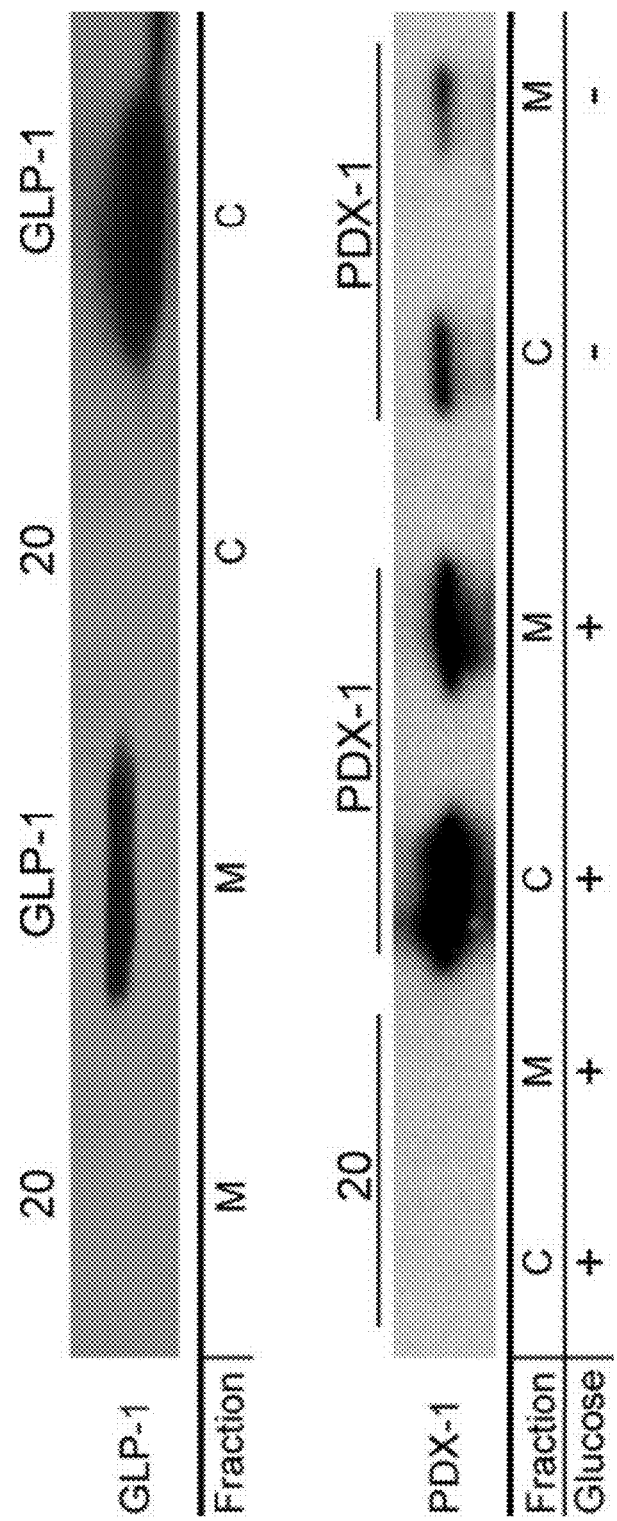
FIG. 3 illustrates the secretion of recombinant insulinotropic proteins by *E. coli* Nissle.

*Escherichia coli* Nissle 1917 (an over-the-counter probiotic strain, hereinafter referred to as Nissle) was engineered to secrete either GLP-1 (amino acids 1 through 37) under the control of the fliC promoter or PDX-1-CPP under the control of a glucose-responsive element. PDX-1 was secreted as a fusion with a cell-penetrating peptide (CPP) to facilitate rapid entry into the epithelia post-secretion. PDX-1 was secreted under the control of a glucose-responsive promoter element that had little observed leaky expression. Cells were grown for 6 to 8 h, normalized to an optical density at 600 nm of 1, and centrifuged. Western blots for secreted proteins GLP-1 (top blot) and PDX-1-CPP (bottom blot) in the Nissle supernatant and in the Nissle cell pellet are shown in FIG. 3. Referring to FIG. 3, the pellets were lysed, and the amount of each protein was determined (fraction "C"). The supernatant was preserved and similarly analyzed (fraction "M"). For cells expressing PDX-1-CPP, a comparison was made between cells grown in medium containing glucose (0.4%) or glycerol (0.4%). Cells expressing the empty plasmid (20) were used as a negative control. It was clear from these data that both proteins were being secreted.

6.3. Example 3

Induction of Insulin Secretion by E. coli Nissle Engineered to Secrete GLP-1 or PDX-1-CPP This example demonstrates induction of insulin secretion by *E. coli* Nissle engineered to secrete GLP-1 or PDX-1-CPP.

To test if the engineered Nissle strains could induce insulin secretion in human epithelial cells, Caco-2 cells were cultured with cell-free medium (CFM) from overnight cultures of Nissle strains expressing PDX-1-CPP, GLP-1, or a 20-amino acid sequence tag as a negative control. The overnight cultures were grown in F-12K medium (Mediatech, Manassas, Va.) without glucose (with the exception of PDX-1 strains, which required glucose to produce PDX-1). Culturing of the Caco-2 cells in a 1:1 mixture of fresh F-12K medium without glucose and CFM from overnight cultures of Nissle secreting PDX-1-CPP ("P"), GLP-1 ("G"), a 20-amino-acid sequence tag ("20"), or a 1:1 combination of PDX-1-CPP CFM and GLP-1 CFM ("GP") ran for 16 h before the medium was removed and the Caco-2 cells were cultured in medium with either glucose (0.4%) or glycerol (0.4%) for 2 h. Following the glucose challenge, each sample was analyzed for insulin secretion and transcription. As a positive control, Caco-2 cells were incubated in fresh F-12K medium (without glucose) and purchased GLP-1 (amino acids 1 through 37) for the same 16-h time period before being cultured with glucose (0.4%) or glycerol (0.4%) for 2 h.

Both transcription and enzyme-linked immunosorbent assay data indicated that human epithelia incubated with CFM from GLP-1 and PDX-1-CPP either together or separately were stimulated to produce insulin (FIGS. 4A-B). The most insulin production was consistently seen for incubations with GLP-1 (amino acids 1 through 37) CFM. PDX-1-CPP CFM stimulated glucose-responsive insulin secretion whether added by itself or with GLP-1. Both GLP-1- and PDX-1-mediated insulin secretions occurred in response to glucose. The negative control epithelia cultured with CFM from the 20-amino-acid sequence tag overnight exhibited no glucose-responsive insulin production (FIGS. 4A-B). That PDX-1-CPP treatment resulted in glucose-responsive insulin secretion in the Caco-2 cells (FIGS. 4A-B) was unexpected.

It was estimated that insulin levels in the blood would be 164 fmol/liter to 164 pmol/liter for Nissle survivability levels ranging from $10^6$ to $10^9$ CFU mL, respectively. Given that postprandial serum insulin concentrations can be as high as 400 pmol liter for adult non-diabetics, the unoptimized engineered bacteria may be able to stimulate an insulin release at least within the same order of magnitude as would be required for normal metabolism.

6.4. Example 4

Reprogramming Intestinal Cells into Glucose-Responsive Insulin-Secreting Cells This example demonstrates reprogramming intestinal cells into glucose-responsive insulin-secreting cells.

Nissle was engineered to secrete GLP-1(1-37) using the fliC promoter and secretion tag as described previously. The cassette inserted into Nissle is shown in FIG. 5. Secretion of GLP-1 was verified in culture for this strain and compared to secretion from a plasmid-bearing strain that contained the same sequence without the pKD3 chromosomal insertion cassette (FIG. 5). Secreted amounts for Nissle-GLP-1 were approximately half that of the plasmid-bearing strain and testing in vivo revealed no significant difference in glucose levels between mice treated with either strain (FIG. 6). Hence, Nissle-GLP-1 was used throughout these investigations instead of the strain bearing GLP-1 on a plasmid. Mice fed Nissle-GLP-1 demonstrated significant expression of recombinant protein (as determined by histidine tag staining) in vivo (FIG. 5).

To investigate whether simple oral dosing of human commensal bacterial strains engineered to secrete GLP-1 could ameliorate hyperglycemia in a mouse model of type 1 diabetes by reprogramming intestinal cells into glucose-responsive insulin-secreting cells, streptozotocin (streptozocin, Zanosar®) (STZ)-treated mice were fed daily with commensal bacteria engineered to secrete GLP-1 (1-37) (Nissle-GLP-1). Nissle-GLP-1 significantly reduced mouse blood glucose levels and significantly increased insulin levels in a glucose tolerance test. Healthy (non-diabetic) mice fed Nissle-GLP-1 had no change in blood glucose levels or weight. Mice treated with Nissle-GLP-1 developed insulin-secreting cells within the villi of the upper intestine. Co-immunostaining of insulin secreting cells with chromogranin A (Chr-A) suggests bacterially-mediated reprogramming of enteroendocrine cells into "β-like" cells. These results demonstrate that a method for treating or ameliorating type 1 diabetes comprising administering a human commensal bacterial strains engineered to secrete GLP-1 could be implemented orally at very low cost.

6.5. Example 5

Treatment of Streptozotocin (STZ)-Induced Diabetic Mice with E. coli Nissle 1917 Bacteria Expressing GLP-1

This example describes an exemplary method for treating Streptozotocin (STZ)-induced diabetic mice with E. coli Nissle 1917 bacteria expressing GLP-1.

Streptozotocin (STZ)-induced diabetic male mice (C57B6) 6-8 weeks old were fed with E. coli Nissle 1917 bacteria expressing either GLP-1 with a cell-penetrating peptide (STZ+GLP) or expressing a random 20 amino acid sequence (STZ-Vector). "Control" mice were not treated with STZ. Referring to FIG. 7, "before Nissle" measurements were taken after STZ treatment had significantly raised blood glucose levels and before Nissle bacteria were fed to the STZ-treated mice. All bacterial feeding stopped after 30 days. Blood glucose was measured again 60 days after bacterial feeding started ("60 days"). Values represent the averages of 4 mice. Error bars represent 1 standard deviation. p values are from a Student's t-test (n=4). The results show that diabetic mice fed GLP-1 secreting bacteria returned to normoglycemic levels after 30 days of treatment. Surprisingly, these mice maintained normal levels of blood glucose for an additional thirty days without any treatment.

Dissection and immunohistochemistry of these mice indicated that there were high levels of insulin in their intestinal tissue compared to controls fed only the commensal bacteria secreting a random peptide sequence (FIGS. 8A-B). Referring to FIG. 8A, high concentrations of insulin are noted by arrows.

6.6. Example 6

Treatment of Type 1 Diabetic Mice with E. coli Nissle 1917 Bacteria Expressing GLP-1

This example describes an exemplary method for treating Type 1 diabetic mice with E. coli Nissle 1917 bacteria expressing GLP-1.

Figure 9A:
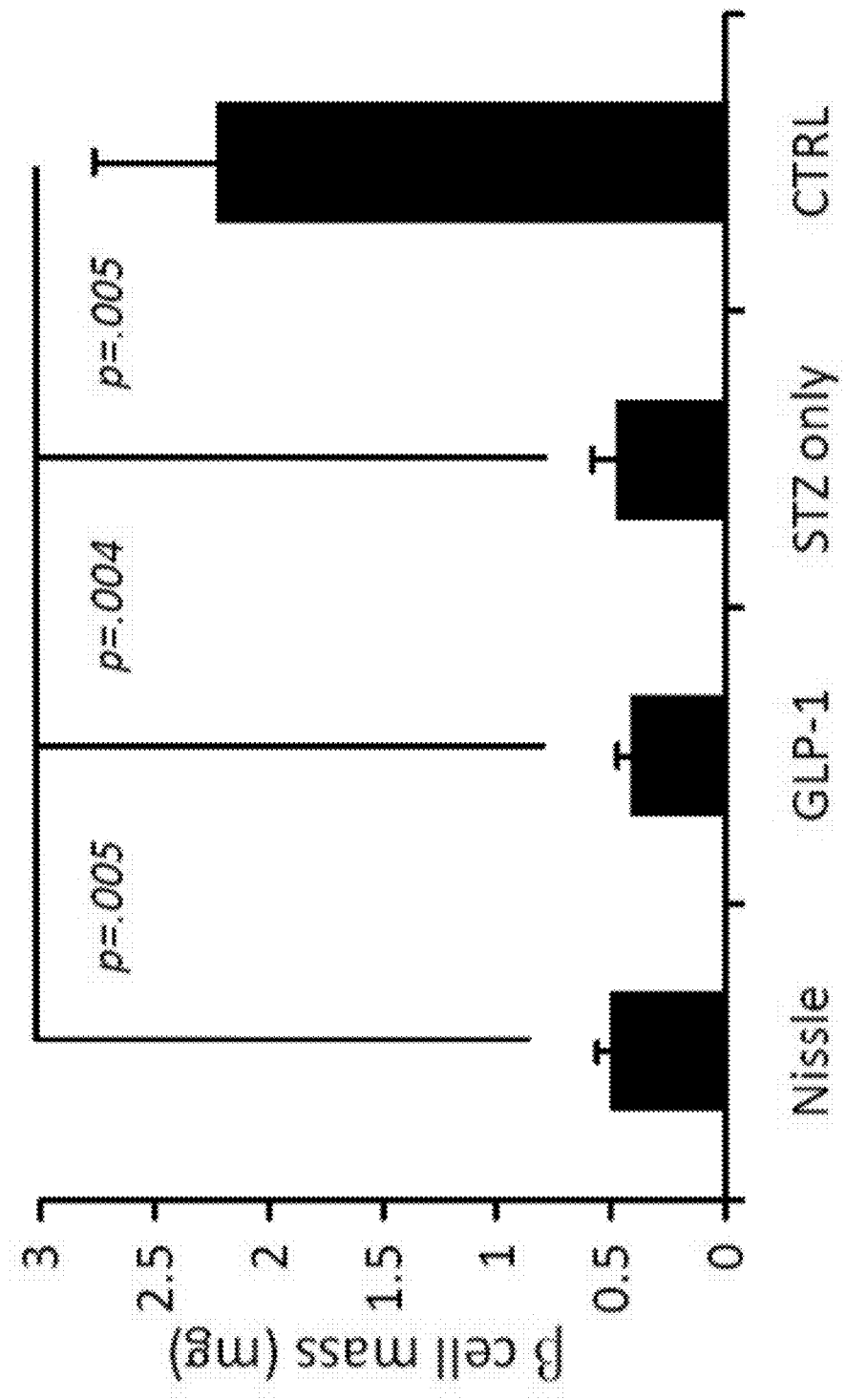
Figure 9B:
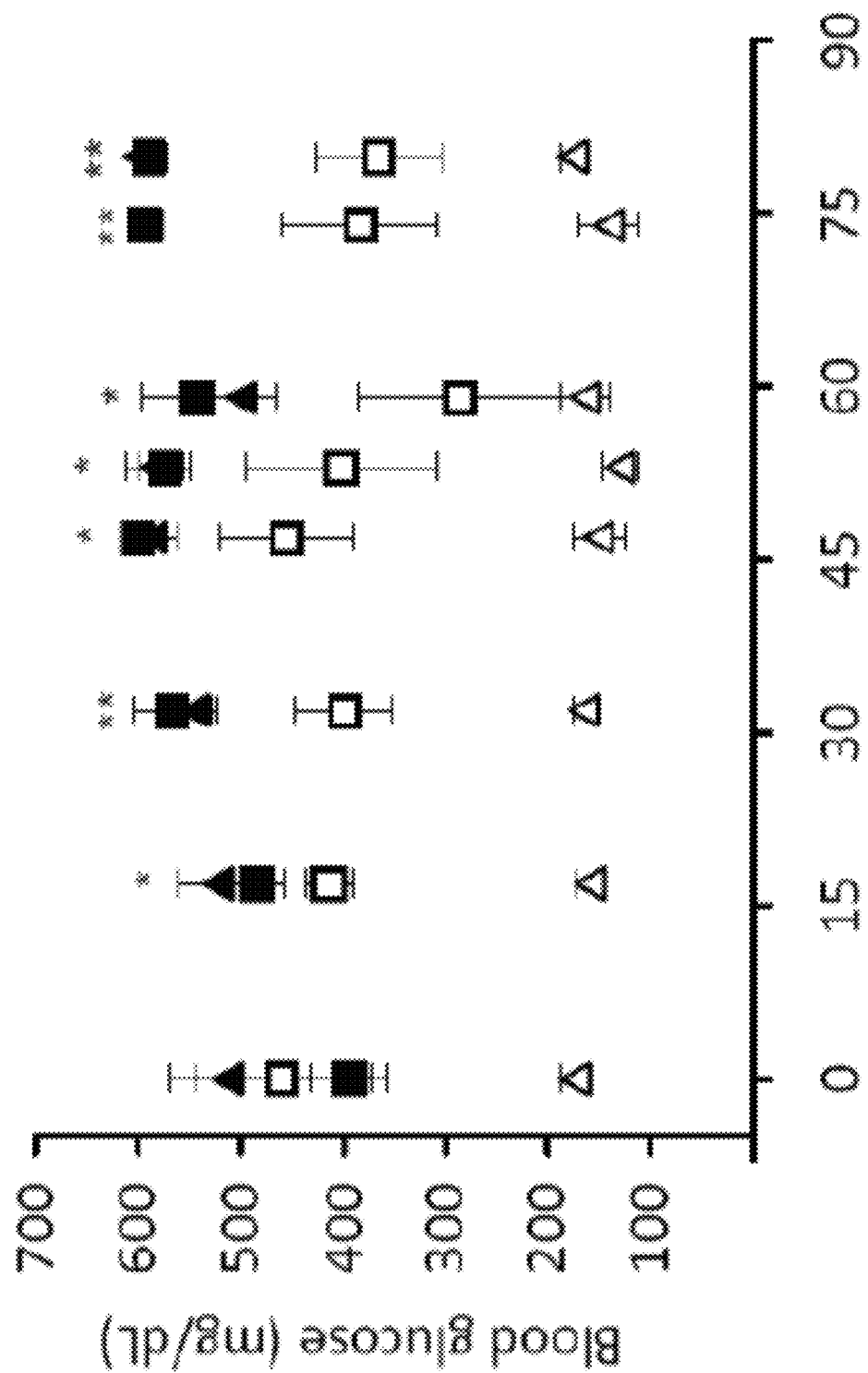

To determine the effect of Nissle-GLP-1 on Type 1 diabetes mellitus (T1DM), STZ mouse model of T1DM was made. C57BL/6J (B6) male mice were treated with STZ at a high dose and upon the onset of hyperglycemia (random glucose levels>350 mg/dL), mice were fed either Nissle-GLP-1, Nissle or given no treatment. Commensal bacterial feedings were carried out twice daily approximately 8 h apart. As a normoglycemic control, one group of mice received no STZ treatment and was not fed commensal bacteria (Control). Mouse random glucose levels (FIG. 9B) and weights (FIG. 9C) were monitored over 80 days. β cell mass was measured (FIG. 9A). Feeding of Nissle alone had no significant effect on random blood glucose levels when compared with the STZ-treated mice given no commensal bacteria (FIG. 9B). However, mice fed Nissle-GLP-1 exhibited significantly lower random blood glucose levels within 16 days of beginning feeding. There was no significant difference in weight for any of the mice in the study and there was no significant weight gain for any of the mice over the 80 day time period.

Figure 9E:
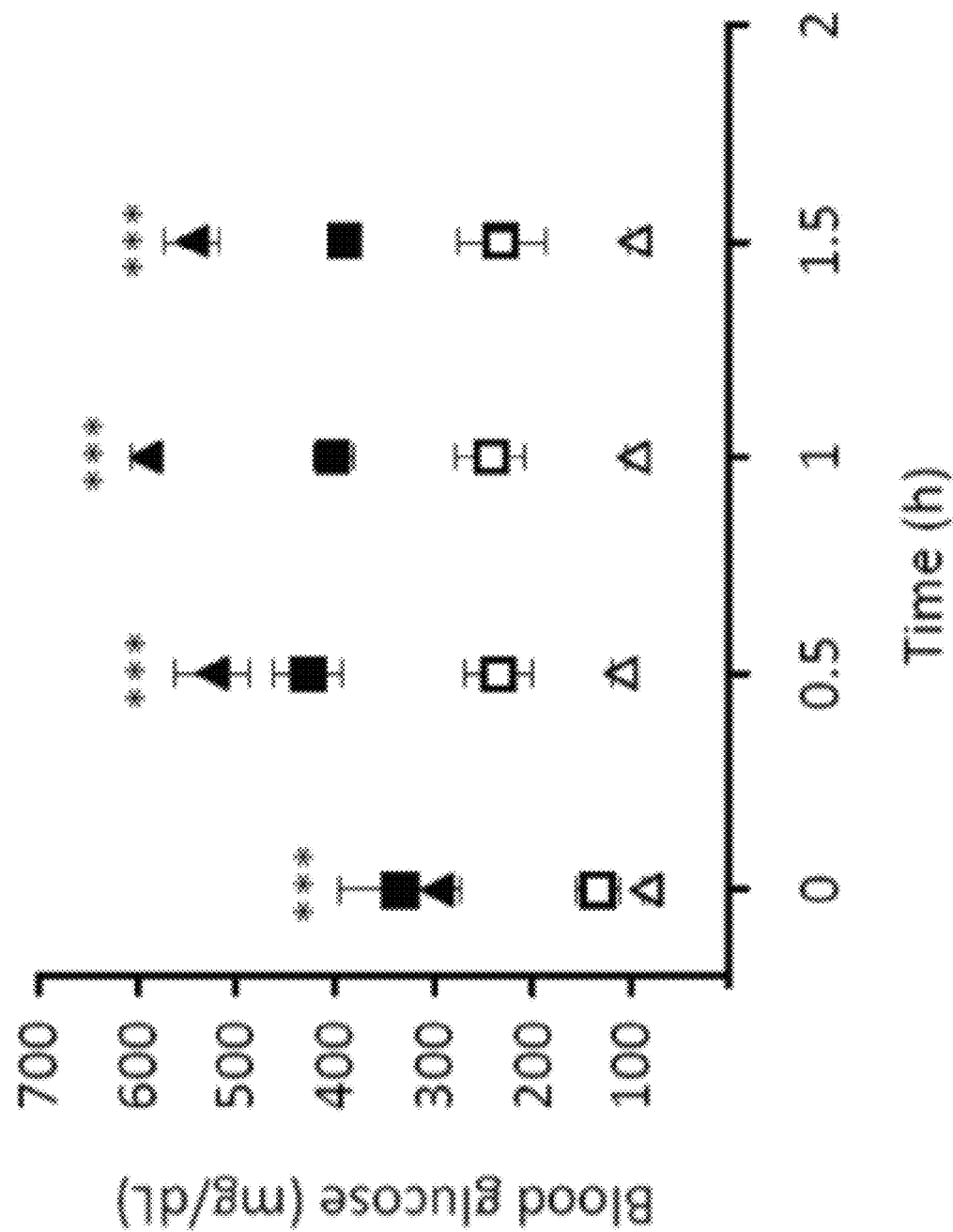

After 89 days of commensal bacterial treatment, mice were subject to a glucose tolerance test. They were fasted for 10 h prior to being injected with glucose i.p. Blood insulin and glucose levels were measured every 30 minutes for 1.5 h post-glucose injection (FIGS. 9D and 9E, respectively). Significant differences in insulin levels were seen between Nissle-GLP-1-fed mice and STZ-only mice at 0.5 and 1.5 h. There was no significant difference in insulin levels between Nissle GLP-1-fed mice and Control mice receiving no treatment at any time point (FIG. 9D). There were significant differences in blood glucose levels throughout the experiment between all 4 groups of mice. Nissle-GLP-1-fed mice exhibited less than 50% of the blood glucose levels of STZ-only mice throughout the glucose tolerance test; but had twice as high blood glucose levels as control mice given no STZ (FIG. 9E). Interestingly, although the Nissle-treated mice had no significant difference in blood glucose from STZ-treated mice before glucose was injected (time=0), 1 h post-glucose injection the Nissle-treated mice exhibited close to 33% lower blood glucose levels than STZ-treated mice.

Mouse intestines were immuno-stained for the presence of insulin (FIGS. 10A-F). Pockets of insulin containing cells were found in mice treated with Nissle-GLP-1 but not with any other mice used in the study. The relative frequency of these pockets is shown (FIG. 10A-B). As a percentage of overall epithelial cell mass, it is estimated that the pockets comprised less than 1% (FIG. 10B). STZ was effective at eliciting a T1DM response as expected. β-cell mass was significantly lower for STZ-treated mice (FIG. 9A) and their blood glucose and insulin levels were also in line with T1DM (FIGS. 9B, D, E). That the β-cell mass was equally reduced for all STZ-treated mice indicated that pancreatic β-cell regeneration was not the mechanism for increasing insulin or lowering blood glucose in mice fed Nissle-GLP-1.

To determine which types of enterocytes (paneth, absorptive, goblet or enteroendocrine) may have been reprogrammed to become insulin-containing cells, cells were co-stained blue with antibodies against representative proteins from each of the 4 cell types: NOD-2 for paneth cells, mucin-2 (MUC-2) for goblet cells, sucrose isomaltase (SI) for absorptive cells, and chromogranin A (Chr-A) for enteroendocrine cells. Overlapping stains were not seen for NOD-2, MUC-2, or SI (FIGS. 10C, D and E, respectively). However, overlapping staining with insulin was seen for Chr-A (FIG. 10F) Immuno-staining of mouse intestines revealed insulin-containing cells in mice fed Nissle-GLP-1 (FIG. 10A) and not in Nissle-fed or Control mice (FIG. 10B). Co-staining with antibodies to representative proteins from each of the four types of enteric cell suggested that the lineage of these cells is related to enteroendocrine cells (FIG. 10F). This result was anticipated as the secretion of hormones into the blood is normally a function of enteroendocrine cells and not the other three cell types.

Healthy mice (non-STZ treated) were also fed Nissle and Nissle-GLP-1 and their blood glucose levels were not significantly different from those of healthy mice fed no commensal bacteria (FIGS. 11A-B). The results indicate that there is no significant change in random mouse blood glucose levels over a period of 94 days between either of the treatments and the healthy mice given no treatment (Control) (FIG. 11A). There was also no difference in mouse weight changes over this time (FIG. 11B). Considering the data indicating no change in blood glucose or weight for healthy mice fed Nissle-GLP-1 (FIG. 11) alongside the data indicating Nissle-GLP-1 can significantly reduce blood glucose levels, the overall picture is one of an effective and safe potential treatment for diabetes: one that is glucose responsive with similar insulin kinetics to non-diabetic systems (FIG. 9D). That is, the insulin level changes happen with the same timing in Nissle-GLP-1-fed mice as they do in healthy mice, albeit to a lesser extent.

These data suggest that feeding Nissle-GLP-1 to diabetic mice can cause glucose-responsive insulin production, reducing blood glucose levels significantly. Without wishing to be bound by theory, the mechanism of insulin secretion seems to be from pockets of reprogrammed intestinal cells. These pockets express Chr-A in addition to insulin, suggesting they are derived from enteroendocrine cells. When considered with results from healthy mice fed Nissle-GLP-1, the evidence suggests that this treatment would be safe, even if taken by non-diabetics.

6.7. Example 7

Expression of GLP-1 in Chromosomally Modified Versus Plasmid-Containing E. coli Nissle This example describes the comparison of expression of GLP-1 in chromosomally modified versus plasmid-containing E. coli Nissle.

Bacteria were engineered that required no selective pressure to maintain GLP-1 expression. In comparing strains, it was found that the relative concentration of GLP-1 secreted into the culture media from chromosomally modified Nissle was less than that secreted from Nissle expressing GLP-1 from a plasmid. However, it appeared that Nissle expressing GLP-1 from the chromosome was as effective in vivo as Nissle expressing GLP-1 from a plasmid (FIG. 5). There may be several reasons for a lack of correlation between amounts of GLP-1 secreted in bacterial culture and lowered blood glucose levels in vivo. Measurement of Nissle survivability in the mouse intestines revealed no difference between strains fed Nissle, Nissle expressing GLP-1 from a plasmid or Nissle-GLP-1 (FIG. 12). GLP-1 stability in the intestinal mucosa may have been compromised by mucosal proteases, making the effective transport far lower than the secretion rate. It may have also been the case that the less-than-ideal growing conditions (pH, nutrients, etc.) within a mouse gut (Nissle is a human probiotic) led to less than optimal gene expression for either strain.

The kinetics of insulin secretion in the glucose response test appeared to be similar for Nissle-GLP-1-fed mice and Control mice (FIG. 9D); although blood glucose lowering was delayed in all of the mice treated with STZ (FIG. 9E). Nissle-fed mice, however, displayed identical kinetics to Control mice. This result was unexpected and may be explainable by another mechanism. Also unexpected was the more rapidly lowered blood glucose in the glucose response test for Nissle-fed mice when compared to STZ-only mice (FIG. 9E). This implies a level of protection from Nissle alone. While this protection was not apparent in random glucose levels it appears to lessen the effects of a spike in blood glucose. Seeing as the glucose was injected i.p., bacterial consumption of enteric glucose could be ruled out as a possible mechanism.

6.8. Example 8

Effects of Feeding Nissle on Blood Glucose Levels

This example demonstrates the effects of feeding Nissle on blood glucose levels in mice.

Mice were fed with STZ for 5 days (40 mg per kg body weight) at the beginning of the experiment (STZ treatment ending at "STZ stop"). Following the onset of sustained random blood glucose levels over 300 mg/dL, mice were started with Nissle treatments including either Nissle by itself expressing a dummy plasmid (STZ+vector), Nissle expressing GLP-1(1-37) from the same plasmid (STZ+GLP) or no treatment and no STZ (Control). Feeding is marked on the timeline as "Nissle start." Nissle was fed twice daily until the time demarked "Nissle stop." Mice were essentially left alone at this point (outside of ordinary care) until the time demarked "Nissle once." At that point blood glucose was measured and Nissle was fed to mice once. Mice were then left alone until the last time point when blood glucose was measured. See FIG. 13. Averages are presented (n=3) with error bars representing 1st. dev.

Non-obese diabetic (NOD) mouse were fed twice daily with either Nissle by itself, Nissle expressing GLP-1 (1-37) chromosomally or given no treatment. Mice were fasted for 4 hours just before blood glucose was measured. Referring to FIG. 14, times indicate days after treatment started. Averages are presented (n=at least 3) with error bars representing $1^{st}$ dev. p values are from a student's t-test.

FIG. 15 illustrates the likely method of operation of the recombinant cell. Left: normal intestinal crypt with bacteria in lumen B in and on top of the mucosa M. Enteroendocrine cells (E) secrete hormones into the lamina propria (LP) and vasculature V. Right: recombinant cells of embodiments herein (EB) secrete GLP-1 (dots emerging from EB) into the crypts to reprogram early enteroendocrine cells into insulin-secreting cells (RE). Insulin (Ins, stars) is then secreted into the bloodstream in response to glucose.

Without wishing to be bound by theory, it is believed that the use of recombinant commensal strains, with simple oral dosing, no significant background expression, and glucose responsiveness, may significantly reduce or even eliminate the need for insulin injection and could help to reduce the long-term complications exhibited by diabetics by replacing host insulin synthesis.

6.9. Example 9

Sequences of Original and New Constructs for GLP-1 Studies

The following constructs can be used according to the methods disclosed herein.

Original Nissle-GLP-1 Construct Used in Examples 1-11

```
(FliC promoter)---Flic20-6xhis-xpress-EK site-glp-
1(1-37)-cpp
                                      (SEQ ID NO: 4)
atggcacaagtcattaataccaacagcctctcgctgatcactcaaaataa tatcaacaagATGCATCATCATCATCATCACGGATCCGATCTGTACGACG

ATGACGATAAGCACGATGAATTTGAGAGACATGCTGAAGGGACCTTTACC

AGTGATGTAAGTTCTTATTTGGAAGGCCAAGCTGCCAAGGAATTCATTGC

TTGGCTGGTGAAAGGCCGAGGAtgcggtggcggttacggccgtaaaaaac gtcgtcagcgccgtcgcTAA

Where:
FliC20:
                                      (SEQ ID NO: 5)
ATGGCACAAGTCATTAATACCAACAGCCTCTCGCTGATCACTCAAAATAA

TATCAACAAG

6XHis:
                                      (SEQ ID NO: 6)
ATGCATCATCATCATCATCACGGATCC

Xpress:
```

```
GATCTGTAC

EK site:
                                        (SEQ ID NO: 7)
GACGATGACGATAAG

GLP1(1-37):
                                        (SEQ ID NO: 8)
CACGATGAATTTGAGAGACATGCTGAAGGGACCTTTACCAGTGATGTAAG

TTCTTATTTGGAAGGCCAAGCTGCCAAGGAATTCATTGCTTGGCTGGTGA

AAGGCCGAGGA

CPP:
                                        (SEQ ID NO: 9)
TGCGGTGGCGGTTACGGCCGTAAAAAACGTCGTCAGCGCCGTCGCTAA
```

Another Promoter Nissle-GLP-1 Construct that can Used

```
LPP Promoter---5'UTR-Flic20-6xhis-xpress-EK site-
GLP-1(1-37)-CPP-3'UTR
                                       (SEQ ID NO: 10)
TGCATGCATccatcaaaaaaataTTCTCAacataaaaaactttgtgtAAT

ACTCAGGGTTGACGGCGATTGAGCCGACGGGTGGAAACCCAATACGTAAT

CAACGACTTGCAATATAGGATAACGAATCatggcacaagtcattaatacc aacagcctctcgctgatcactcaaaataatatcaacaagctcgagCATCA

TCATCATCATCACGGATCCGATCTGTACGACGATGACGATAAGCACGATG

AATTTGAGAGACATGCTGAAGGGACCTTTACCAGTGATGTAAGTTCTTAT

TTGGAAGGCCAAGCTGCCAAGGAATTCATTGCTTGGCTGGTGAAAGGCCG

AGGAtgcggtggcggttacggccgtaaaaaacgtcgtcagcgccgtcgcT

AATCGTCGTAAACTGATTAACTGAGACTGACGGCAACGCCAAATTGCCTG

ATGCGCTGCGCTTATCAGGCCTACAAGGTGAATTGCAATTTATTGAATTT

GCACATTTTTGTAGGCCGGATAAGGCGTTTACGCCGCATCCGGCAACATG

AATGGTAATTTGTCAGCAACGTGCTTCCCCGCCAACGGCGGGGTTTTTTC

TGCCCGCAATTTACCGATAACCCCCAAATAACCCCTCATTTCACCCACTA

ATCGTCCGATTAAAAACCCTGCAGAAACGGATAATCATGCCGATAACTCA

TATAACGC

Where:
LPP PROMOTER:
                                       (SEQ ID NO: 11)
TGCATGCATCCATCAAAAAAATATTCTCAACATAAAAAACTTTGTGTAAT

ACT

5'UTR:
                                       (SEQ ID NO: 12)
CAGGGTTGACGGCGATTGAGCCGACGGGTGGAAACCCAATACGTAATCAA

CGACTTGCAATATAGGATAACGAATC

FliC20:
                                       (SEQ ID NO: 13)
ATGGCACAAGTCATTAATACCAACAGCCTCTCGCTGATCACTCAAAATAA

TATCAACAAG

6XHis:
                                       (SEQ ID NO: 14)
ATGCATCATCATCATCATCACGGATCC

Xpress:
GATCTGTAC
```

```
EK site:
                                       (SEQ ID NO: 15)
GACGATGACGATAAG GLP1(1-37):
                                       (SEQ ID NO: 16)
CACGATGAATTTGAGAGACATGCTGAAGGGACCTTTACCAGTGATGTAAG

TTCTTATTTGGAAGGCCAAGCTGCCAAGGAATTCATTGCTTGGCTGGTGA

AAGGCCGAGGA

CPP:
                                       (SEQ ID NO: 17)
TGCGGTGGCGGTTACGGCCGTAAAAAACGTCGTCAGCGCCGTCGCTAA

3'UTR:
                                       (SEQ ID NO: 18)
TCGTCGTAAACTGATTAACTGAGACTGACGGCAACGCCAAATTGCCTGAT

GCGCTGCGCTTATCAGGCCTACAAGGTGAATTGCAATTTATTGAATTTGC

ACATTTTTGTAGGCCGGATAAGGCGTTTACGCCGCATCCGGCAACATGAA

TGGTAATTTGTCAGCAACGTGCTTCCCCGCCAACGGCGGGGTTTTTCTG

CCCGCAATTTACCGATAACCCCCAAATAACCCCTCATTTCACCCACTAAT

CGTCCGATTAAAAACCCTGCAGAAACGGATAATCATGCCGATAACTCATA

TAACGC
```

*Lactobacillus* Construct

```
TAA-SLPAP-RBS-ATG--USP45-LEISS-6XHIS--EK-GLP
(1-37)-CPP-TAA-TAA-TERM667
                                       (SEQ ID NO: 19)
TAACCCGGGGGAGTATAACAGAAACCTTAAGGCCCGACCGCTTGACAAG

GGCGCGTGAGGTTTTTACGATAGCGCCGGATGCGGGGAAAAAGGGCTCCT

TTTGGGGGTTTTCCCCGCACCGGGCGGACCTGGGCGGAGagGAAACGcg

GCAACTCGCCCGTCTCGGGTTCCCGCCCACGACCCTTAAGGAGGTGTGAG

GCATATGAAAAAAAAGATTATCTCAGCTATTTTAATGTCTACAGTGATAC

TTTCTGCTGCAGCCCCGTTGTCAGGTGTTTACGCTGATACTAATTCTGAT

TTGGAAATATCGTCGACTTGTGATGCTCATCATCATCATCACGACGA

TGACGATAAGCACGATGAATTTGAGAGACATGCTGAAGGGACCTTTACCA

GTGATGTAAGTTCTTATTTGGAAGGCCAAGCTGCCAAGGAATTCATTGCT

TGGCTGGTGAAAGGCCGAGGAtgcggtggcggttacggccgtaaaaaacg tcgtcagcgccgtcgcTAAtaaAAATAACAAAAAGAGTATGAGTTTTTGC

TCATACTCTTTTTGTTATTT

Where:
TAA-SLPAP-RBS:
                                       (SEQ ID NO: 20)
TAACCCGGGGGAGTATAACAGAAACCTTAAGGCCCGACCGCTTGACAAG

GGCGCGTGAGGTTTTTACGATAGCGCCGGATGCGGGGAAAAAGGGCTCCT

TTTGGGGGTTTTCCCCGCACCGGGCGGACCTGGGCGGAGAGGAAACGCG

GCAACTCGCCCGTCTCGGGTTCCCGCCCACGACCCTTAAGGAGGTGTGAG

GCAT

ATG-USP45:
                                       (SEQ ID NO: 21)
ATGAAAAAAAAGATTATCTCAGCTATTTTAATGTCTACAGTGATACTTTC

TGCTGCAGCCCCGTTGTCAGGTGTTTACGCTGATACTAATTCTGAT
```

-continued

LEISS:
(SEQ ID NO: 22)
TTGGAAATATCGTCGACTTGTGATGCT

6XHIS:
(SEQ ID NO: 23)
CATCATCATCATCATCAC

EK site:
(SEQ ID NO: 24)
GACGATGACGATAAG

GLP-1(1-37):
(SEQ ID NO: 25)
CACGATGAATTTGAGAGACATGCTGAAGGGACCTTTACCAGTGATGTAAG

TTCTTATTTGGAAGGCCAAGCTGCCAAGGAATTCATTGCTTGGCTGGTGA

AAGGCCGAGGA

CPP:
(SEQ ID NO: 26)
TGCGGTGGCGGTTACGGCCGTAAAAAACGTCGTCAGCGCCGTCGCTAATA

ATAA

TERM667:
(SEQ ID NO: 27)
AAATAACAAAAAGAGTATGAGTTTTTGCTCATACTCTTTTTGTTATTT 6.10. Example 10

Commensal Bacterially-Secreted GLP-1 Reprograms Intestinal Cells to Reduce Hyperglycemia in Diabetic Mice Feeding bacterially-secreted GLP-1 intestinally to diabetic mice can cause glucose-responsive insulin production, reducing blood glucose levels significantly. The mechanism of insulin secretion appears to be from reprogrammed intestinal cells. These cells are distinct from the majority of pancreatic β-cells in that they express little PDX-1 and only some express ChrA in addition to insulin.

Introduction

Glucagon like peptide 1 (GLP-1) stimulates conversion of mouse intestinal epithelial cells into insulin secreting cells. We investigated if simple oral dosing of human commensal bacterial strains engineered to secrete GLP-1 could ameliorate hyperglycemia in a mouse model of type 1 diabetes mellitus (T1DM) by reprogramming intestinal cells into glucose-responsive insulin-secreting cells. Diabetic mice were fed daily with commensal bacteria engineered to secrete GLP-1 (Nissle-GLP-1). Nissle-GLP-1-fed mice showed significantly increased insulin levels and were significantly more glucose-tolerant. These mice developed insulin-producing cells within the upper intestine in numbers sufficient to replace approximately 82% of the pancreatic β-cells found in healthy mice. Surprisingly, expression of PDX-1 was qualitatively lower in reprogrammed cells than in surrounding epithelia. Further, a subset of the reprogrammed cells co-stained for chromogranin A (ChrA, a marker for enteroendocrine and β cells). Healthy (non-diabetic) mice fed Nissle-GLP-1 exhibited similarly reprogrammed cells, but had no change in blood glucose levels and gained weight in a manner indistinguishable from control mice, even after more than 90 days of treatment. These results point to a potential oral treatment for T1DM and introduce the concept of bacterial signaling to mediate enteric cell fates.

Reprogramming non-β cells into β-cells or cells with insulin secreting potential has been the subject of several studies over the last decade. Research has focused on a number of areas including in vitro generation of β-cells from pancreatic (acinar cells, etc.) and liver cell lineages for transplantation as well as causing either pancreatic or other tissue-specific cells to convert to β-cells in vivo. The discovery that a form of glucagon like peptide 1 previously thought to be inactive (GLP-1(1-37)) could stimulate rat intestinal epithelial cells to become glucose-responsive insulin-secreting cells through the Notch signaling pathway (Suzuki, A., Nakauchi, H. & Taniguchi, H. Glucagon-like peptide 1 (1-37) converts intestinal epithelial cells into insulin-producing cells. Proc Natl Acad Sci USA 100, 5034-5039 (2003)) demonstrated the potential of this latter approach. Suzuki reported that developing rat embryos whose mothers were injected intraperitoneally (i.p.) with GLP-1 on embryonic day 10.5 (E10.5) would exhibit several insulin producing cells in their upper intestines. Adult rats (10 weeks) had some (although far fewer) intestinal insulin producing cells when injected daily with GLP-1 for 9 days. This suggested that rats with undifferentiated intestinal epithelia (differentiation occurs in rats after E15) would be able to differentiate intestinal cells into "β-like" cells. The study also demonstrated that embryonic jejunums (E14.5) incubated with GLP-1 in vitro and surgically implanted into adult diabetic rats could reverse STZ-induced T1DM. The authors concluded that adult enterocyte differentiation (which occurs from the intestinal crypts) would not give rise to significant numbers of insulin-producing cells and that the proliferating and pseudostratified cells of the developing fetus (pre-E17) would likely be required for significant differentiation into cells with β-like functionality.

The Suzuki work demonstrated the difficulty in delivering, without surgery, bioactive compounds that can mediate reprogramming of intestinal cells. GLP-1 itself has a half-life of only a few minutes in the blood. This short half-life may have been the reason for lower reprogramming rates in adult rats, where GLP-1 would have to survive long enough in circulation to reach intestinal crypts. One method of delivering bioactive compounds to the luminal (villous) side of the upper intestine that avoids the potential pitfalls of surgery or degradation in the bloodstream is the secretion of signals from commensal bacteria populating the intestine. This approach allows for expression of signals continuously or in response to a local stimulus with the subsequent transport being through the intestinal mucosa and not the blood.

Engineered commensal bacteria can deliver GLP-1(1-37) to human intestinal cells and stimulate glucose-responsive insulin secretion in vitro (Duan, F., Curtis, K. L. & March, J. C. Secretion of insulinotropic proteins by commensal bacteria: rewiring the gut to treat diabetes. Appl Environ Microbiol 74, 7437-7438 (2008)). In that work E. coli Nissle 1917 (EcN) was transformed to secrete GLP-1(1-37) from a plasmid in response to an exogenous inducer. In this investigation we tested whether EcN chromosomally modified to secrete GLP-1(1-37) constitutively (Nissle-GLP-1) could restore euglycemia in a mouse model of T1DM. Our objective was to reprogram mouse intestinal cells into glucose-responsive insulin-secreting cells through daily feeding of Nissle-GLP-1. We also measured co-expression of β-cell and enteroendocrine markers to determine the extent of reprogramming as well as the lineage of the reprogrammed cells.

Figure 16C:
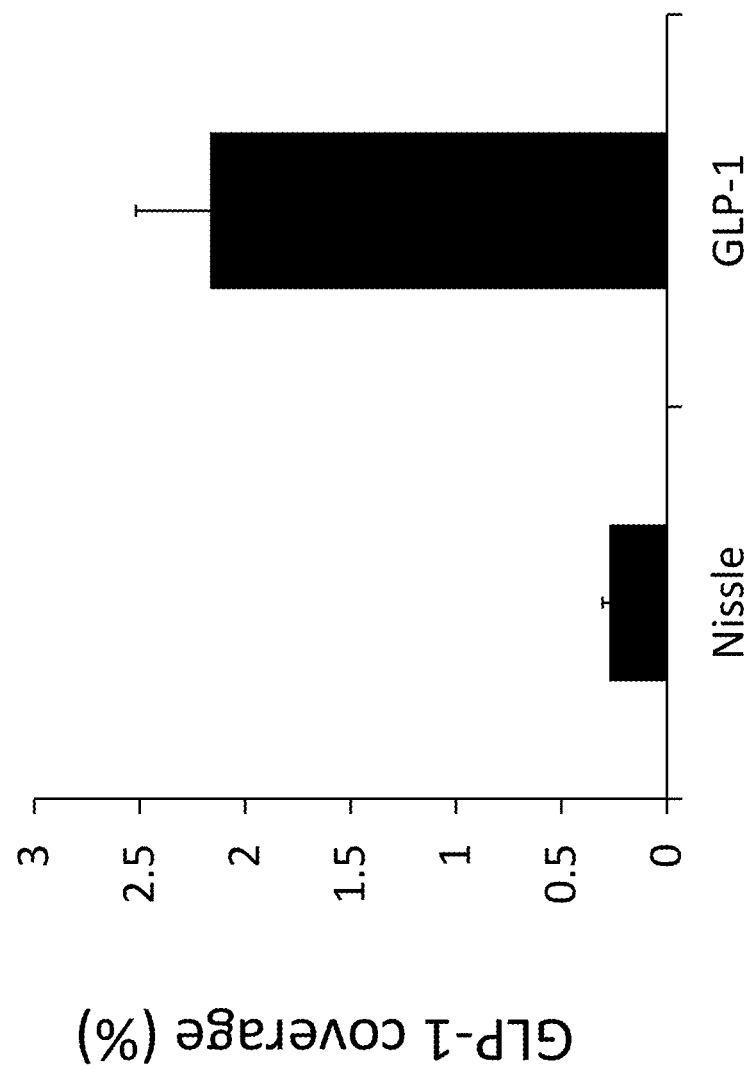

EcN was engineered to secrete GLP-1(1-37) using the fliC promoter, a cell penetrating peptide (CPP) and secretion tag (FIG. 19, top). Secretion of GLP-1 was verified in culture for this strain and compared to secretion from a plasmid-bearing strain that contained the same sequence without the pKD3 chromosomal insertion cassette (FIG. 19, bottom). Secreted amounts for Nissle-GLP-1 were approximately 50% that of the plasmid-bearing strain. We therefore used Nissle-GLP-1 for in vivo studies rather than the plasmid bearing strain as the yield difference was not considered significant and we did not want to include selective pressure for plasmid maintenance in these experiments. Mice fed Nissle-GLP-1 stained positive for GLP-1 in their upper intestines as revealed by immunofluorescence (IF), while mice fed EcN expressing a "dummy" peptide (Nissle) did not exhibit similar staining (FIGS. 16a, b). In order to preserve the mucous layer, intestinal sections were frozen rather than fixed in paraformaldehyde. Image analysis indicated that GLP-1 staining was significantly higher in mice fed Nissle-GLP-1 than in Nissle-fed mice (FIG. 16c).

We measured bacterial counts in the intestine and the feces of mice fed Nissle-GLP-1 or Nissle. The intestinal and fecal bacterial counts of Nissle-GLP-1 and Nissle-fed mice were the same (FIG. 16d), indicating that the observed increase in GLP-1 for Nissle-GLP-1-fed mouse sections was likely from recombinant GLP-1 expression and not from endogenous GLP-1 production brought about by the presence of EcN-derived strains. To determine the colonies in the large bowel not within the feces, lower GI tract sections were gently scraped and washed to remove feces. Counts are given for the remaining bacteria. Our bacterial counts in the small intestine and the feces were not as high as have been reported elsewhere, however this could be due to a different breed of mouse and alternate antibiotic pretreatment.

We tested whether Nissle-GLP-1 can restore euglycemia in a drug-induced T1DM mouse model and a genetic non-obese diabetic (NOD) mouse model (results from the NOD model are summarized in Section 6.11 (Example 11). For the drug-induced T1DM model C57BL/6J (B6) male mice were injected with streptozotocin (STZ) at a high dose (40 or 50 mg/kg body weight) for 5 days consecutively. With onset of hyperglycemia (fasting glucose levels>250 mg/dL) mice were fed either Nissle-GLP-1, Nissle or given no treatment. Commensal bacterial feedings were carried out twice daily approximately 8 h apart. As a euglycemic control, one group of mice received no STZ treatment and was not fed commensal bacteria (Control). Blood glucose levels and weights were monitored over 60 days.

Figure 17B:
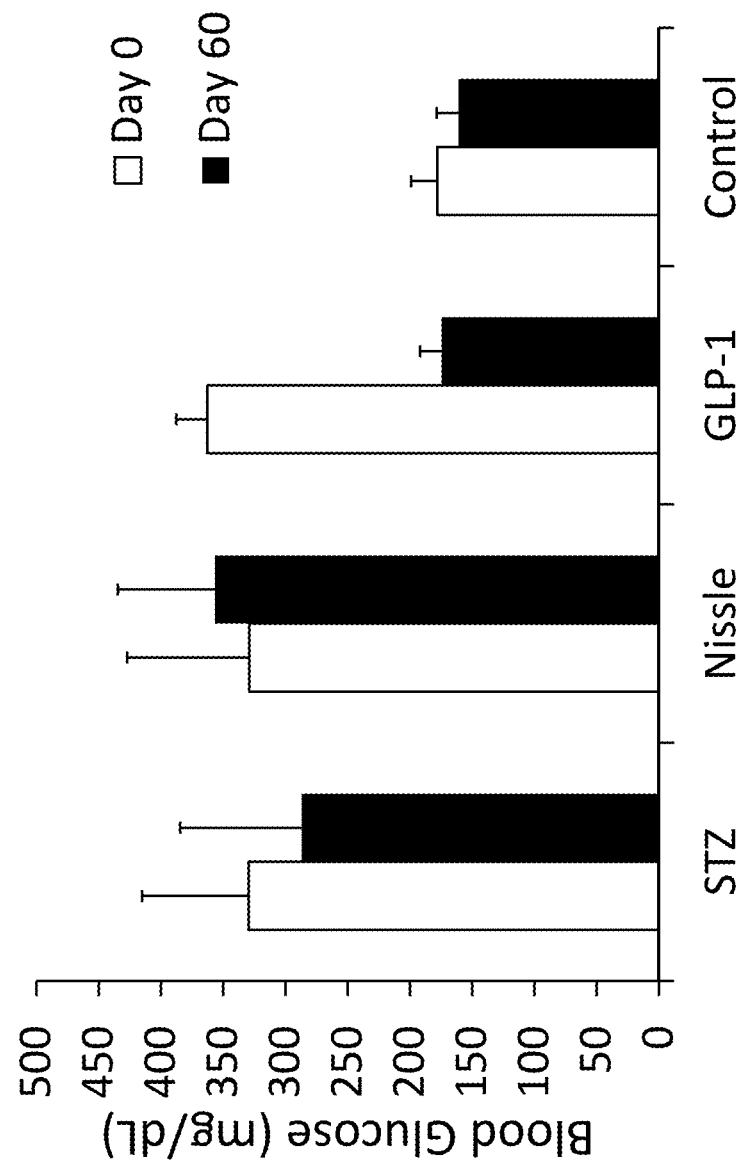

Pancreatic morphometric analysis showed that STZ-treated mice had a significantly reduced β-cell mass compared to control mice (FIG. 17a). Feeding of Nissle alone had no significant effect on blood glucose levels when compared with the STZ-treated mice given no commensal bacteria (FIG. 17b). Mice fed Nissle-GLP-1, however, exhibited significantly lower (p=0.000017) blood glucose levels after 60 days of beginning feeding (FIG. 17b). The blood glucose levels for mice fed Nissle-GLP-1 were not significantly different (p=0.46) from the euglycemic controls. Additionally, there were no significant changes in weight for any of the mice in the study over the 60 day time period (FIGS. 20A-B). That β-cell mass was equally reduced in all of the mice fed STZ ruled out the possibility that lowered blood glucose levels for mice fed Nissle-GLP-1 were the result of β-cell regeneration.

Healthy, non-STZ-treated mice were also fed Nissle and Nissle-GLP-1 and their blood glucose levels were not significantly different from those of healthy mice fed no commensal bacteria (FIG. 17c). There was no significant change in mouse blood glucose levels over a period of 92 days between either of the treatments and the healthy mice given no treatment (Control) (FIG. 17c). There was also no difference in mouse weight changes over the same time period (FIGS. 20A-B).

After 60 days of commensal bacterial treatment, all groups of mice were subjected to a glucose tolerance test. The mice were fasted for 10 h prior to being injected i.p. with glucose (25 g/kg body weight). Blood insulin and glucose levels were measured every 30 minutes for 1.5 h post-glucose injection (FIG. 17d). While significant differences in insulin levels were seen between the Nissle-GLP-1-fed mice and the STZ-only group at 0.5 and 1.5 h, no significant difference in insulin levels between Nissle GLP-1-fed mice and Control mice receiving no treatment at any time point was detected (FIG. 17d). There were significant differences in blood glucose levels throughout the glucose tolerance test across all 4 groups of mice. Nissle-GLP-1-fed mice exhibited less than 50% of the blood glucose levels of STZ-only mice throughout the glucose tolerance test; but had twice as high blood glucose levels as control mice given no STZ (FIG. 17d). Though higher than euglycemic controls, the Nissle-GLP-1-fed mice blood glucose levels did not exceed 275 mg/dL throughout the glucose tolerance test (compared to 600 mg/dL for the STZ-only mice). Interestingly, although the Nissle-treated mice exhibited no significant difference in blood glucose from STZ-treated mice at the basal level (time=0), 1 h post-glucose injection the Nissle-treated mice exhibited close to 33% lower blood glucose levels than STZ-treated mice. While this protection was not apparent in mice not injected with high levels of glucose it appears that Nissle can ameliorate to some extent the effects of a spike in blood glucose. Given that the glucose was injected i.p., bacterial consumption of glucose in the lumen could be ruled out as a possible mechanism. Further study is required in order to explain this observation.

After 60 days of treatment (and following a glucose tolerance test), sections of mouse small intestines were fixed and immuno-fluorescently probed for various markers. Pockets of insulin-containing cells were found in the small intestines of mice treated with Nissle-GLP-1 but not in any other groups used in the study (FIGS. 18a-d). The relative frequency of insulin producing cells was estimated from image analysis to be approximately 0.013% (±0.002%) of the overall small intestinal cell mass (or 1 in 10,000 epithelial cells). PDX-1 production was seen in the upper intestine as expected for all mice in the study (red staining in FIGS. 18a-d). However, insulin-producing cells in mice treated with Nissle-GLP-1 did not stain for high levels of PDX-1 and even appeared to have less PDX-1 expression than surrounding cells (FIGS. 18b and d) or than pancreatic beta cells from control mice (data not shown). While this is an interesting outcome, it still leaves open the possibility that these cells have β-cell-like functionality, since heterogeneity in PDX-1/Insulin secretion within β-cell populations is known to exist.

In longer-term control experiments in which healthy (non-diabetic) mice were fed Nissle and Nissle-GLP-1, intestines were also stained for the presence of reprogrammed cells. Insulin staining was seen in healthy mice fed Nissle-GLP-1 and PDX-1 expression was also lower in insulin-producing cells than in surrounding cells (FIG. 18d). Healthy mice fed Nissle did not exhibit reprogrammed cells (FIG. 18c).

Figure 18H:
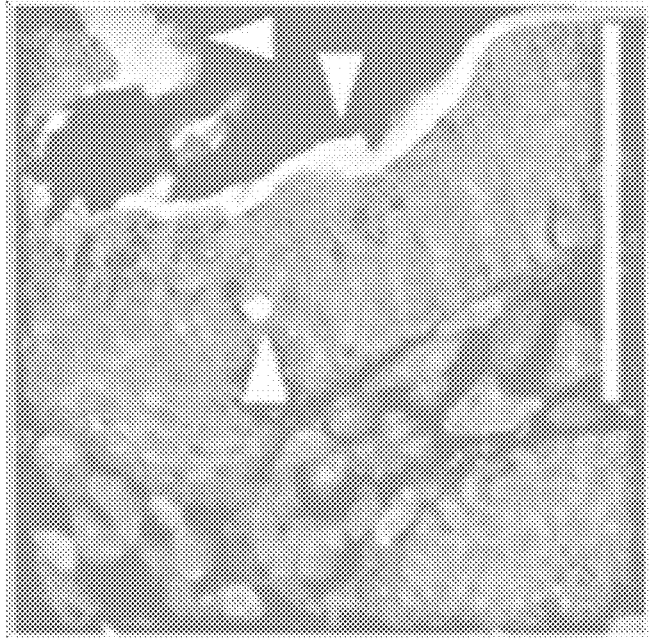
Figure 18G:
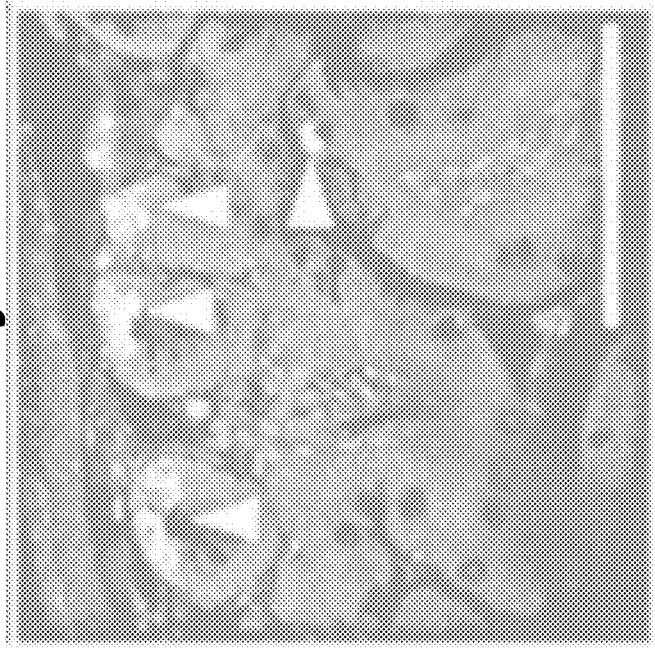

In order to better understand the physiology of the reprogrammed cells, we co-stained for chromogranin A (ChrA) and insulin in mouse intestinal sections. ChrA is normally expressed by neuroendocrine cells, enteroendocrine cells and in islet β-cells in secretory granules. In some instances insulin staining overlapped with ChrA staining (red) (FIG. 18e) and in approximately 80% of observed insulin-producing cells, ChrA did not localize to the same cell (FIG. 18O. FIGS. 18e and f show normal enteroendocrine cells (ChrA positive with no insulin staining) insulin producing (insulin staining) cells. The presence of ordinary enteroendocrine cells in close proximity to insulin producing cells suggests that enteroendocrine functionality is preserved in the whole animal despite there being some conversion of enteroendocrine cells to insulin producing cells. We observed no co-localization with insulin for lysozyme (FIG. 18g), suggesting that the reprogrammed cells were not Paneth cells. Co-expression of insulin and sucrase isomaltase (SI, FIG. 18h) indicates that reprogrammed cells maintain their absorptive capacity.

The data indicating no change in blood glucose (FIG. 17c) or weight (FIGS. 20A-B) for healthy mice fed Nissle-GLP-1 alongside the data indicating Nissle-GLP-1 can significantly reduce blood glucose levels in two rodent models of T1DM (FIGS. 17b and 21), suggests that this approach could be an effective and safe treatment for diabetes: one that is glucose responsive with similar insulin kinetics to non-diabetic systems (FIG. 17d), i.e. the insulin level changes occur with the same timing in Nissle-GLP-1-fed mice as they do in healthy mice, albeit to lower serum insulin levels. An estimate of the reprogramming efficiency achieved in this study (details in "Calculations and estimates for numbers of re-programmed cells" below) indicates that reprogrammed cells would number approximately 82% of the number of β-cells in a healthy mouse pancreas. This number potentially explains why mice were able to exhibit normalized blood glucose levels under daily conditions, but slightly less than healthy mouse glycemic control under the more challenging glucose tolerance test conditions. Estimates of the amount of bacteria that a human patient would have to consume daily to achieve the same results as presented here for mice were approximately 5-15 g daily given the amounts of bacteria present in over-the-counter probiotic formulations currently on the market. However, with higher colonization numbers, the daily intake could be as low as 50 mg.

A consideration with this approach would be the potential to elicit an immune response against the newly generated β-like cells in the intestine. There is significant potential for this to occur as it does in other regeneration approaches. However, the physiology of these cells (few express ChrA and PDX-1 expression is relatively low) is distinct from β-cells and thus these cells may go undetected by the immune system. Further, if patients were to be treated with bacteria secreting GLP-1 on a daily basis as the mice were in this study, perpetual regeneration of insulin-secreting cells would perhaps allow for continued blood glucose reduction despite immunological destruction of the newly-formed β-like cells. Considering that human epithelial cells are replaced approximately every 2 days with our data indicating a protective effect in NOD mice (who present immune destruction of pancreatic β cells) even after 46 days, there may not be a significant response by the immune system to reprogrammed cells in the upper intestine. However, if there were such an attack it could result in perpetual inflammation at the mucosal surface. More studies are needed to determine the immunological effects of this approach.

We conclude from the data presented here that feeding Nissle-GLP-1 to diabetic mice can cause glucose-responsive insulin production, reducing blood glucose levels significantly. Although more characterization is needed, the mechanism of insulin secretion appears to be from reprogrammed intestinal cells. These cells are distinct from the majority of pancreatic β-cells in that they express littlePDX-1 and only some of them express ChrA in addition to insulin. Given that mice were fed an inactive form of GLP-1 that does not stimulate β-cell insulin secretion and that mice fed Nissle-GLP-1 had the same level of pancreatic insulin production as mice fed Nissle only or mice fed no bacteria, it is unlikely that this approach led to increased insulin production from remaining β-cells. When considered with results from healthy mice fed Nissle-GLP-1, the evidence suggests that this treatment would be safe, even if taken by non-diabetics. Future work will examine more closely the physiology of the insulin-producing cells and the detailed, long-term pharmacokinetics of the treatment.

Materials and Methods
Plasmid Construction

Unless otherwise indicated all chemicals and reagents were purchased from VWR International (West Chester, Pa.). All cloning was carried out using standard techniques (Sambrook, J. & Russell, D. W. Molecular cloning: a laboratory manual. 3rd edn, (Cold Spring Harbor Laboratory Press, 2001)). A plasmid was constructed for expressing glp-1(1-37) fused to a cell-penetrating peptide (CPP) under control of the fliC promoter to make pFD-GLP as described previously (Duan, F. & March, J. C. Interrupting *Vibrio cholerae* infection of human epithelial cells with engineered commensal bacterial signaling. Biotechnol Bioeng 101(1):128-34. (2008)). The sequence 6×His-EK-glp-1(1-37)-CPP was made synthetically (IDT, Coralville, Iowa). This fragment was inserted via high fidelity PCR (Strategene) into pBluescript-KS to make pBluescript-GLP. The resultant vector contained the sequence: 5'UTR-Flic20-6×His-EK-glp-1(1-37)-CPP. This sequence was cloned into pKS121 (containing the 3'UTR of fliC) to obtain the construct: 5'UTR-Flic20-6×His-EK-glp-1(1-37)-CPP-3'UTR by high fidelity PCR. To obtain pFD-Vector, high fidelity PCR was used to clone the 5'UTR-FLIC20-6×His-EK sequence from pFD-GLP. The PCR fragment was cloned into pKS121 to obtain the construct: 5'UTR-Flic20-6×His-EK-3'UTR. pKS104 and pKS121 were kind gifts from Benita Westerlund-Wikström at the University of Helsinki, Finland.

The construct pFD-GLPC was prepared for chromosomal insertion of the glp-1(1-37)-CPP under control of the native fliC promoter using established methods (Datsenko, K. A. & Wanner, B. L. One-step inactivation of chromosomal genes in *Escherichia coli* K-12 using PCR products. Proc Natl Acad Sci USA 97, 6640-6645 (2000)). A map of the construct along with a detailed explanation of the cloning steps and primers used is set forth hereinbelow. Briefly, one-step inactivation was used to insert the Flic20-6×His-EK-glp-1(1-37)-CPP gene in place of fliC downstream of the fliC promoter region in the Nissle chromosome. We knocked out the fliD gene in the Nissle chromosome. This technique uses three plasmids, pKD3 (conferring chloramphenicol resistance), pKD4 (conferring kanamycin resistance), and pKD46 (conferring ampicillin resistance) (Datsenko, K. A. & Wanner, B. L. One-step inactivation of chromosomal genes in *Escherichia coli* K-12 using PCR products. Proc Natl Acad Sci USA 97, 6640-6645 (2000)). The resulting strain after chromosomal insertion was called Nissle-GLP-1.

Western Blot

*E. coli* Nissle 1917 (EcN) was obtained from the currently marketed probiotic Mutaflor™ as described previously (Duan, F. & March, J. C. Interrupting *Vibrio cholerae* infection of human epithelial cells with engineered commensal bacterial signaling. Biotechnol Bioeng 101(1):128-34. (2008)). EcN harboring pFD-Vector, pFD-GLP and Nissle with the chromosomal insertion from pFD-GLPC were grown in LB at 37° C. shaking at 225 rpm for 24 h. After 24 h all bacteria were centrifuged. The supernatant was filtered (0.2 μm, PALL Life Sciences). The cell-free culture medium (CFM) was diluted to the same OD600 with LB, and 10 ng/mL leupeptin, 0.04 mMPMSF and 5 ng/mL aprotinin was added to inhibit proteases. Clarified supernatant (14 mL) was precipitated with 10% trichloroacetic acid (TCA, VWR) for 30 min on ice, and the pellet was washed twice in ice-cold ethanol/ether (1:1). The supernatant pellet was dried under vacuum, dissolved in 50 μl sample buffer (2% SDS, 50 mM Tris, pH 6.8, 20% glycerol, 10% mercaptoethanol, bromophenol blue) and boiled for 5 min at 95° C. The cell pellet was resuspended (From 14 mL culture) in room temperature BugBuster Master Mix by gentle vortexing, using 500 μl BugBuster Master Mix with protease inhibitors (10 ng/mL leupeptin, 200 μMPMSF and 5 ng/mL aprotinin). The cell suspension was incubated on a shaking platform (VWR, Bristol, Conn.) at a slow setting for 10-20 min at room temperature. 125 μl 5× sample buffer was added to each sample before and boiling for 10 min at 95° C.

To estimate the amounts of GLP-1 expression and secretion, standard techniques for western blotting were used. Briefly, 50 μl samples were loaded on a polyacrylamide gel and blotted onto Immobilon-P$^{SQ}$ transfer membrane (Millipore, Billerica, Mass.). Membranes were probed with 1:1,000 for mouse anti-his (GE health, Piscataway, N.J.). The membranes were incubated with HRP-conjugated Anti-mouse IgG (Amersham Biosciences, Pittsburgh, Pa.), developed by enhanced chemiluminescence (Pierce, Rockford, Ill.) and exposed onto X-Ray film (Phoenix, Candler, N.C.).

Mouse Colonization Experiments

All mice used in this study were purchased from Jackson Laboratory (Bar Harbor, Me.) and housed at the East Campus Research Facility (ECRF) at the Cornell University Veterinary School. Studies were conducted in accordance with protocols approved by the Cornell University IACUC.

STZ-Model

Streptozotocin (STZ) (Sigma, St. Louis, Mo.) was dissolved in ice-chilled 0.1M sodium citrate buffer (pH4.2) immediately before application. Four groups of C57BL/6J (B6) male mice at 6-8 weeks age received daily intraperitoneal injections of 40 or 50 mg STZ per kg body weight on 5 consecutive days for induction of beta-cell apoptosis. Another group of mice receiving sodium citrate injection were used as controls. Three days after the last injection, animals' blood glucose level were determined by Breeze® 2 blood glucose monitoring system (Bayer Healthcare LLC Mishawaka, Ind.) with Bayer Breeze blood glucose test strips (Bayer Healthcare LLC Mishawaka, Ind.). Blood glucose levels were monitored every 3 days until diabetic glucose levels (>250 mg/dL) were reached. STZ-treated mice not reaching diabetic blood glucose levels were not used in this study.

After the establishment of hyperglycemia, mice were given chloramphenicol-treated ((1 g/liter)) drinking water for 18 h to eliminate resident facultative bacteria. Nissle strains chromosomally-modified with pED-GLPC(Nissle-GLP-1) were grown with chloramphenicol to an $OD_{600}=1$ from an overnight culture dilution 1:500 in LB media. Bacteria were collected by centrifugation at 3 min at 1000×g. The resulting pellet was redissolved in 200 μl sterile LB with 1% Sucrose. Following chloramphenicol treatment, mice were fed by 50 μl/25 g body weight of LB with 1% sucrose containing $10^9$ CFU/mL ($OD_{600}=20$) of Luria broth-grown Nissle strains separately (Nissle or Nissle-GLP-1). The bacterial volume fed was normalized by mouse body weight. All Nissle strain-fed mice were fed 2× per day with Nissle throughout the experiment. Weight and glucose levels were taken for all mice every 7 to 10 days. In most cases fasting glucose levels were measured. These measurements were spaced so as to minimize stress levels in the mice.

Glucose Tolerance Test and ELISA

Mice were fasted 10 h, weighed, and a blood sample collected from the tail vein using heparinized Micro-Hematocrit Capillary Tubes (Fisher, Pa.). They were then injected intraperitoneally with 25 mg glucose per kg body weight and blood samples were taken at 0.5, 1, 1.5 h. Plasma glucose was measured using Breeze® 2 blood glucose monitoring system. Plasma insulin was measured using Rat/Mouse Insulin ELISA kit (Millipore, Mass.) according to the manufacturer's instructions.

Bacterial Counts 6 to 8 weeks old C57BL/6J (B6) male mice were given chloramphenicol (1 g/liter) in drinking water for 18 h to eliminate resident facultative bacteria. Overnight cultures of Nissle strains (Nissle and Nissle-GLP-1) were diluted 1:500 in LB media and grown to an OD600=1. Bacteria were collected by centrifugation for 3 min at 1000×g. The resulting pellet was resuspended in sterile LB with 1% sucrose to an OD600=20. Following chloramphenicol treatment, mice were fed by oral gavage 50 μl/25 g body weight of LB with 1% sucrose containing the concentrated re-suspension (for a resultant dose of $10^9$ CFU per animal twice daily). After feeding for 20 days, mice were transferred to new cages for 3 days. Feces were collected from the new cages and mice were euthanized. At least 3 mice from each treatment were dissected and their GI tracts removed. GI tracts were cut into two pieces (Upper GI-small intestine and Lower GI-large intestine). The lower GI was opened along one side and the feces were removed by gentle scraping and washing with 1×PBS. The upper GI was not washed or scraped before weighing. The upper and lower GI tracts were each weighed and homogenized in 4 mL of fresh LB medium. Homogenized tissue was plated onto MacConkey Agar plates with corresponding antibiotics by serial dilution. Plates were incubated overnight at 37° C. and their colonies counted.

Immunohistochemistry

All treated mice used in this study were euthanized using $CO_2$ as per standard protocols. The gut and pancreas tissues of mice sacrificed after the glucose tolerance test were fixed in 4% paraformaldehyde overnight and washed three times with 1×PBS and soaked in 70% ethanol. Fixed tissues were then dissected.

After deparaffinization, fixed tissue slides were steamed in IHC-Tek™ epitope retrieval solution (IHC World, Woodstock, Md.) and immersed in 0.5% hydrogen peroxide (Fisher, Pittsburgh, Pa.) in methanol for 10 min to block endogenous peroxidase. After washing in 0.01M PBS (pH 7.2), 10% normal blocking goat serum (Invitrogen, Carlsbad, Calif.) was applied for 30 min at room temperature in a humid chamber. Rabbit anti-insulin (H-86, Santa Cruz Biotechnology) diluted 1:50 in PBS plus 1× casein (Vector, Burlingame, Calif.) was applied to blocked samples that were then incubated in a humid chamber for 1.5 h at 37° C. After 4× washing in PBS, a biotinylated secondary antibody goat Anti-Rabbit (Vector) diluted 1:200 in PBS was applied to samples for 20 min at room temperature in a humid chamber. Samples were incubated with streptavidin peroxidase (Invitrogen) for 20 min at room temperature in a humid chamber and washed 3× with PBS. Samples were incubated with AEC chromogen/substrate solution (Invitrogen) at room temperature. Color development was monitored under ordinary light microscopy for approximately 5-15 min A distilled $H_2O$ rinse was used to stop the reaction.

Some gut tissues and pancreases were counterstained with hematoxylin (Fisher) for 30 seconds before rinsing in tap $H_2O$ for 5 min. Samples were mounted using an aqueous mounting medium Fluoromount (Fisher). Pictures were taken with a color camera under an ordinary light microscope (Leica, Bannockburn, Ill.). The stained pancreas tissue pictures were analyzed by Image J software (NIH-NCBI) for the percent coverage by β-cell as estimated from red coloring.

Immunofluorescence

Paraffin Immunofluorescence—Insulin, PDX-1, ChrA, Lysozyme and SI

The gut and pancreas tissues of mice sacrificed after feeding with Nissle strains (Nissle and Nissle-GLP-1) for 60 days were fixed in 4% paraformaldehyde overnight and washed three times with 1×PBS and soaked in 70% ethanol. Fixed tissues were then dissected.

After deparaffinization, fixed tissue slides were steamed in 0.01M Citrate buffer. After washing in 0.01M PBS (pH 7.2), 10% normal blocking donkey serum (Santa Cruz Biotechnology, CA) was applied for 1 h at room temperature in a humid chamber. Rabbit anti-insulin (Santa Cruz Biotechnology, CA) diluted 1:50 and either goat anti-PDX-1 (Abcam, Cambridge, Mass.) 1:500 in PBS plus 1× casein (Vector, Burlingame, Calif.), 1:50 diluted anti-goat ChrA, anti-goat lysozyme, or anti-goat sucrase isomaltase (SI)(Santa Cruz Biotechnology, CA) was applied to blocked samples that were then incubated in a humid chamber overnight at 4° C. After 4× washing in PBS, a fluorochrome-conjugated secondary antibody Alexa Fluor® 488 donkey anti-rabbit IgG and Alexa Fluor® 555 donkey anti-goat IgG (Invitrogen) diluted 1:200 in PBS was applied to samples for 1.5 h at room temperature in a humid chamber. After 3× washing in PBS, 300 nM DAPI staining solution (Invitrogen) was allowed to incubate with the samples for 3 minutes. Samples were then mounted with ProLong® Gold antifade reagent (Invitrogen). Specimens were examined immediately using the appropriate excitation wavelength for each fluorophore. Images were taken with a Zeiss 710 Confocal Microscope (Zeiss, Jena, Germany).

Cryosection Immunofluorescence—Glp-1

Intestines and pancreases of mice fed with Nissle strains for 10 days were harvested, snap frozen in OCT compound, and cryosectioned (8 μM). Slides were air-dried 1 h and fixed in ice-cold acetone for 5 min. After air drying overnight, slides were washed 3× washing in PBST (0.05% Tween). The following protocol was modified from M.O.M.™ kit staining procedure (Vector). Cells were permeabilized with 0.1% Triton X-100 for 15 min followed by 2× wash in PBS. 10% normal donkey serum (Santa Cruz Biotechnology, CA) in working solution of M.O.M.™ Ig blocking reagent was applied for 1 h at room temperature in a humid chamber. Sections were washed 2× for 2 min each in PBS. Tissue sections were incubated for 5 min in a working solution of M.O.M.™ diluent. Samples were then incubated with rabbit anti-GLP-1(1-19) (Abcam) 1:100 in M.O.M.™ diluent at 37° C. for 30 min followed by RT for 30 min. After a 2× wash in PBST followed by a 4× wash in PBS, a fluorochrome-conjugated secondary antibody Alexa Fluor® 488 donkey anti-rabbit IgG and an Alexa Fluor® 555 donkey anti-goat IgG (Invitrogen) diluted 1:200 in PBS was applied to samples for 1 h at room temperature in a humid chamber. After subsequent washing 3× in PBST, samples were incubated in 300 nM DAPI staining solution (Invitrogen) for 3 minutes. Samples were rinsed 3× in PBS and mounted with ProLong® Gold antifade reagent (Invitrogen). Specimens were examined immediately using the appropriate excitation wavelength for each fluorophore. Pictures were taken with a Zeiss 710 Confocal Microscope.

Calculations and Estimates for Numbers of Re-Programmed Cells

Calculations for Determining the Number of Re-Programmed Cells in Mice Fed Nissle-GLP-1

Assuming $1 \times 10^6$ beta cells per mouse (Bock, T., Svenstrup, K., Pakkenberg, B. & Buschard, K. Unbiased estimation of total beta-cell number and mean beta-cell volume in rodent pancreas. Apmis 107, 791-799 (1999) and $1.9 \times 10^7$ cells/cm$^2$ in the upper intestine (Cheng, H. & Bjerknes, M. Cell production in mouse intestinal epithelium measured by stathmokinetic flow cytometry and Coulter particle counting. Anat Rec 207, 427-434, doi:10.1002/ar.1092070305 (1983), we multiplied the estimated surface area of a mouse upper intestine (duodenum+jejunum, 332.4 cm$^2$, see Casteleyn, C., Rekecki, A., Van der Aa, A., Simoens, P. & Van den Broeck, W. Surface area assessment of the murine intestinal tract as a prerequisite for oral dose translation from mouse to man. Lab Anim 44, 176-183, doi:10.1258/la.2009.009112 (2010)) by the estimated percentage of reprogrammed cells (0.00013) and this by the cells/cm$^2$ to get an estimate of reprogrammed cells of approximately 82% of the number of beta cells in a healthy mouse.

Calculations for Estimating Dose Based on Mouse Experiments

We fed mice with $10^9$ cfu/mL 2× per day in the experiments reported in this example. That equates to $8 \times 10^{10}$ CFU/kg of mouse weight. Given a probiotic supplement of $4.0 \times 10^{11}$ CFU/g as is commercially available and assuming a human weight range of 25 kg for a child to 75 kg for an adult, this would mean a daily dose of 5-15 g/d. However, if the colonization efficiency was 2 orders of magnitude higher (as has been reported, see Rao, S. et al. Toward a live microbial microbicide for HIV: Commensal bacteria secreting an HIV fusion inhibitor peptide. Proc Natl Acad Sci USA 102, 11993-11998 (2005)) then the dose would be 50-150 mg/d.

6.11. Example 11

Effect of Feeding Commensal Bacteria Secreting GLP-1 to Non-Obese Diabetic (NOD) Mice This example demonstrates the effect of feeding commensal bacteria secreting GLP-1 (1-37) to genetically-realized diabetic mice (non-obese diabetic, NOD). We fed NOD mice either *E. coli* Nissle 1917 expressing a dummy peptide (Nissle), Nissle secreting GLP-1(1-37) (Nissle-GLP-1) or media containing no bacteria for 46 days. The results were significantly reduced blood glucose levels in mice fed Nissle-GLP-1 when compared to a control NOD mouse fed media only (p=0.0003) or fed Nissle (p=0.0008). Further, Nissle-GLP-1 mice were observed to have much lower urine output. Nissle-fed mice also exhibited significantly lower blood glucose levels than mice fed media only (p=0.01). Nissle-fed and control mice in this study were unhealthy in appearance and had blood glucose levels over 400 mg/dL routinely, while blood glucose levels for Nissle-GLP-1-fed mice (who also appeared unhealthy) were in the range of 160-250 mg/dL throughout the 46-day period.

Introduction

Considered one of the standard model organisms for the study of type-1 diabetes (T1DM), the NOD mouse carries genetic defects that result in destruction of pancreatic beta cells as well as other endocrine systems throughout the body. The off-target effects make it less than ideal for studying T1DM as it carries other systemic pathologies in addition to a T1DM-like pathology. Despite this limitation, it is still regarded in the art as a sufficient model of early-stage proof of concept work.

For this example, the use of commensal bacteria to deliver the peptide GLP-1(1-37) to intestinal epithelial cells was investigated for its effect on blood glucose levels in NOD mice.

Experimental Procedures

NOD female mice (NOD/ShiLtJ mice) used in these experiments were treated in accordance with protocols approved by the Cornell University IACUC. All mice were housed at the East Campus Research Facility (ECRF) at the Cornell University Veterinary School. All mice were purchased from Jackson Laboratory (Bar Harbor, Me.). Three groups of 6-week-old NOD/ShiLtJ female mice (n=5) had their blood glucose levels monitored via a Breeze® 2 blood glucose monitoring system (Baer Healthcare LLC Mishawaka, Ind.) with Bayer Breeze® blood glucose test strips (Baer Healthcare). Blood glucose levels were measured every 5 to 7 days until a diabetic glucose level (>250 mg/dL) was reached. Reaching diabetic blood glucose levels required 12 to 14 weeks. Mice that failed to reach hyperglycemic blood glucose levels were euthanized.

After the establishment of hyperglycemia, all mice were given chloramphenicol (1 g/liter) drinking water for 18 h to eliminate resident commensal bacteria. Nissle strains (Nissle, Nissle-GFP-1) were grown to an OD600=1 from an overnight culture and diluted 1:500 in LB media. Bacteria were collected by centrifugation for 3 min at 1000×g. The resulting pellet was redissolved in 200 µL sterile LB with 1% Sucrose. Following chloramphenicol-treatment, mice were fed by oral gavage 50 µL/25 g body weight of LB with 1% sucrose containing $10^9$ CFU (OD600=20) of either Nissle, Nissle-GLP-1 or no bacteria (just sterile media with sucrose). The strains were fed to mice alone, without additives. Chloramphenicol-treated water was removed from mouse gages once gavaging started. Nissle strains or sterile media with sucrose were fed via gavage twice daily for 46 days. Mouse weight and blood glucose were measured on days 11, 21, 30 and 46 following the start of bacterial feeding.

Results

NOD mice were fed 2× daily Nissle-GLP-1, Nissle or no bacteria orally for 46 days. Table 1 shows the survival and diabetes onset data for mice in the experiment. All treatments started with 5 mice each. All mice except mice fed Nissle-GLP-1 were observed to excrete high levels of urine throughout the experiment. Nissle-GLP-1-fed mice did exhibited elevated levels of urine output, but not to the extent of the other mice.

Before the feeding of Nissle strains started, all mice considered positive for hyperglycemia exhibited blood glucose levels over 500 mg/dL. Average mouse fasting (6 h) blood glucose levels per treatment are shown in FIG. 21. There was a significant blood glucose lowering between both mice that were fed Nissle and Nissle-GLP-1 and the control mice. After 46 days, Nissle feeding had a significant effect (p=0.01) versus the controls and Nissle-GLP-1 had an even more pronounced effect (p=0.0003). The difference between Nissle-GLP-1 and Nissle was also significant (p=0.0008). All comparisons were made using a student's two-tailed t-test (n=4, 3 or 2 see table 1) assuming equal variance.

There was no significant difference in mouse weights between treatments or within a treatment over the course of the experiment. Weights for all mice generally decreased over time (FIG. 22).

CONCLUSIONS

These data indicate that both Nissle and Nissle-GLP-1 can significantly reduce blood glucose levels in NOD mice. However, these data are from very small groups of mice. By 46 days there are only 2 remaining mice in each group. That being said, the blood glucose levels of mice in the Nissle-GLP-1 group are still far lower than the other two groups, indicating that any immune response the NOD mice may have mounted against any reprogrammed cells did not have an effect within this time frame.

TABLE 1

Mouse survival for this example
Table 1: Mouse survival

| Treatment | Mice in group | Mice with elevated blood glucose | Mice surviving: | | | |
|---|---|---|---|---|---|---|
| | | | 11 d | 21 d | 30 d | 46 d |
| Nissle | 5 | 4 | 4 | 3 | 3 | 2 |
| Nissle-GLP-1 | 5 | 4 | 4 | 3 | 3 | 2 |
| Control | 5 | 3 | 3 | 3 | 3 | 2 |

The present invention is not to be limited in scope by the specific embodiments described herein. Indeed, various modifications and variations of the invention in addition to those described herein will become apparent to those skilled in the art from the foregoing description and can be made to the invention without departing from the spirit and scope of the invention. Thus, it is intended that the present invention cover the modifications and variations of this invention provided they come within the scope of the appended claims and their equivalents.

All references cited herein are incorporated herein by reference in their entirety and for all purposes to the same extent as if each individual publication, patent or patent application was specifically and individually indicated to be incorporated by reference in its entirety for all purposes.

The citation of any publication is for its disclosure prior to the filing date and should not be construed as an admission that the present invention is not entitled to antedate such publication by virtue of prior invention.

What is claimed is:

1. A method of treating a mammalian host who has diabetes or metabolic syndrome comprising the step of:
    administering orally to the mammalian host a recombinant *Lactobacillus* bacterium that comprises a promoter and coding sequence that encodes GLP-1(1-37),
    wherein the promoter and coding sequence that encodes GLP-1(1-37) comprise SEQ ID NO: 19, said GLP-1(1-37) is expressed and secreted by the recombinant *Lactobacillus* bacterium in the intestine of the mammalian host, and intestinal epithelial cells of the mammalian host differentiate into glucose responsive insulin secreting cells.

2. The method of claim 1, wherein the recombinant *Lactobacillus* cell is administered in an amount of at least about $2 \times 10^{10}$ CFU/kg of the host's weight.

3. The method of claim 2, wherein the recombinant *Lactobacillus* cell is administered in an amount selected from group consisting of at least about 5 g/day to about 15 g/day, and at least about 50 mg/day to about 150 mg/day.

4. A method of treating a mammalian host who has diabetes comprising the step of:
    administering orally to the mammalian host a recombinant *Lactobacillus* bacterium that comprises a promoter and coding sequence that encodes GLP-1(1-37),
    wherein the promoter and coding sequence that encodes the signal protein or peptide GLP-1(1-37) comprise SEQ ID NO: 19, said GLP-1(1-37) is expressed and secreted by the recombinant *Lactobacillus* bacterium in the intestine of the mammalian host, and intestinal epithelial cells of the mammalian host differentiate into glucose responsive insulin secreting cells.

5. The method of claim 1 wherein the mammalian host is a human.

6. The method of claim 4, wherein the mammalian host has type 1 diabetes.

7. The method of claim 6, wherein the mammalian host is a human.

8. The method of claim 4, wherein the mammalian host is a human.

9. The method of claim 4, wherein the recombinant *Lactobacillus* cell is administered in an amount of at least about $2 \times 10^{10}$ CFU/kg of the host's weight.

10. The method of claim 4, wherein the recombinant *Lactobacillus* cell is administered in an amount selected from group consisting of at least about 5 g/day to about 15 g/day, and at least about 50 mg/day to about 150 mg/day.

11. The method of claim 4, wherein the mammalian host has type 2 diabetes.

12. The method of claim 11, wherein the mammalian host is a human.

13. A method of preventing or reducing hyperglycemia in a mammalian host who has diabetes or metabolic syndrome comprising the step of:
    administering orally to the mammalian host a therapeutically effective amount of a recombinant *Lactobacillus* bacterium that comprises a promoter and coding sequence that encodes GLP-1(1-37),
    wherein the promoter and coding sequence that encodes GLP-1(1-37) comprise SEQ ID NO: 19, said GLP-1(1-37) is expressed and secreted by the recombinant *Lactobacillus* bacterium in the intestine of the mammalian host, and intestinal epithelial cells of the mammalian host differentiate into glucose responsive insulin secreting intestinal cells.

14. The method of claim 13, wherein the recombinant *Lactobacillus* cell is administered in an amount of at least about $2 \times 10^{10}$ CFU/kg of the host's weight.

15. The method of claim 13, wherein the recombinant *Lactobacillus* cell is administered in an amount selected from group consisting of at least about 5 g/day to about 15 g/day, and at least about 50 mg/day to about 150 mg/day.

16. The method of claim 13, wherein the mammalian host is a human.

17. The method of claim 13, wherein the mammalian host has type 1 diabetes.

18. The method of claim 17, wherein the mammalian host is a human.

19. The method of claim 13, wherein the mammalian host has type 2 diabetes.

20. The method of claim 19, wherein the mammalian host is a human.

* * * * *

SEQUENCE LISTING

```
<160> NUMBER OF SEQ ID NOS: 27

<210> SEQ ID NO 1
<211> LENGTH: 33
<212> TYPE: PRT
<213> ORGANISM: Homo sapiens

<400> SEQUENCE: 1

His Ala Asp Gly Ser Phe Ser Asp Glu Met Asn Thr Ile Leu Asp Asn
1               5                   10                  15

Leu Ala Ala Arg Asp Phe Ile Asn Trp Leu Ile Gln Thr Lys Ile Thr
            20                  25                  30

Asp
```

<210> SEQ ID NO 2
<211> LENGTH: 33
<212> TYPE: PRT
<213> ORGANISM: Artificial Sequence
<220> FEATURE:
<223> OTHER INFORMATION: Synthetic sequence
<220> FEATURE:
<221> NAME/KEY: misc_feature
<222> LOCATION: (13)..(13)
<223> OTHER INFORMATION: Xaa can be any naturally occurring amino acid
<220> FEATURE:
<221> NAME/KEY: misc_feature
<222> LOCATION: (16)..(16)
<223> OTHER INFORMATION: Xaa can be any naturally occurring amino acid
<220> FEATURE:
<221> NAME/KEY: misc_feature
<222> LOCATION: (19)..(20)
<223> OTHER INFORMATION: Xaa can be any naturally occurring amino acid
<220> FEATURE:
<221> NAME/KEY: misc_feature
<222> LOCATION: (27)..(28)
<223> OTHER INFORMATION: Xaa can be any naturally occurring amino acid

<400> SEQUENCE: 2

His Ala Asp Gly Ser Phe Ser Asp Glu Met Asn Thr Xaa Leu Asp Xaa
 1               5                  10                  15

Leu Ala Xaa Xaa Asp Phe Ile Asn Trp Leu Xaa Xaa Thr Lys Ile Thr
            20                  25                  30

Asp

<210> SEQ ID NO 3
<211> LENGTH: 33
<212> TYPE: PRT
<213> ORGANISM: Artificial sequence
<220> FEATURE:
<223> OTHER INFORMATION: Synthetic sequence
<220> FEATURE:
<221> NAME/KEY: misc_feature
<222> LOCATION: (19)..(19)
<223> OTHER INFORMATION: Xaa can be any naturally occurring amino acid

<400> SEQUENCE: 3

His Ala Asp Gly Ser Phe Ser Asp Glu Met Asn Thr Ile Leu Asp Asn
 1               5                  10                  15

Leu Ala Xaa Arg Asp Phe Ile Asn Trp Leu Ile Gln Thr Lys Ile Thr
            20                  25                  30

Asp

<210> SEQ ID NO 4
<211> LENGTH: 270
<212> TYPE: DNA
<213> ORGANISM: Artificial Sequence
<220> FEATURE:
<223> OTHER INFORMATION: Synthetic sequence

<400> SEQUENCE: 4
atggcacaag tcattaatac caacagcctc tcgctgatca ctcaaaataa tatcaacaag     60
atgcatcatc atcatcatca cggatccgat ctgtacgacg atgacgataa gcacgatgaa    120
tttgagagac atgctgaagg gacctttacc agtgatgtaa gttcttattt ggaaggccaa    180
gctgccaagg aattcattgc ttggctggtg aaaggccgag gatgcggtgg cggttacggc    240
cgtaaaaaac gtcgtcagcg ccgtcgctaa                                     270

<210> SEQ ID NO 5

```
<211> LENGTH: 60
<212> TYPE: DNA
<213> ORGANISM: Artificial sequence
<220> FEATURE:
<223> OTHER INFORMATION: Synthetic sequence

<400> SEQUENCE: 5
atggcacaag tcattaatac caacagcctc tcgctgatca ctcaaaataa tatcaacaag       60

<210> SEQ ID NO 6
<211> LENGTH: 27
<212> TYPE: DNA
<213> ORGANISM: Artificial Sequence
<220> FEATURE:
<223> OTHER INFORMATION: Synthetic sequence

<400> SEQUENCE: 6
atgcatcatc atcatcatca cggatcc                                          27

<210> SEQ ID NO 7
<211> LENGTH: 15
<212> TYPE: DNA
<213> ORGANISM: Artificial Sequence
<220> FEATURE:
<223> OTHER INFORMATION: Synthetic sequence

<400> SEQUENCE: 7
gacgatgacg ataag                                                       15

<210> SEQ ID NO 8
<211> LENGTH: 111
<212> TYPE: DNA
<213> ORGANISM: Artificial Sequence
<220> FEATURE:
<223> OTHER INFORMATION: Synthetic sequence

<400> SEQUENCE: 8
cacgatgaat tgagagaca tgctgaaggg acctttacca gtgatgtaag ttcttatttg       60
gaaggccaag ctgccaagga attcattgct tggctggtga aaggccgagg a              111

<210> SEQ ID NO 9
<211> LENGTH: 48
<212> TYPE: DNA
<213> ORGANISM: Artificial Sequence
<220> FEATURE:
<223> OTHER INFORMATION: Synthetic sequence

<400> SEQUENCE: 9
tgcggtggcg gttacggccg taaaaaacgt cgtcagcgcc gtcgctaa                   48

<210> SEQ ID NO 10
<211> LENGTH: 708
<212> TYPE: DNA
<213> ORGANISM: Artificial Sequence
<220> FEATURE:
<223> OTHER INFORMATION: Synthetic sequence

<400> SEQUENCE: 10
tgcatgcatc catcaaaaaa atattctcaa cataaaaaac tttgtgtaat actcagggtt       60
gacggcgatt gagccgacgg gtggaaaccc aatacgtaat caacgacttg caatatagga     120
taacgaatca tggcacaagt cattaatacc aacagcctct cgctgatcac tcaaaataat     180
atcaacaagc tcgagcatca tcatcatcat cacggatccg atctgtacga cgatgacgat     240
aagcacgatg aatttgagag acatgctgaa gggaccttta ccagtgatgt aagttcttat     300
```

| | |
|---|---|
| ttggaaggcc aagctgccaa ggaattcatt gcttggctgg tgaaaggccg aggatgcggt | 360 |
| ggcggttacg gccgtaaaaa acgtcgtcag cgccgtcgct aatcgtcgta aactgattaa | 420 |
| ctgagactga cggcaacgcc aaattgcctg atgcgctgcg cttatcaggc ctacaaggtg | 480 |
| aattgcaatt tattgaattt gcacattttt gtaggccgga taaggcgttt acgccgcatc | 540 |
| cggcaacatg aatggtaatt tgtcagcaac gtgcttcccc gccaacggcg gggttttttc | 600 |
| tgcccgcaat ttaccgataa cccccaaata acccctcatt tcacccacta atcgtccgat | 660 |
| taaaacccct gcagaaacgg ataatcatgc cgataactca tataacgc | 708 |

<210> SEQ ID NO 11
<211> LENGTH: 53
<212> TYPE: DNA
<213> ORGANISM: Artificial Sequence
<220> FEATURE:
<223> OTHER INFORMATION: Synthetic sequence

<400> SEQUENCE: 11

| | |
|---|---|
| tgcatgcatc catcaaaaaa atattctcaa cataaaaaac tttgtgtaat act | 53 |

<210> SEQ ID NO 12
<211> LENGTH: 76
<212> TYPE: DNA
<213> ORGANISM: Artificial Sequence
<220> FEATURE:
<223> OTHER INFORMATION: Synthetic sequence

<400> SEQUENCE: 12

| | |
|---|---|
| cagggttgac ggcgattgag ccgacgggtg gaaacccaat acgtaatcaa cgacttgcaa | 60 |
| tataggataa cgaatc | 76 |

<210> SEQ ID NO 13
<211> LENGTH: 60
<212> TYPE: DNA
<213> ORGANISM: Artificial Sequence
<220> FEATURE:
<223> OTHER INFORMATION: Synthetic sequence

<400> SEQUENCE: 13

| | |
|---|---|
| atggcacaag tcattaatac caacagcctc tcgctgatca ctcaaaataa tatcaacaag | 60 |

<210> SEQ ID NO 14
<211> LENGTH: 27
<212> TYPE: DNA
<213> ORGANISM: Artificial Sequence
<220> FEATURE:
<223> OTHER INFORMATION: Synthetic sequence

<400> SEQUENCE: 14

| | |
|---|---|
| atgcatcatc atcatcatca cggatcc | 27 |

<210> SEQ ID NO 15
<211> LENGTH: 15
<212> TYPE: DNA
<213> ORGANISM: Artificial Sequence
<220> FEATURE:
<223> OTHER INFORMATION: Synthetic sequence

<400> SEQUENCE: 15

| | |
|---|---|
| gacgatgacg ataag | 15 |

<210> SEQ ID NO 16

<211> LENGTH: 111
<212> TYPE: DNA
<213> ORGANISM: Artificial Sequence
<220> FEATURE:
<223> OTHER INFORMATION: Synthetic sequence

<400> SEQUENCE: 16

```
cacgatgaat tgagagaca tgctgaaggg acctttacca gtgatgtaag ttcttatttg      60
gaaggccaag ctgccaagga attcattgct tggctggtga aaggccgagg a             111
```

<210> SEQ ID NO 17
<211> LENGTH: 48
<212> TYPE: DNA
<213> ORGANISM: Artificial Sequence
<220> FEATURE:
<223> OTHER INFORMATION: Synthetic sequence

<400> SEQUENCE: 17

```
tgcggtggcg gttacggccg taaaaaacgt cgtcagcgcc gtcgctaa                  48
```

<210> SEQ ID NO 18
<211> LENGTH: 306
<212> TYPE: DNA
<213> ORGANISM: Artificial Sequence
<220> FEATURE:
<223> OTHER INFORMATION: Synthetic sequence

<400> SEQUENCE: 18

```
tcgtcgtaaa ctgattaact gagactgacg gcaacgccaa attgcctgat gcgctgcgct      60
tatcaggcct acaaggtgaa ttgcaattta ttgaatttgc acattttgt aggccggata     120 aggcgtttac gccgcatccg gcaacatgaa tggtaatttg tcagcaacgt gcttccccgc    180
caacggcggg ttttttctg cccgcaattt accgataacc cccaaataac ccctcatttc     240
acccactaat cgtccgatta aaaccctgc agaaacggat aatcatgccg ataactcata     300
taacgc                                                                306
```

<210> SEQ ID NO 19
<211> LENGTH: 570
<212> TYPE: DNA
<213> ORGANISM: Artificial Sequence
<220> FEATURE:
<223> OTHER INFORMATION: Synthetic sequence

<400> SEQUENCE: 19

```
taacccgggg ggagtataac agaaacctta aggcccgacc gcttgacaag ggcgcgtgag      60
gtttttacga tagcgccgga tgcggggaaa aagggctcct tttgggggt tttccccgca     120 ccgggcggac ctgggcggag aggaaacgcg gcaactcgcc cgtctcgggt tcccgcccac    180
gacccttaag gaggtgtgag gcatatgaaa aaaagatta tctcagctat tttaatgtct     240
acagtgatac tttctgctgc agccccgttg tcaggtgttt acgctgatac taattctgat    300
ttggaaatat cgtcgacttg tgatgctcat catcatcatc atcacgacga tgacgataag    360
cacgatgaat tgagagaca tgctgaaggg acctttacca gtgatgtaag ttcttatttg    420
gaaggccaag ctgccaagga attcattgct tggctggtga aaggccgagg atgcggtggc    480
ggttacggcc gtaaaaaacg tcgtcagcgc cgtcgctaat aaaataaca aaagagtat     540 gagttttgc tcatactctt tttgttattt                                       570
```

<210> SEQ ID NO 20
<211> LENGTH: 204

```
<212> TYPE: DNA
<213> ORGANISM: Artificial Sequence
<220> FEATURE:
<223> OTHER INFORMATION: Synthetic sequence

<400> SEQUENCE: 20
taacccgggg ggagtataac agaaacctta aggcccgacc gcttgacaag ggcgcgtgag    60
gtttttacga tagcgccgga tgcggggaaa aagggctcct tttgggggt tttccccgca    120 ccgggcggac ctgggcggag aggaaacgcg gcaactcgcc cgtctcgggt tcccgcccac   180
gacccttaag gaggtgtgag gcat                                          204

<210> SEQ ID NO 21
<211> LENGTH: 96
<212> TYPE: DNA
<213> ORGANISM: Artificial Sequence
<220> FEATURE:
<223> OTHER INFORMATION: Synthetic sequence

<400> SEQUENCE: 21
atgaaaaaaa agattatctc agctatttta atgtctacag tgatactttc tgctgcagcc   60
ccgttgtcag gtgtttacgc tgatactaat tctgat                              96

<210> SEQ ID NO 22
<211> LENGTH: 27
<212> TYPE: DNA
<213> ORGANISM: Artificial Sequence
<220> FEATURE:
<223> OTHER INFORMATION: Synthetic sequence

<400> SEQUENCE: 22
ttggaaatat cgtcgacttg tgatgct                                        27

<210> SEQ ID NO 23
<211> LENGTH: 18
<212> TYPE: DNA
<213> ORGANISM: Artificial Sequence
<220> FEATURE:
<223> OTHER INFORMATION: Synthetic sequence

<400> SEQUENCE: 23
catcatcatc atcatcac                                                  18

<210> SEQ ID NO 24
<211> LENGTH: 15
<212> TYPE: DNA
<213> ORGANISM: Artificial Sequence
<220> FEATURE:
<223> OTHER INFORMATION: Synthetic sequence

<400> SEQUENCE: 24
gacgatgacg ataag                                                     15

<210> SEQ ID NO 25
<211> LENGTH: 111
<212> TYPE: DNA
<213> ORGANISM: Artificial Sequence
<220> FEATURE:
<223> OTHER INFORMATION: Synthetic sequence

<400> SEQUENCE: 25
cacgatgaat tgagagaca tgctgaaggg acctttacca gtgatgtaag ttcttatttg    60
gaaggccaag ctgccaagga attcattgct tggctggtga aaggccgagg a            111
```

```
<210> SEQ ID NO 26
<211> LENGTH: 54
<212> TYPE: DNA
<213> ORGANISM: Artificial Sequence
<220> FEATURE:
<223> OTHER INFORMATION: Synthetic sequence

<400> SEQUENCE: 26
tgcggtggcg gttacggccg taaaaaacgt cgtcagcgcc gtcgctaata ataa         54

<210> SEQ ID NO 27
<211> LENGTH: 48
<212> TYPE: DNA
<213> ORGANISM: Artificial Sequence
<220> FEATURE:
<223> OTHER INFORMATION: Synthetic sequence

<400> SEQUENCE: 27
aaataacaaa aagagtatga gttttgctc atactctttt tgttattt                 48
```